US 6,569,426 B2
(12) United States Patent
Smith et al.

(10) Patent No.: US 6,569,426 B2
(45) Date of Patent: May 27, 2003

(54) TRESYL-MONOMETHOXYPOLYETHYLENE GLYCOL-MODIFIED VIRUSES HAVING VIRAL INFECTIVITY

(75) Inventors: Alan E. Smith, Dover, MA (US); Catherine R. O'Riordan, Jamaica Plain, MA (US); Gillian E. Francis, Reading (GB); Vincent Parkes, Trusham (GB); Christina Delgado, London (GB)

(73) Assignees: Genzyme Corporation, Framingham, MA (US); Polymasc Pharmaceuticals, London (GB)

( * ) Notice: Subject to any disclaimer, the term of this patent is extended or adjusted under 35 U.S.C. 154(b) by 0 days.

(21) Appl. No.: 09/409,803

(22) Filed: Sep. 30, 1999

(65) Prior Publication Data

US 2002/0034498 A1 Mar. 21, 2002

Related U.S. Application Data

(63) Continuation of application No. PCT/US98/06609, filed on Apr. 3, 1998.

(30) Foreign Application Priority Data

| Apr. 3, 1997 | (GB) | ............................................... | 9706735 |
| Sep. 15, 1997 | (GB) | ............................................... | 9719625 |
| Oct. 22, 1997 | (GB) | ............................................... | 9722316 |

(51) Int. Cl.$^7$ .......................... A01N 63/00; C12N 7/01; C12N 15/86; A61K 31/7088; C08H 1/00
(52) U.S. Cl. .................. 424/93.6; 424/93.2; 435/235.1; 435/320.1; 514/44; 530/402; 530/810; 530/815
(58) Field of Search ............................... 424/93.2, 93.6; 514/44; 435/235.1, 620.1; 530/402, 810, 815

(56) References Cited

U.S. PATENT DOCUMENTS

| 4,179,337 A | * | 12/1979 | Davis et al. ................. 435/181 |
| 5,166,320 A | * | 11/1992 | Wu et al. .................... 530/395 |
| 5,552,309 A | | 9/1996 | March ....................... 435/172.3 |
| 5,731,172 A | * | 3/1998 | Saito et al. ............... 435/91.42 |
| 5,797,870 A | | 8/1998 | March et al. .................. 604/49 |
| 5,840,059 A | | 11/1998 | March et al. .................. 604/53 |

FOREIGN PATENT DOCUMENTS

| WO | 9614874 A | 5/1996 |
| WO | 9621036 A | 7/1996 |

* cited by examiner

*Primary Examiner*—David M. Naff
(74) *Attorney, Agent, or Firm*—Baker Botts L.L.P.

(57) ABSTRACT

Viruses are modified by coupling a polymer such as polyethylene glycol to obtain polymer-modified viruses that can exhibit reduced antigenicity while retaining infectivity, and which may exhibit increased circulation time in vivo. The polymer may be directly covalently attached or indirectly covalently attached via an intermediate coupling moiety to the virus. The polymer may also be indirectly noncovalently attached to the virus via a ligand such as an antibody having specificity for a viral surface component. To prepare the polymer-modified virus, the polymer is activated and coupled to the virus. A preferred activated polymer is tresyl-monomethoxypolyethylene glycol having an average molecular weight of about 5000 daltons. The polymer-modified viruses have utility for therapeutic and diagnostic in vivo applications, and may be used to introduce a transgene into a target cell by infection, or be administered to a subject having a tumor where the polymer-modified virus localizes to the tumor.

15 Claims, 54 Drawing Sheets

Lane 1 Standards
Lane 2 Control Antibody
Lane 3 PEGylated Antibody

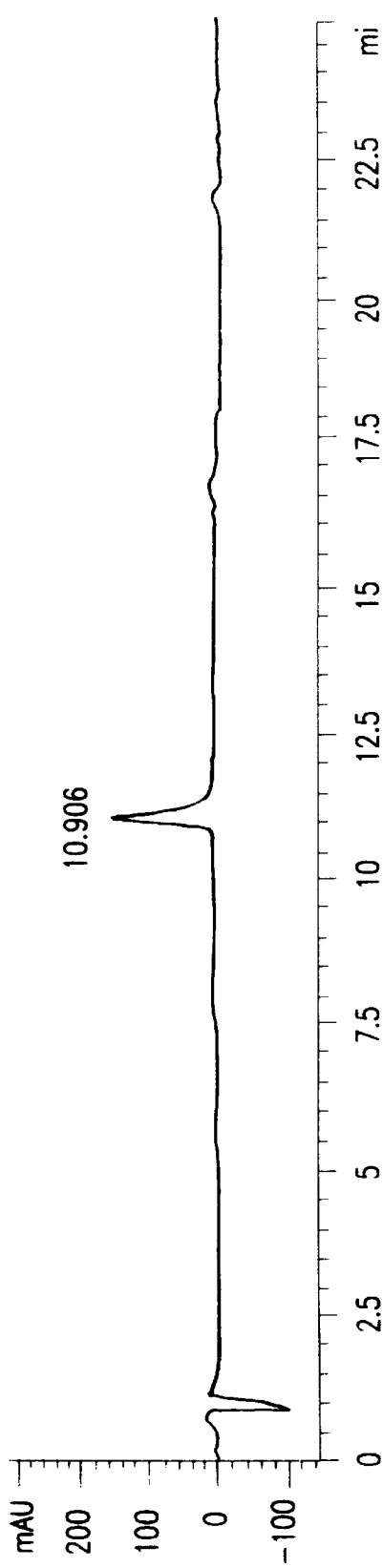
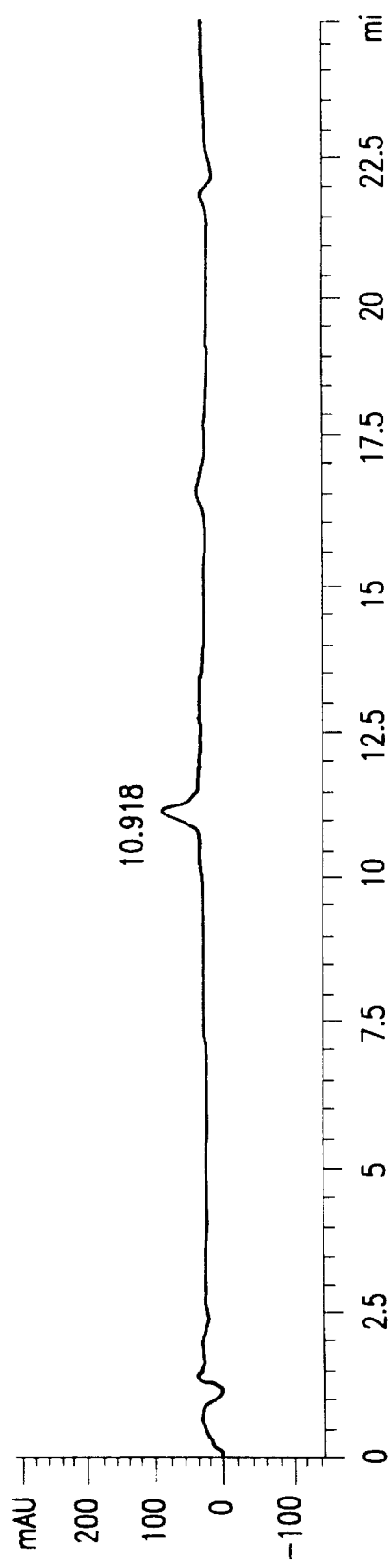
FIG.19A
FIG.19B

- INFECTIVITY OF ONYX-015 BEFORE INCUBATION WITH TMPEG
- INFECTIVITY OF ONYX-015 AFTER INCUBATION WITH TMPEG
- INFECTIVITY OF ONYX-015 AFTER INCUBATION WITH MPEG

- INFECTIVITY OF ONYX-015 BEFORE INCUBATION WITH TMPEG
○ INFECTIVITY OF ONYX-015 AFTER INCUBATION WITH TMPEG
▽ INFECTIVITY OF ONYX-015 AFTER INCUBATION WITH MPEG

- ● INFECTIVITY OF ONYX-015 BEFORE INCUBATION WITH TMPEG
- ○ INFECTIVITY OF ONYX-015 AFTER INCUBATION WITH TMPEG
- ▽ INFECTIVITY OF ONYX-015 AFTER INCUBATION WITH MPEG

FIG.24A
MPEG 20% 
TMPEG 20% 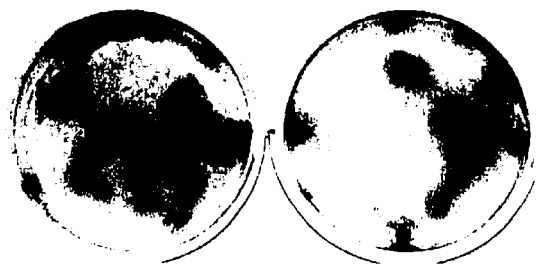
FIG.24B

NEUTRALISATION OF VACCINIA VIRUS AFTER INCUBATION WITH MPEG
NEUTRALISATION OF VACCINIA VIRUS AFTER INCUBATION WITH TMPEG

FIG.27

TRESYL-MONOMETHOXYPOLYETHYLENE GLYCOL-MODIFIED VIRUSES HAVING VIRAL INFECTIVITY

The present application is a continuation of PCT/US98/06609, filed Apr. 3, 1998, which claims priority from United Kingdom Patent Application Nos. 9706735.9, 9719625.7 and 9722316.8 filed Apr. 3, 1997, Sep. 15, 1997 and Oct. 22, 1997, respectively.

BACKGROUND OF THE INVENTION

Viruses have many potential therapeutic uses, for example in gene therapy, whereby the viral genome is used as a vector for foreign genes, as well as in vaccination and cancer therapy, for example by exploiting the phenomenon of viral oncolysis, which exploits cell destruction following selective virus replication in certain tumors.

However, clinical use of viruses presents certain problems. For example, many human subjects are pre-immune to common viruses such as adenoviruses, and thus have circulating antibodies. In cases in which the circulating antibodies are neutralizing in nature, the administered viral particles may have reduced or no infectivity. Repeated administration may exacerbate this problem, since most viruses are highly immunogenic. Immune responses may also contribute to the toxicity of viral administration, and in cases in which cellular immunity is involved, some profound tissue damage may result.

In addition to problems related to the immune system, virus particles are also potentially vulnerable to other clearance mechanisms. Particulates tend to be filtered by the liver and spleen via a mechanism involving phagocytic/endocytic uptake by macrophages. Viral aggregates may be cleared by such mechanisms. In addition, activation of the complement system by viruses may be a factor involved in the inactivation of some viral vectors. Proteolysis and, where relevant, lipolysis, may also potentially damage viral particles.

Viral particles also often have highly specific tissue distribution. This is not always desirable in the therapeutic applications envisaged for the virus. For example, it is desirable in some settings to circumvent the natural viral tissue distribution, possibly simultaneously 'targeting' the virus to a new site such as a tumor. With appropriate modification of viral vectors, both active and passive targeting strategies should be feasible with such vectors. However, abrogation of tissue specific localization systems may make viral particles more susceptible to non-specific uptake mechanisms. One form of passive targeting particularly relevant to viral vectors for use in gene therapy for cancer or in viral oncolysis is the so-called enhanced permeability and retention effect, which exploits leaky vasculature and poor lymphatic drainage in tumors, which can achieve enhanced localization of particulates.

Virus particles also have veterinary and agricultural uses which share some of the above problems.

Polymer modification has been shown, in the context of polymer-protein and polymer-liposome constructs, to have the potential to solve many problems. For example, polymer cover has been demonstrated to reduce antigenicity and immunogenicity. In addition, light polymer cover can turn an antigen into a tolerogen. Polymer cover can also ameliorate reticuloendothelial system (RES) uptake of particulates. Further, polymer can serve as a linker to couple targeting devices to the surface of other molecules or macromolecular structures to target them to specific sites.

However, living viruses are very different in their characteristics to proteins and liposomes. The surface structures involved in infectivity might well be compromised by polymer modification. Virtually all clinical applications of viruses require infectivity to be maintained.

I has been surprisingly found in accordance with the present invention that viral particles can be polymer modified and yet retain infectivity. It has also been discovered that polymer modification of viruses results in the acquisition of beneficial properties such as improved capacity to infect in the presence of neutralizing antibodies.

SUMMARY OF THE INVENTION

The present invention provides viruses modified by polymers. In a preferred embodiment the polymer is polyethylene glycol (PEG). In one embodiment, the polymer is directly covalently attached to the virus. In another embodiment, the polymer is indirectly covalently attached to the virus via an intermediate coupling moiety. In yet another embodiment, the polymer is indirectly noncovalently attached to the virus via a ligand. In a preferred embodiment, the ligand has specificity for a viral surface component. For example, the ligand may be an antibody.

The present invention further provides a method of making viruses modified by polymers, whereby the modified viruses retain infectivity.

Another embodiment of the present invention provides a method for introducing a transgene into a target cell comprising contacting the target cell with a polymer-modified virus, wherein the virus comprises the transgene.

The present invention further provides a method of delivering a virus to a tumor, comprising administering a polymer-modified virus of the invention to a subject in need of such treatment under conditions whereby the polymer-modified virus localizes to a tumor.

In another embodiment, the present invention provides a composition comprising a virus modified by a polymer and a carrier.

BRIEF DESCRIPTION OF THE DRAWINGS

FIGS. 19A–C shows the elution profile of untreated (panel 19a), MPEG treated (panel 19b) and TMPEG treated (panel 19C) Adenovirus ONYX-015 from 1 ml Resource Q column (Pharmacia).

FIG. 24 shows photographs demonstrating infectivity measured by β-galactosidase expression of vaccinia virus, following step-wise addition of $MPEG_{5000}$ or $TMPEG_{5000}$.

FIG. 27 demonstrates protection from neutralisation by anti-vaccinia serum for Vaccinia virus which had been incubated with $TMPEG_{5000}$ (step-wise addition).

DETAILED DESCRIPTION OF THE INVENTION

Figure 1:
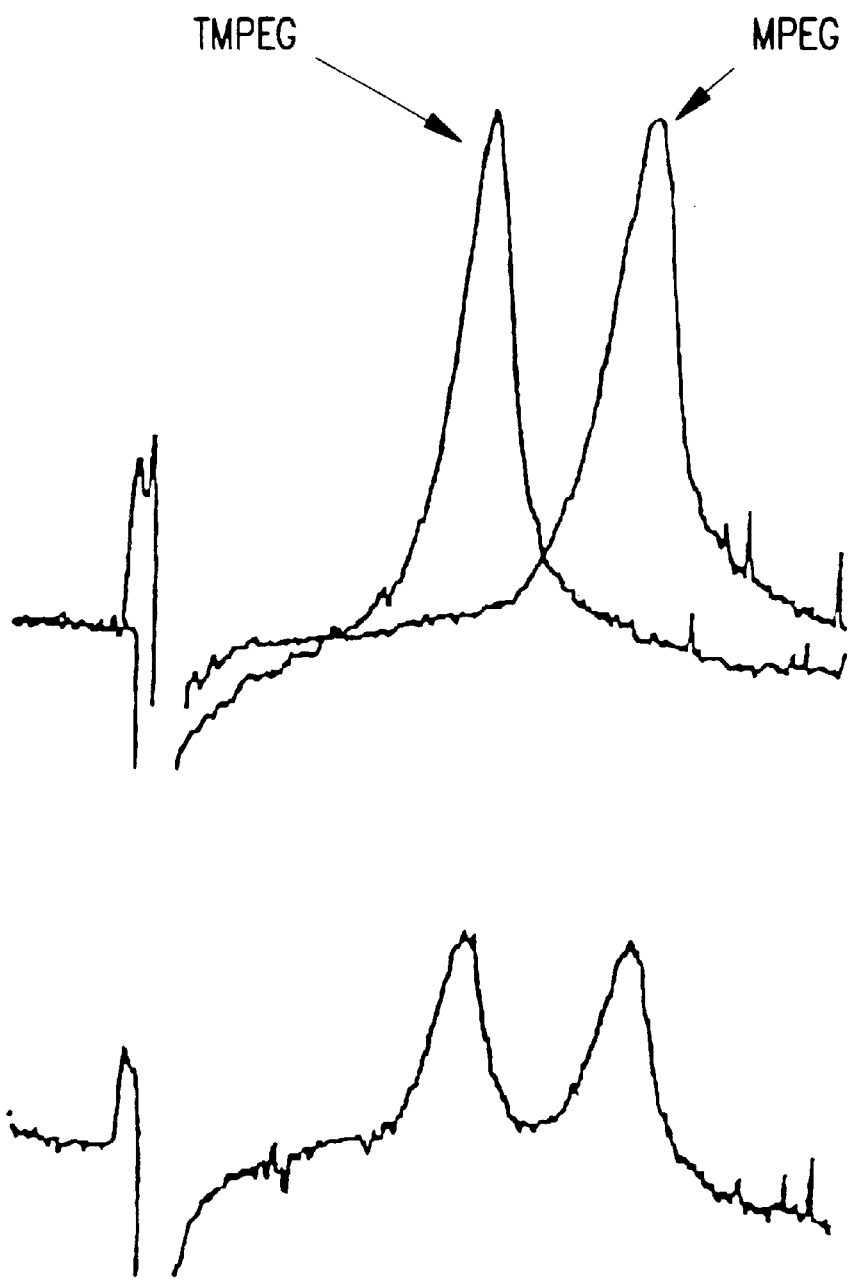
FIG. 1 shows capillary electropherographs of adenovirus treated with 3% (w/v) TMPEG and MPEG.

The present invention provides viruses modified by polymers. Such a viral particle has one or more polymer molecules covalently or noncovalently bound thereto. The polymer-modified viruses of the present invention maintain the biological property of infectivity.

In accordance with the present invention, polymers are generally large non-immunogenic, biologically inert molecules comprising a chain of smaller molecules linked by covalent bonds. Polymers useful in accordance with the present invention are those polymers which, when covalently or noncovalently bound to a virus, provide a polymer-modified virus that retains detectable levels of infectivity and is substantially non-immunogenic. The polymers preferably have an average molecular weight of from about 200 to about 20,000 daltons. The polymers are biocompatible, and may be linear or branched. The polymers may be homopolymers or heteropolymers. Suitable polymers for use in the present invention include polyalkalene compounds such as polyalkalene oxides and glycols. Polyalkalene compounds include polyoxymethylene, polyethylene glycols (PEG) and oxides, and methoxypolyethyleneglycols, and derivatives thereof including for example polymethyl-ethyleneglycol, polyhydroxypropyleneglycol, polypropylene glycol, polymethylpropylene glycol, polyhydroxypropylene oxide and polyvinyl pyrrolidone (PVP).

A preferred polymer in accordance with the present invention is PEG. PEG is a water-soluble polymer having the formula $H(OCH_2CH_2)_nOH$, wherein n is the number of repeating units and determines the average molecular weight. PEGs having average molecular weights of from 200 to 20,000 daltons are commercially available. In accordance with the present invention, PEG having an average molecular weight of from 200 ($PEG_{200}$) to 20,000 ($PEG_{20,000}$) may be used to prepare viruses modified by PEG. In a preferred embodiment, the PEG has an average molecular weight of from about 2000 to about 12,000. In a more preferred embodiment, the PEG has an average molecular weight of about 5000.

It has been discovered in accordance with the present invention that polymer-modified viruses can exhibit reduced antigenicity while retaining infectivity. Accordingly, viruses that are useful for the present invention include viruses for which the properties of infectivity and reduced antigenicity are desired. Further, the polymer-modified viruses of the present invention may exhibit increased circulation time in vivo. Thus the present polymer-modified viruses have utility for therapeutic and diagnostic in vivo applications.

The polymer-modified viruses have utility in medical therapy and diagnosis in medical and veterinary practice and in agriculture. They are of particular use in gene therapy (for example the delivery of genes for the localized expression of a desired gene product) and for non-gene therapy applications such as, but without limitation, viral oncolysis. The viruses are useful, for example, to deliver genes, toxins and/or diagnostic markers. An additional application is in the creation of tolerogens for viral antigens. More specifically, the present invention is directed to a virus selected from RNA and DNA viruses. Preferably the virus used is selected from the following families and groups: Adenoviridae; Birnaviridae; Bunyaviridae; Caliciviridae; Capillovirus group; Carlavirus group; Carmovirus virus group; Group Caulimovirus; Closterovirus Group; Commelina yellow mottle virus group; Comovirus virus group; Coronaviridae; PM2 phage group: Corcicoviridae; Group Cryptic virus; group Cryptovirus; Cucumovirus virus group Family φ6 phage group; Cystoviridae; Group Carnation ringspot; Dianthovirus virus group; Group Broad bean wilt; Fabavirus virus group; Filoviridae; Flaviviridae; Furovirus group; Group Geminivirus; Group Giardiavirus; Hepadnaviridae; Herpesviridae; Hordeivirus virus group; Ilarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae including adeno-associated viruses; Paramyxoviridae; Parsnip yellow fleck virus group; Partitiviridae; Parvoviridae; Pea enation mosaic virus group; Phycodnaviridae; Picornaviridae; Plasmaviridae; Podoviridae; Polydnaviridae; Potexvirus group; Potyvirus; Poxviridae; Reoviridae; Retroviridae; Rhabdoviridae; Group Rhizidiovirus; Siphoviridae; Sobemovirus group; SSV1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; Plant virus satellites.

Particularly preferred viruses for the purpose of delivery of transgenes include, for example, retrovirus, adenovirus, adenoassociated virus, herpesvirus and pokvirus. Adenovirus is particularly preferred.

As used herein, the term virus includes recombinant genetically engineered viruses. For example, the virus may be a virus that has been engineered such that it is incapable of replicating and exhibits minimal gene expression. The recombinant viruses may contain transgenes. Transgenes are defined herein as nucleic acids that are not native to the virus. For example, a transgene may encode a biologically functional protein or peptide, an antisense molecule, or a marker molecule.

The polymer-modified viruses of the present invention may be provided by direct covalent, indirect covalent, or indirect noncovalent attachment of the polymer to the virus.

A variety of schemes for covalent and non-covalent attachment exist: 1) polymer may be attached via direct covalent coupling to the viral surface; 2) polymer may be attached via indirect covalent coupling (e.g. via an intermediate coupling moiety which links the polymer to the viral surface); or 3) attached via an indirect non-covalent linkage using, for example, a suitable PEGylated ligand. Suitable ligands are not restricted to antibodies to surface proteins or lipid and could include hydrophobic ligands for viral particles with hydrophobic surface components such as envelope viruses.

The polymer may be attached via direct or indirect covalent coupling to the viral surface by methods that are generally known in the art for covalent attachment of polymers to other molecules, such as proteins. Targets for polymer modification include reactive groups on the viral surface with which the polymer or coupling agent can interact, including for example primary and secondary amino groups, thiol groups and aromatic hydroxy groups. Thus the preferred method for polymer modification of a virus depends upon the available target sites on the surface of the particular virus. The specificity of particular methods of polymer modification for particular target groups is well-known, and thus the ordinarily skilled artisan can select a method suitable for the desired target.

Different methods of polymer modification may be selected depending upon whether the virus is enveloped or non-enveloped. The surface of a non-enveloped virus is a protein shell, or capsid, often containing multiple types of polypeptides. Representative non-enveloped viruses include adenovirus, parvovirus and picornavirus. In enveloped viruses, the protein capsid is enclosed by a lipid bilayer that contains viral-encoded polypeptides. Representative enveloped viruses include herpesvirus, poxvirus and baculovirus. Both the capsid and the envelope polypeptides provide targets for polymer modification. For example, in a nonenveloped virus such as adenovirus, the hexon, penton cell base, and fiber proteins are targets for polymer modification. Viral polypeptides that provide sites of exposed epitopes for neutralizing antibodies, for example the adenoviral hexon protein, are particularly preferred sites for polymer modification. Modification of these sites is believed to mask the epitope from neutralizing antibodies, thus providing a viral vector with reduced antigenicity.

Methods for the direct or indirect covalent attachment of polymer, to polypeptides that are known in the art may be used to provide the polymer-modified viruses of the present invention. Methods are described, for example, in WO 90/04606, U.S. Pat. Nos. 4,179,337 and 5,612,460, the disclosures of which are incorporated herein by reference. Generally, the polymer is activated by converting a terminal moiety of the polymer to an activated moiety, or by attaching an activated coupling moiety to the polymer. The activated polymer is then coupled to the target via the activated moiety. The activated moiety or activated coupling moiety can be selected based upon its affinity for the desired target site on the viral surface.

For example, the hydroxyl end groups of PEG may be converted into reactive functional group or attached to an activated coupling moiety to provide a molecule known as "activated" PEG. Various forms of activated PEG are known in the art and are commercially available. For direct covalent linkage to virus a suitable activated PEG is MPEG-tresylate (TMPEG), which is believed to react with ε-lysine groups, or MPEG-acetaldehyde. For indirect covalent linkage other forms of activated PEG are known in the art and commercially available, including for example methoxypolyethylene glycol (MPEG) derivatives such as MPEG activated with cyanuric chloride, PEG N-hydroxysuccinimide PEG (NHS-PEG), which reacts with amine groups, and PEG-N-succimimide carbonate. These and other activated PEGs are disclosed in W095/06058, U.S. Pat. Nos. 4,179,337 and 5,612,460 incorporated herein by reference.

For example, the covalent attachment of PEG to the viral surface is accomplished by incubating the virus with the activated PEG, for example TMPEG. Several incubation regimes may be used. For instance, a single addition of the activated polymer with or without gentle mixing can be used. The optimal ratios of TMPEG to viral particles to achieve modified virus having reduced antigenicity with maintenance of infectivity may be determined by performing the assays described below. For example, virus and activated TMPEG are combined at molar ratios of activated PEG to ε-amino termini of lysine residues of from about 1:1 to about 400:1. As the amount of activated polymer to be added to the virus increases, it may be alternatively advantageous to add the activated polymer in a stepwise fashion. The rationale behind stepwise addition is that viral particles tend to aggregate and this is exacerbated by certain activated polymers, e.g. TMPEG, especially at high concentrations. Thus initial PEGylation at low polymer concentration can serve to reduce the tendency to aggregate at subsequent higher polymer concentrations and hence help to achieve a higher degree of PEGylation. For example, activated PEG such as TMPEG may be added in separate steps to a viral stock solution every thirty minutes to increase the polymer concentration each time by 3%, 5% or 8% (w/v) in the reaction mixture to obtain final polymer concentrations of 12%, 20% and 32% respectively (approximately w/v, i.e., not correcting for the volume of the polymer). In addition, after the last addition of polymer, a further incubation time might be allowed. The ordinarily skilled artisan can adjust the number of steps, concentrations of polymer, and time intervals to achieve optimal results.

The reaction may be quenched by dialysis or by addition of excess lysine, for example from 10 to 100-fold excess lysine. Alternatively, the reaction might be run to completion (i.e. the point at which the activated PEG, such as TMPEG, is either completely consumed in the PEGylation reaction or rendered inactive by hydrolysis).

For some applications, for example those requiring repeat dosing of a polymer modified virus, it may be desirable to separate unreacted polymer from polymer-modified virus, which may then be purified by standard methods as necessary for the intended use. Separation and purification may be performed by methods known in the art, for example ion exchange chromatography, gel filtration chromatography, or cesium chloride gradient purification. In situations in which there is indirect PEGylation of an antibody, hexon affinity resin may be useful to separate the PEGylated antibody from unreacted PEG.

For some applications, it may be desirable to separate unmodified virus from modified virus. In cases in which the polymer is a polyalkylene glycol, separation of modified from unmodified virus may be performed by partitioning in an aqueous biphasic polyalkylene glycol solution. For example, phase partitioning in an aqueous biphasic system of PEG and dextran may allow the separation of PEG-modified virus from unmodified virus. Partitioning may be performed by counter-current distribution. Generally, the phase system is prepared by mixing solutions of dextran and PEG. PEG and PEG-modified virus are incorporated into the phase system, mixed by inversion or rotation, and allowed to separate. PEG modified virus partitions into the PEG phase, and unmodified virus partitions into the dextran phase.

The modification of virus by PEG ("PEGylation") may be evaluated by methods known in the art, including ion exchange chromatography, capillary electrophoresis (CE), photon correlation spectroscopy (PCS), and through the use of a labeled, e.g. biotinylated, PEG in a quantitative ELISA.

Ion exchange chromatography, for example, DEAE-chromatography, can be performed by standard methods to evaluate the modified viruses based upon altered charge.

Whole virus CE provides a means to monitor the modification of virus by polymer as a function of altered surface charge. For example, covalent attachment of PEG to the virus surface seems to result in shrouding of the negative surface charges on the viral particle and thus this polymer-modified virus displays a more neutral mobility to the virus. CE may be performed by methods known to those of ordinary skill in the art. For instance, a ramped low-high voltage pre-treatment is used to electrophorese the highly mobile salt ions in which the virus may be formulated for stability, before true, high voltage separation begins. In plots derived from CE, virus particles with PEG covalently attached run at a position closer to the neutral point than virus without covalently attached PEG. CE may be conveniently used to assess the influence of various conditions, including molar ratios, concentrations and incubation times, on the covalent attachment of PEG to the virus particles. Increasing neutrality reflects increasing PEG-chain density on the virus surface.

PCS uses the relationship between particle size and movement in suspension (via Brownian motion) to gain accurate measurements on the size of the particles. This method is widely applied to monitor polymer attachment to particles including liposomes, microspheres and nanoparticles by measuring their increase in size. These data suggest that covalently attached PEG at relatively low density forms globular "mushroom" shapes and thus the increase in size is relatively small. Altering the conditions under which one would expect to increase the density of covalently attached PEG chains results in a more extended conformation of the polymer or "brush" shapes which is reflected by a relatively larger increase in particle size. Thus PCS may be used using methods known to those of ordinary skill in the art to monitor the size changes of the virus particle under different reaction conditions.

The ELISA analysis of a biotinylated PEG can provide the most quantitative assessment of the number of molecules of PEG covalently bound to a virus particle. The ELISA can be performed by standard methods known in the art.

In a preferred embodiment of the present invention, the polymer-modified virus is a recombinant virus prepared under conditions believed to provide a virus covalently modified by PEG. In a particularly preferred embodiment, the virus is a recombinant adenoviral vector. Suitable recombinant adenoviral vectors include vectors derived from adenovirus type 2 (Ad2) and type 5 (Ad5) which have been deleted for the E1 regions. Representative adenoviral vectors that are useful for delivery of a transgene are disclosed by Zabner et al. (1996) *J. Clin. Invest.* 6 1504, Zabner et al. (1993); *Cell* 75: 207, U.S. Pat. Nos. 5,707,618 and 5,670,488, the disclosures of which are incorporated herein by reference. In a preferred embodiment, the recombinant adenoviral vector contains a transgene, including for example the cystic fibrosis transmembrane conductance regulator (CFTR) gene.

In another embodiment of the invention, the polymer modified virus is a recombinant adenovirus that can induce tumor-specific cytolysis also known as viral oncolysis. Representative adenovirus that are useful for viral oncolysis are disclosed by Bischoff et al. (1996) *Science* 274:373; Heise et al. (1997) *Nature Medicine* 3:630; and EP689447A, the disclosures of which are incorporated herein by reference.

In another embodiment of the present invention, the polymer is indirectly noncovalently attached to the virus via a suitable polymer-modified ligand. Suitable ligands are not restricted to those having specificity for a viral surface component such as a viral surface protein or lipid, and may include hydrophobic ligands for viral particles with hydrophobic surface components such as envelope viruses and also ionic ligands. In a preferred embodiment, the ligand is an antibody or antibody fragment, including for example a non-neutralizing anti-virus antibody or fragment therefrom. As used herein, the term antibody includes monoclonal and polyclonal antibodies. In a particularly preferred embodiment, the ligand is a non-neutralizing anti-hexon antibody. Such antibodies are commercially available and include, for example, MAb 8052 and MAb 805 available from Chemicon International, Temecula, Calif., USA.

Indirect non-covalent attachment of polymer to the virus is accomplished by incubation of the virus with a suitable ligand that has been modified by the covalent attachment of polymer. The polymer may be covalently attached to the ligand by standard methods as described herein above. For example, a non-neutralizing anti-virus antibody such as anti-hexon antibody may be PEGylated using an activated PEG molecule as described above. In a preferred embodiment, anti-hexon antibody is modified using TMPEG. The ordinarily skilled artisan can determine the optimal ratios of activated PEG to antibody, concentrations of activated PEG and antibody, buffer and time and temperature of incubation to achieve optimal modification of the antibody. The polymer modified ligand is then incubated with the virus particles to allow non-covalent binding of the polymer modified ligand to the virus surface.

Antibodies modified with PEG at the epitope binding site may not efficiently noncovalently attach to a virus. In order to prevent PEGylation of the antibody at the epitope binding site, the PEG modification may be performed on immobilized antibody. For example, anti-hexon antibody is bound to purified immobilized hexon (eg. hexon-Sepharose) prior to PEG modification of antibody. The PEGylated antibody is then released from immobilized hexon. Alternately, anti-hexon antibody is modified by PEG, creating a population of antibodies PEGylated on the epitope binding site and other sites. The modified antibodies are then incubated with immobilized hexon, to which only antibodies modified at sites other than the epitope binding site will bind. These PEGylated antibodies are then released from the immobilized hexon for use in accordance with the present invention.

The indirect noncovalent attachment of polymer via a polymer-modified ligand may be monitored by displacement of labeled ligand from virus in a competition enzyme-linked immunosorbent assay (ELISA). For example, the ability of PEGylated anti-hexon antibody to bind to the virus surface is measured in a standard competition ELISA using, for example, biotinylated anti-hexon antibody.

The polymer-modified viruses of the present invention maintain infectivity and exhibit reduced antigenicity. It has been discovered in accordance with the present invention that viral infectivity eventually decreases upon additional polymer modification. By utilizing standard assays, including the following assays, to assess infectivity and antigenicity, those of ordinary skill in the art can determine the method and conditions of polymer modification that allow retention of infectivity and reduction in antigenicity. Under conditions designed to provide direct TMPEG polymer modified adenovirus, the methods correlating with PEGylation due to exposure to TMPEG of about 5–20% w/v are preferred, with a concentration of about 10% w/v being most preferred.

The ability of the polymer-modified viruses of the present invention to maintain infectivity may be assessed by standard infection assays. For example, the ability of the virus to infect a cell may be assessed by monitoring the expression of a transgene contained within the virus, such as a reporter gene. Genetic reporter systems are well-known in the art, and are disclosed for example in *Short Protocols in Molecular Biology*, 1995, Ausubel et al., eds., $3^{rd}$ edition, Wiley and Sons, Inc. The virus is engineered by standard methods to contain a transgene, and the polymer-modified virus is used to infect cells that are permissive for the virus. After infection under standard conditions, cell lysates are analyzed for the presence of the product of the transgene. For example, the product of the transgene can be assessed by calorimetric, chemiluminescence or fluorescence assays, or immunoassays. In this way, those of ordinary skill in the art can compare unmodified and modified virus, and can determine the optimal percentages and conditions for polymer modification that result in retention of infectivity by the polymer-modified virus. Retention of infectivity is defined herein as an infectivity level sufficient to have therapeutic value, for example at least about 20% infective relative to unmodified virus. For some therapeutic embodiments, the polymer-modified virus maintains at least 60% infectivity. In other therapeutic embodiments, the polymer-modified virus is preferred to maintain at least 80% infectivity. Lower percent infectivity of at least 5% may be therapeutically useful for applications such as viral oncolysis.

In a particular example of an infectivity assay, adenovirus genetically modified to contain the β-galactosidase (β-gal) reporter gene (lacZ) is covalently modified by exposure to various concentrations of TMPEG. A cell line permissive for adenoviral infection, for example 293 human embryonic kidney cells (ATCC CRC 1573), is exposed to unmodified and modified adenovirus containing the β-gal gene. Cells are then incubated under conditions appropriate for β-gal expression. The presence of β-gal in cell lysates is measured by standard colorimetric, fluorescence, or chemiluminescence assays. The quantity of β-gal in 293 cell lysates provides a measurement of the ability of the unmodified and PEG-modified virus to infect 293 cells. PEG-modified virus that maintains 50% infectivity relative to unmodified virus is considered to retain infectivity.

The polymer-modified viruses of the present invention may exhibit reduced antigenicity relative to unmodified virus. Reduced antigenicity is defined as a statistically significant ($p>0.05$) reduction in binding of the polymer-modified virus to neutralizing antibodies against the virus. Reduced antigenicity can be assessed by methods known in the art, including in vitro and in vivo assays. For example, both modified and unmodified viruses containing reporter genes are incubated in the presence or absence of neutralizing antibodies or serum. The antibody-treated viruses and non-antibody treated control viruses are then used to infect cells as described above, and reporter gene expression in infected cells is performed as described above. With unmodified viruses, treatment with neutralizing antibodies results in lower levels of infection and thus lower levels of transgene expression. The polymer-modified viruses of the present invention are protected from neutralization by the polymer coating, and thus provide increased infectivity and increased transgene expression in the present assays relative to unmodified viruses that have been exposed to neutralizing antibodies.

By utilizing the foregoing assays, those of ordinary skill in the art can determine the conditions for PEG modification necessary to provide a modified virus that maintains infectivity and exhibits reduced antigenicity.

Another embodiment of the present invention provides a method for introducing a transgene into a target cell. The method comprises introducing into the target cell a polymer-modified virus of the present invention, wherein the virus is a recombinant viral vector comprising the transgene. Use of the present polymer-modified viruses to deliver a transgene to a target cell is useful for the treatment of various disorders, for example in which the transgene product is absent, insufficient, or nonfunctional. Alternatively, the expression of the transgene may serve to block the expression or function of an undesired gene or gene product in the target cell.

The polymer-modified virus is introduced into the host cell by methods known in the art, including for example infection. Infection of a target cell in vivo is accomplished by contacting the target cell with the polymer-modified virus. The polymer-modified virus is delivered as a composition in combination with a physiologically acceptable carrier. As used herein, the term "physiologically acceptable carrier" includes any and all solvents, diluents, isotonic agents, and the like. The use of such media and agents for compositions is well known in the art. The polymer-modified viruses of the invention may be delivered to the target cell by methods appropriate for the target cell, including for example by ingestion, injection, aerosol, inhalation, and the like. The compositions may be delivered intravenously, by injection into tissue, such a brain or tumor, or by injection into a body cavity such as pleura or peritoneum. In a preferred embodiment, the transgene is a DNA molecule encoding CFTR or an analog or variant thereof which provides functional regulated chloride channel activity in target cells, and the complex is delivered to the airway epithelium by inhalation. DNA molecules encoding CFTR are well known in the art and disclosed for example in WO94/12649 and WO95/25796, the disclosures of which are incorporated herein by reference.

The present invention further provides a method for delivering a virus to a tumor, comprising administering a polymer-modified virus of the invention to a subject in need of such treatment under conditions whereby the polymer-modified virus localizes to a tumor. The ability of the polymer-modified viruses of the present invention to provide retention of infectivity and reduced impact of neutralizing antibodies open up this additional method of use for polymer-modified virus. Particulates of the size range 100–200 nm undergo passive tumor targeting in relation to the so-called EPR effect (Enhanced Permeability and Retention). Tumors have leaky vasculature and thus long circulating particles have the opportunity to leave the circulation and enter the tumor parenchyma via the holes in tumor blood vessels. Tumors lack lymphatics which is the main system for removal of macromolecules and particles from the tissues (the basis for the Retention element in EPR). PEG has been used to enhance the passive targeting of liposomes to tumors via increased circulation time. However, data in the scientific literature shows that this approach leads to unfavorable properties such as unacceptable low tumor to blood ratios (i.e. less than 1) for much of the lifetime of the product. Using different optimization principles it has been shown (WO 96/34598) that additional effects of PEGylation, other than improved circulation time, can be exploited to solve this problem and achieve both good tumor localization and high tumor to blood ratios as well as high tumor to normal tissue ratios. Thus the present invention provides a means of improving the tumor localization of virus particles. This is relevant to both gene therapy applications where viral vectors are used to deliver genes and for non-gene therapy applications. The latter include the recently discovered system selective for the infection of p53 deficient tumor cells which has the capacity to kill tumor cells via viral oncolysis Bischoff J R, Kim D H, Williams A, Heise C, Horn S, Muna M, Ng L, Nye J A, Sampson-Johannes A, Fattaey, McCormick F (1996) Science 274:373–376; Heise et al. (1997) Nature Medicine 3:369–645; and EP689447A, incorporated herein by reference.

In accordance with the present method, the polymer-modified virus is administered to a subject as a composition of polymer-modified virus in combination with a physiologically acceptable carrier as described hereinabove. The composition may be administered by methods appropriate in view of the location of the tumor, including for example ingestion, injection, aerosol, inhalation, and the like. In a preferred embodiment, the compositions are delivered intravenously.

The present invention further provides compositions comprising the polymer-modified viruses and further comprising a physiologically acceptable carrier. In a preferred embodiment the polymer-modified virus is a recombinant viral vector modified by covalent attachment of PEG.

The formulation of compositions is generally known in the art and reference can conveniently be made to Remington's Pharmaceutical Sciences, $17^{th}$ ed., Mack Publishing Co., Easton, Pa. The forms of the present complexes suitable for administration include sterile aqueous solutions and dispersions. The subject polymer-modified viruses are compounded for convenient and effective administration in effective amounts with a suitable physiologically acceptable carrier and/or diluent.

The precise effective amount of polymer-modified virus to be used in the methods of this invention applied to humans can be determined by the ordinary skilled artisan with consideration of individual differences in age, weight and condition of the subject.

It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired effect in association with the required carrier. The specification for the novel dosage unit forms of the invention are dictated by and directly depend on the unique characteristics of the polymer-modified viruses and the limitations inherent in the art of compounding. In the case of compositions containing supplementary active ingredients, the dosages are determined by reference to the usual dose and manner of administration of the ingredients.

The invention is further illustrated by the following specific examples which are not intended in any way to limit the scope of the invention.

EXAMPLES

When performing these assays, the skilled artisan should be aware that exposure of the virus to parent polymer that cannot covalently attach to the virus surface, and handling of the virus in buffer not containing any polymer, may influence the infectivity of the virus. These effects may be exacerbated by the type of activated polymer used and its length. Therefore, care should be taken not to associate non-specific reductions in infectivity with polymer modification of the virus surface. Suitable controls include virus sham treated with parent polymer that cannot attach to the virus surface, and a handling control in which virus is exposed to the same incubation but substituting buffer for polymer solution (e.g., no-polymer control).

Example 1
Covalent Attachment of Polyethylene Glycol to Adenovirus

Tresyl-monomethoxypolyethylene glycol (TMPEG) was prepared using $MPEG_{5000}$. In this example and in subsequent examples, except where otherwise indicated, TMPEG was prepared as set out in WO 95/06058, which corresponds to U.S. application Ser. Nos. 08/471,348 and 08/601,040, filed Jun. 6, 1995 and Feb. 23, 1996, respectively, the disclosures of which are incorporated herein by reference.

Type 2 adenovirus (genetically modified to carry the β-gal reporter gene), as disclosed in U.S. Pat. No. 5,670,488, was prepared by banding with isopycnic CsCl density centrifugation (three rounds), then extensively dialysed against phosphate buffered saline (PBS, pH 7.2) containing 5% sucrose. The stock solution used contained $6.4 \times 10^{10}$ infectious units per ml ($4.8 \times 10^{11}$ particles/ml). The virus stock was made 3% w/v by the addition of dry TMPEG, typically 3.0 mg to 100 μl of stock. The samples were incubated at 25° C. with rotary mixing for 24 h.

The polymer-treated virus was monitored via capillary electrophoresis (CE) using a Beckman P/ACE 5010 system with a 57 cm silica capillary of 50 μm Internal diameter (inlet=anode). A preliminary 1.5 min wash in 1 M NaOH and second wash in running buffer (20 mM phosphate buffer pH 7.0, 5.0 mM NaCl) were performed. Alter incubation, the samples were transferred to the CE machine where the auto sampler removed a few nanoliters by a pressure injection setting of 10 s and separation was achieved using 2 minute voltage ramping to a final of 17 Kv.

Whole virus CE monitors the changes in surface charge of the virus upon treatment with PEG. Incubation with PEG correlates with a progressively increased more neutral mobility to the virus. Increasing neutrality is consistent with an increased PEG-chain density on the virus surface.

FIG. 1 (upper panel) shows superimposed capillary electropherographs for adenovirus exposed to 3% (w/v) TMPEG and MPEG. The hiatus in each plot marks the trough at the point of neutrality. The TMPEG treated virus ran at a location significantly nearer the neutral point than the sham-treated MPEG. Under these PEGylation conditions there is no evidence of residual unPEGylated virus (i.e. no peak or shoulder on the TMPEG trace corresponding to the control virus).

In order to confirm that the mobility shift was not an artifact, a mixture of equal volumes of the two samples was loaded (FIG. 1, lower panel). Two well separated peaks were evident, corresponding to those shown in the upper panel.

Figure 2:
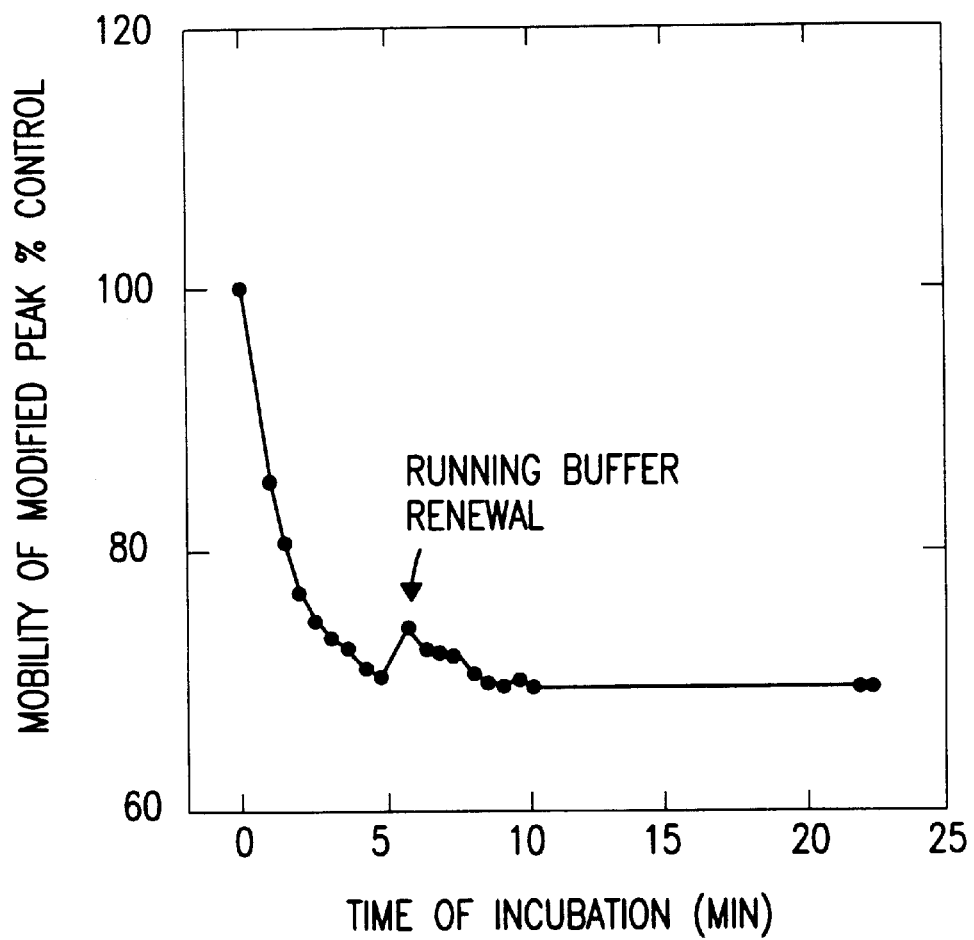
FIG. 2 is a graph of the time course of mobility change on capillary electropherographs of adenovirus treated with 3% (w/v) TMPEG.

FIG. 2 shows the time course of the change in electrophoretic mobility of virus with duration of exposure to TMPEG 3% (w/v), prepared essentially as described, above using 300 μl of virus stock and 3% (w/v) TMPEG. The % mobility was calculated as follows: (mobility of modified virus peak-mobility of neutral position)/(mobility of unmodified virus peak-mobility of neutral position)×100. Since the reaction co-product can influence the running buffer, this was renewed at the point arrowed: 100 μl of reaction mixture was analyzed up to this point (using the repeat sampling function of the CE machine, i.e. without mixing) and a fresh 100 μl aliquot of the reaction mixture was used thereafter.

Example 2
Covalent Attachment of Polyethylene Glycol to Adenovirus

Type 2 adenovirus stock solution prepared as in Example 1 ($1.35 \times 10^{10}$ infectious units per ml; $9.3 \times 10^{11}$ particles per ml) was PEGylated using 3% (w/v) TMPEG except that rotary mixing was not used so that repeated size analyses could be made.

Viral particle size was monitored using photon correlation spectroscopy (PCS) in a Malvern Instrument's ZetaMaster 5.

Figure 3A:
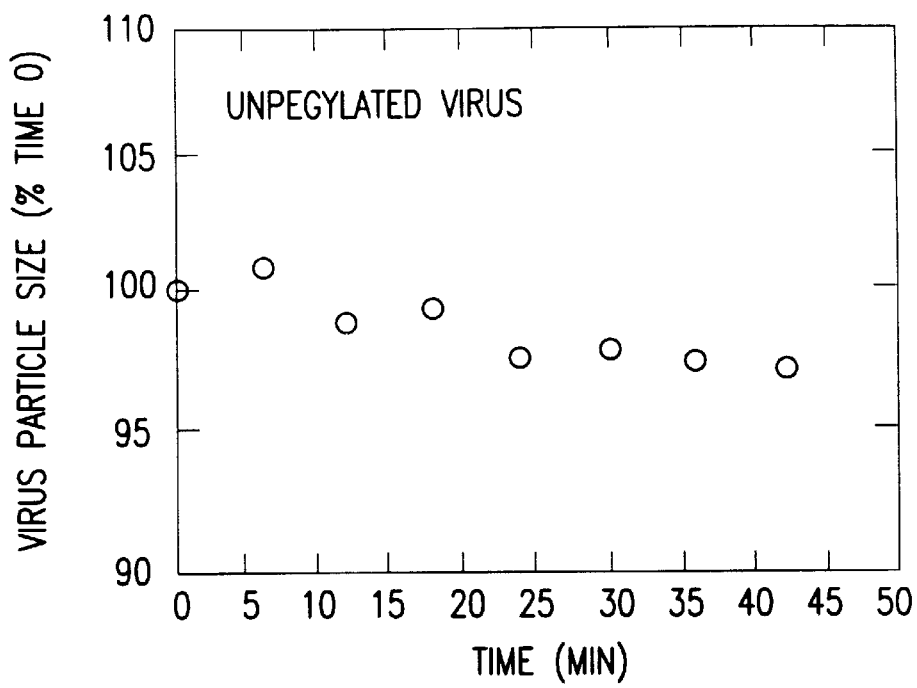
FIGS. 3A–D shows photon correlation spectroscopy results demonstrating the change in viral particle size during PEGylation.
Figure 3B:
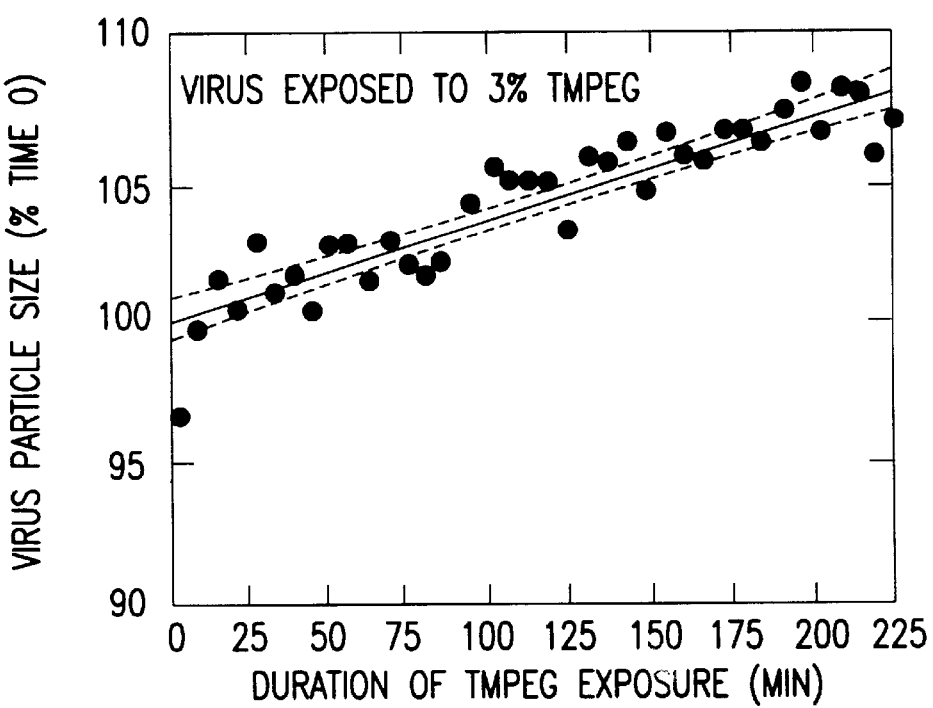
Figure 3C:
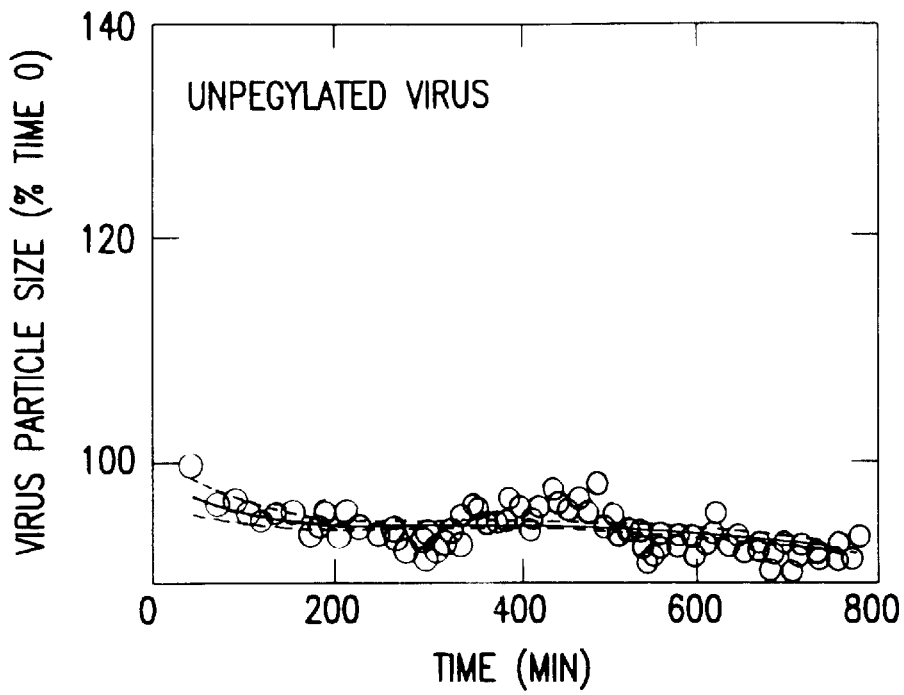
Figure 3D:
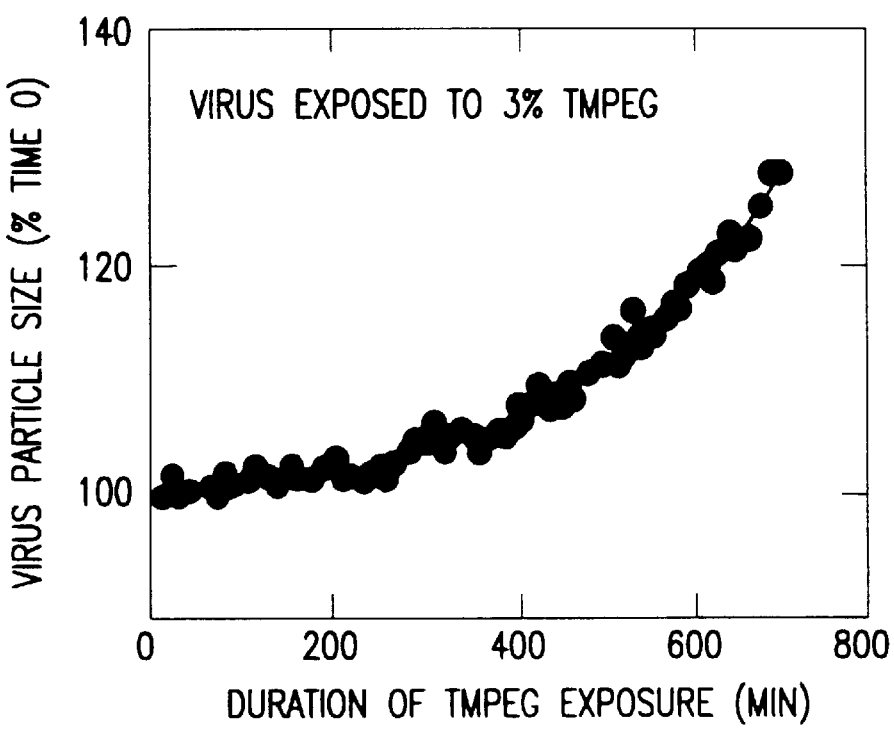

FIGS. 3a and 3b show the diameter versus time for TMPEG treated and untreated virus respectively. Results are expressed as % time 0 values. FIGS. 3c and 3d show measurements taken during a PEGylation reaction over a longer time period. Reaction with TMPEG is shown in FIG. 3d and sham treatment with MPEG is shown in FIG. 3c. Treatment with TMPEG results in an increase in particle size (FIGS. 3b and 3d) which is not seen in the control untreated virus (FIG. 3a) or in the MPEG treated virus (FIG. 3c). Increases in size are shown in FIGS. 3b and 3d. PCS has the advantage of giving numeric data and thus the method gives an ability to rank samples.

Example 3
Infectivity Assays for PEGylated and Sham Treated Virus

Several regimes of PEG treatment were evaluated with respect to retention of infectivity (see also Example 4). In addition to exposure to 3% (w/v) TMPEG, stepwise addition was also used (the objective being to achieve higher ultimate PEGylation). The rationale behind step wise addition is that viral particles tend to aggregate and this is exacerbated by PEG, especially at high concentrations. However, PEGylation has been shown, in the context of other particles (e.g. liposomes), to prevent aggregation. Thus initial PEGylation at low polymer concentration can serve to reduce the tendency to aggregate at subsequent higher polymer concentrations and hence achieve a higher degree of PEGylation. Three step wise addition regimes were used: TMPEG or MPEG were added every thirty min to viral stock solution (prepared as in Example 1) to increase the polymer concentration by 3%, 5% or 8% in the reaction mixture. Viral stocks used for these experiments ranged from $1.35–7.6 \times 10^{11}$ infectious units per ml and $9.3–20 \times 10^{11}$ particles per ml. In each experiment a maximum of four additions of dry polymer were made, equating to final polymer concentrations of 12%, 20% and 32% (~w/v, i.e. not correcting for the volume of the polymer). In some experiments the 4th addition was sampled after 30 mins and a further incubation time (giving 5 reaction conditions).

Infectivity was measured in two ways (see also Example 4). β-gal expression was monitored in human 293 cells (Graham et al., *J. Gen. Virol.* 36:59–72, 1977) exposed to virus in culture (this cell line is permissive for adenoviral replication). Cells were trypsinised 1 day prior to assay and seeded at 400 μl per well in a 24 well microliter plate using a $1 \times 10^6$/ml cell suspension. Having established a monolayer by 24 h, 10 μl of reaction mixture was added to each of 4 replicate wells containing 293 cells. The cells were incubated overnight in a fully humidified atmosphere of 5% $CO_2$ in air at 37° C. to express β-gal.

The cell monolayer was depleted of medium and then washed with PBS. Then 60 μl of lysis buffer (15% triton X-100, 250 mM Tris-HCl, pH 7.0) was added and the microliter plate incubated at room temperature for 30 min in an orbital shaker. After the cells had lysed for 30 min 50 μl of each sample was transferred to a fresh microliter plate. A set of β-gal standards (5.5 units in lysis buffer and doubling dilutions in lysis buffer) was added to the same microliter plate. 150 μl of CPRG substrate buffer (1.6 mM CPRG, 60 mM phosphate buffer: 1 mM $MgSO_4$; 10 mM KCl; 50 mM β-mercaptoethanol; 250 ml distilled water) was added to each well. After brief mixing (4 min) the plate was read at 555 nm on a microliter plate reader (Titertek Multiskan Plus MKII, ICN, flow Laboratories, Switzerland).

Figure 4:
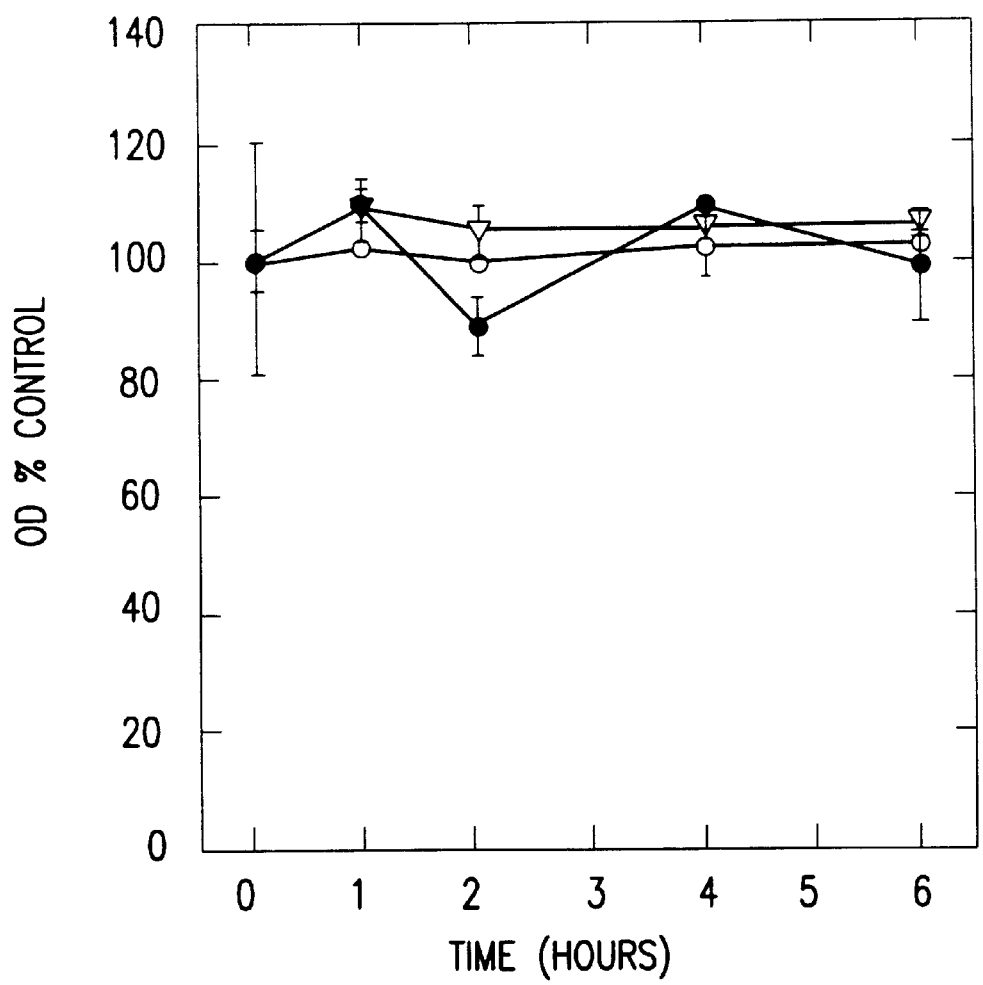
FIG. 4 depicts infectivity (CPRG) assay results for a single addition of 3% TMPEG, 3% MPEG and control virus exposed for 0–6 h.
Figure 5A:
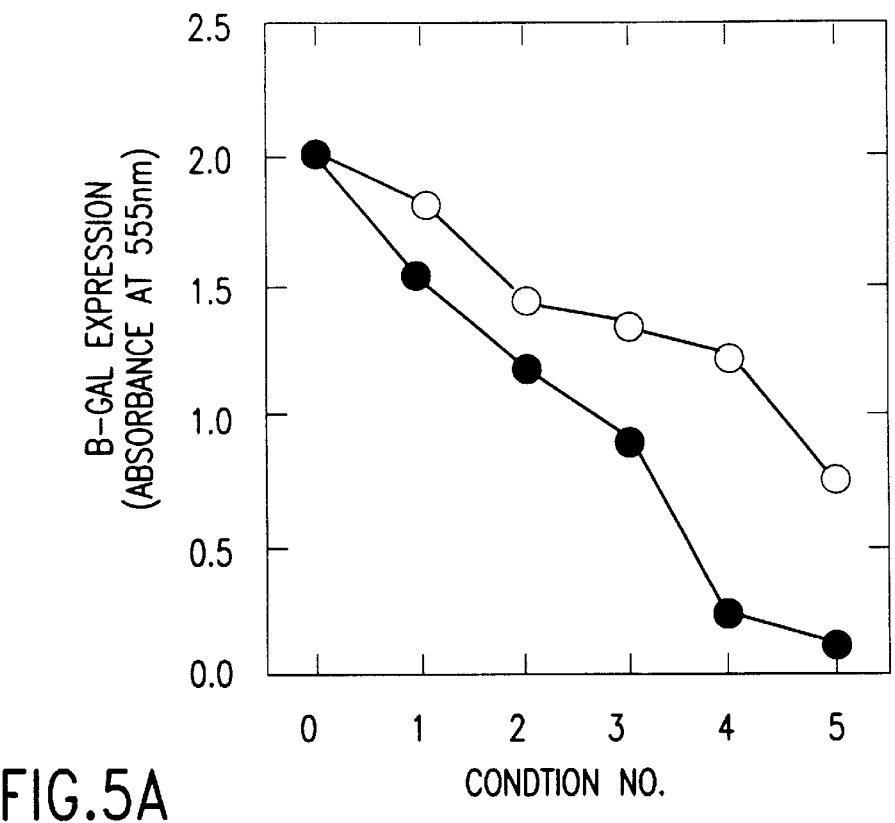
FIGS. 5A–E depicts infectivity (CPRG) assay results for stepwise additions of 5% $PEG_{5000}$, $PEG_{12000}$, or $PEG_{20000}$.
Figure 5B:
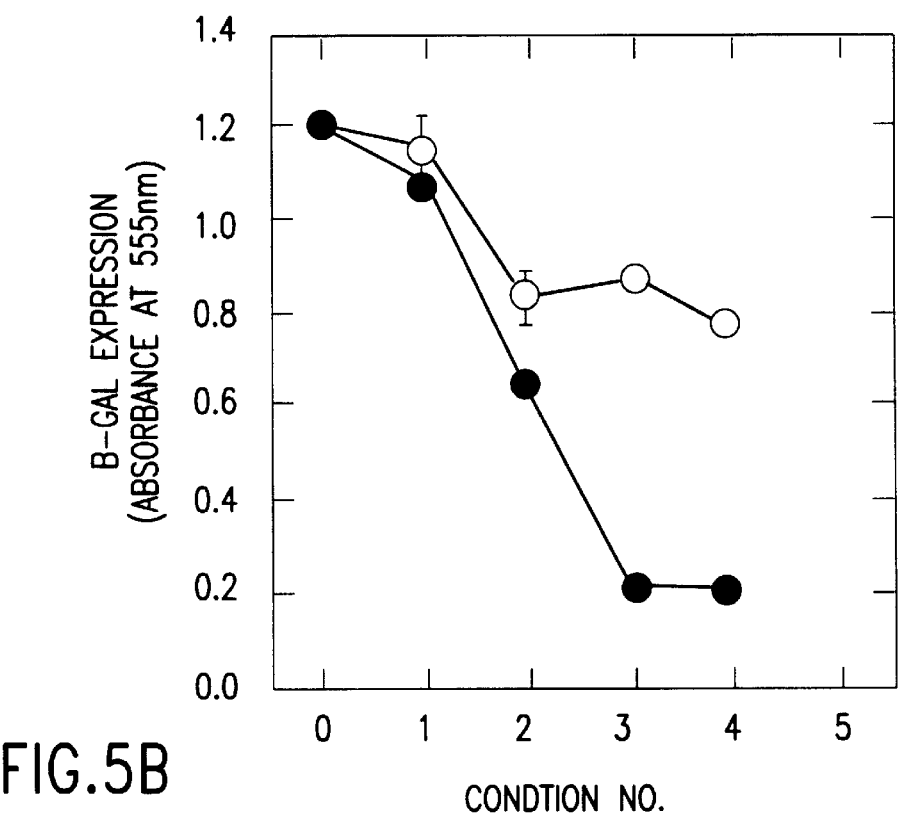
Figure 5C:
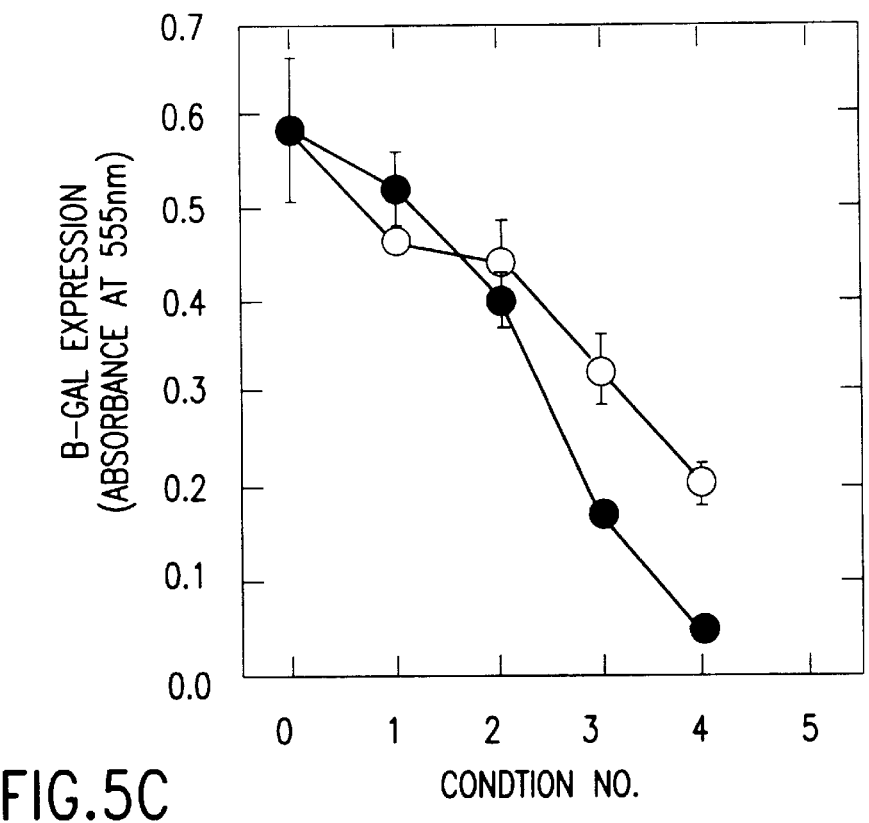
Figure 5D:
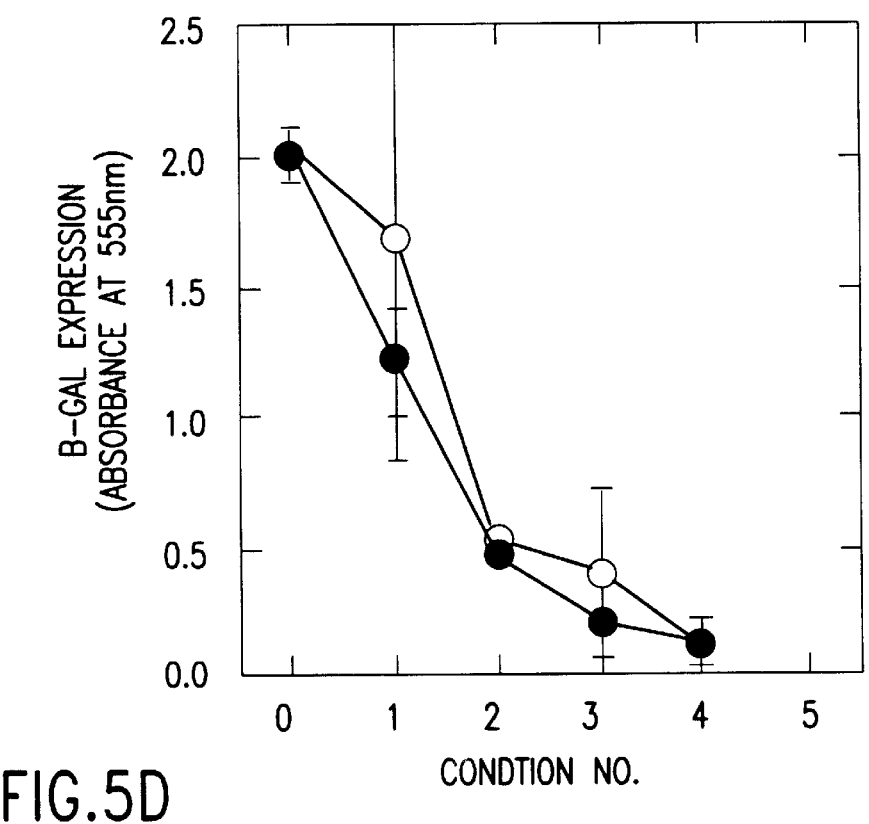
Figure 5E:
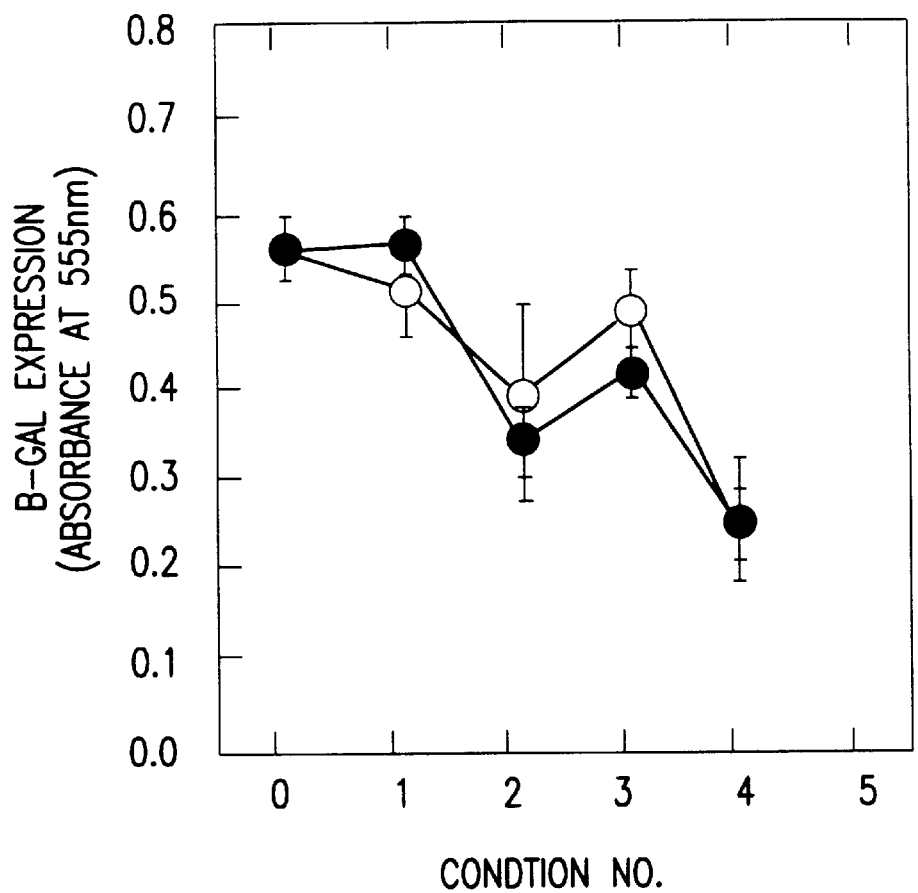

The single addition of 3% (w/v) TMPEG was examined using the CPRG assay. FIG. 4 shows the results of CPRG assays on TMPEG treated virus (open circles) and MPEG sham-treated virus (triangles) and control virus (filled circles). None of the treatments produced a trend of falling infectivity over the time period studied (six hours). A second independent experiment confirmed this result, showing no significant decline in OD over 6 hours for either control virus, TMPEG treated virus or virus sham-treated with MPEG (data not shown). Thus the PEG treatment of virus in Examples 1 and 2 demonstrated no reduction in infectivity.

The stepwise addition of 5% of $PEG_{5000}$, $PEG_{12000}$ or $PEG_{20000}$ produced a variable impact on infectivity (FIG. 5). Panels A and B show the impact of stepwise addition of 5% of $PEG_{5000}$ (mean of 2 and mean ±SD of 4 replicates respectively, some error bars are hidden by the symbols). The TMPEG (filled circles) produced a reduction in infectivity as compared to the MPEG (open circles). With $PEG_{12000}$ (panels C and D, same symbols), in one experiment TMPEG decreased the infectivity of the virus as compared with the MPEG treated virus, but in the other, MPEG and TMPEG were not significantly different (i.e. MPEG and TMPEG had a similar effect on infectivity). Treatment with $TMPEG_{20000}$ also did not show any significantly greater effect than the equivalent amount of $MPEG_{2000}$ (Panel E same symbols).

Example 4
Infectivity Assays for PEGylated and SHAM Treated Virus

Single and stepwise additions of TMPEG and MPEG were prepared as in Example 3 and analyzed with respect to infectivity using a chemiluminesent reporter assay system for the detection of the virally encoded β-galactosidase (Galacto-Light™). This assay system uses a chemiluminescent substrate and was performed in accordance with the manufacturer's instructions.

Figure 6A:
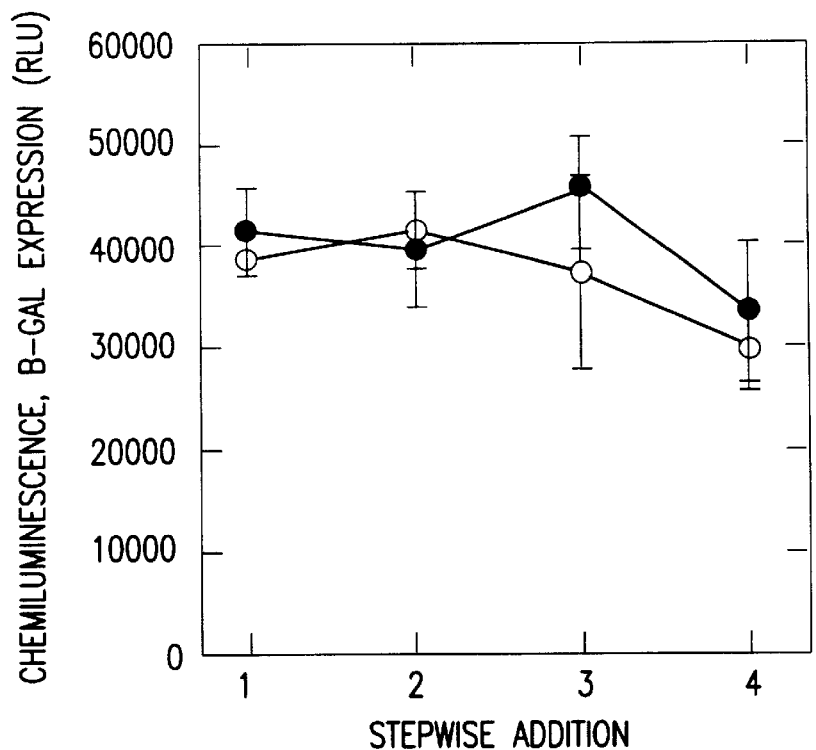
FIGS. 6A–C depicts infectivity (chemiluminescence, RLU) assay results for stepwise additions of 3%, 5% or 8% $PEG_{5000}$.
Figure 6B:
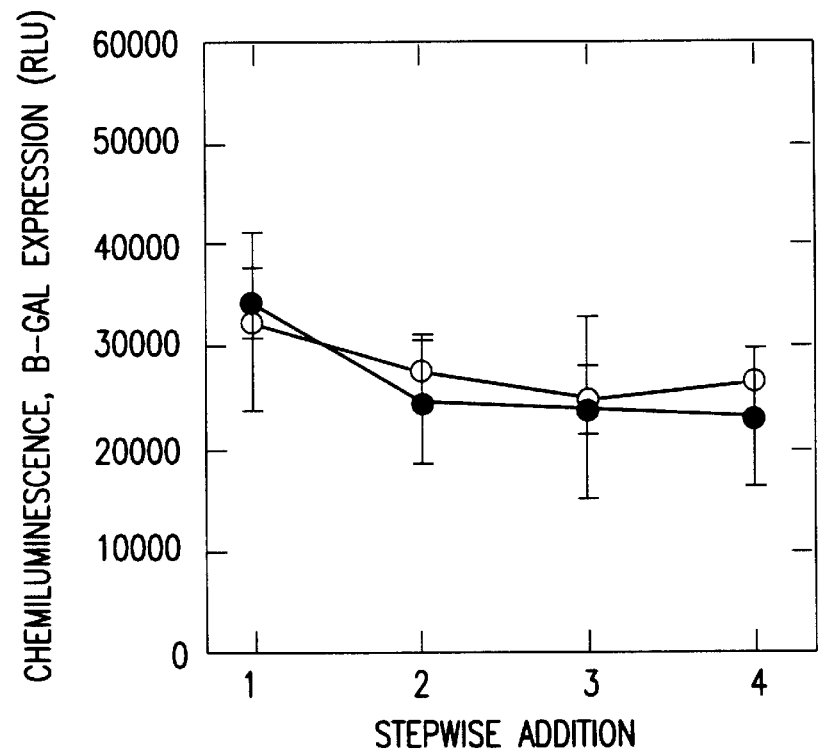
Figure 6C:
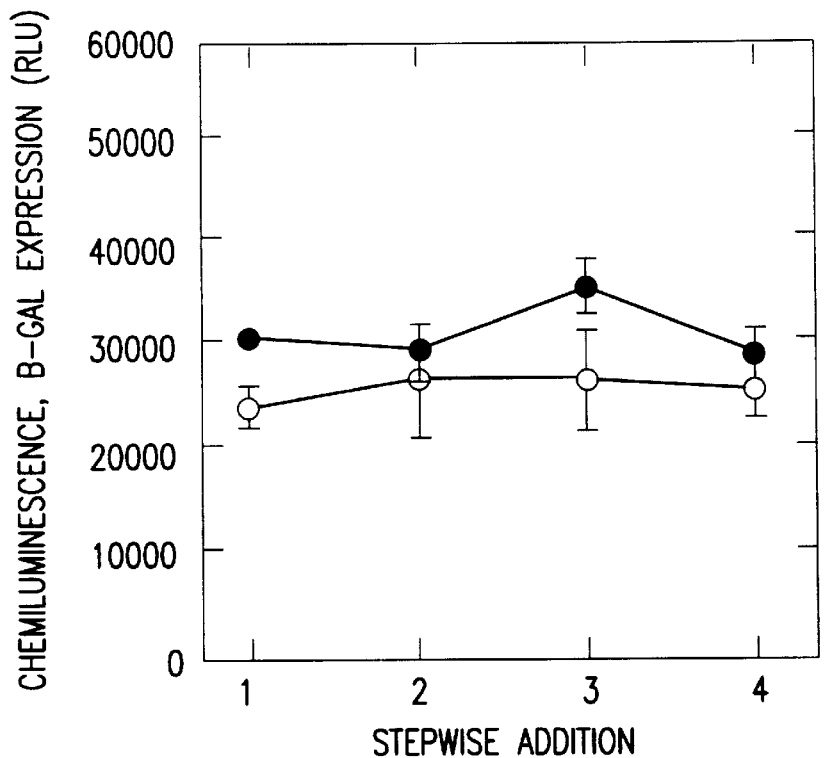

FIGS. 6a–c compares the effects of 3%, 5% and 8% incremental additions of $TMPEG_{5000}$ (filled circles) or $MPEG_{5000}$ (open circles) on viral infectivity. Note that in FIGS. 6a and b the MPEG and TMPEG treated viral samples show similar infectivity. A modest decline in infectivity with treatment with either MPEG or TMPEG was observed. In subsequent experiments with no-PEG controls these showed a similar decline in infectivity, suggesting that this was a handling effect and not due to PEG. In FIG. 6c the MPEG and the TMPEG treated virus performed similarly. Thus, this experiment shows that treatment with TMPEG or MPEG does not result in loss of infectivity.

Figure 7A:
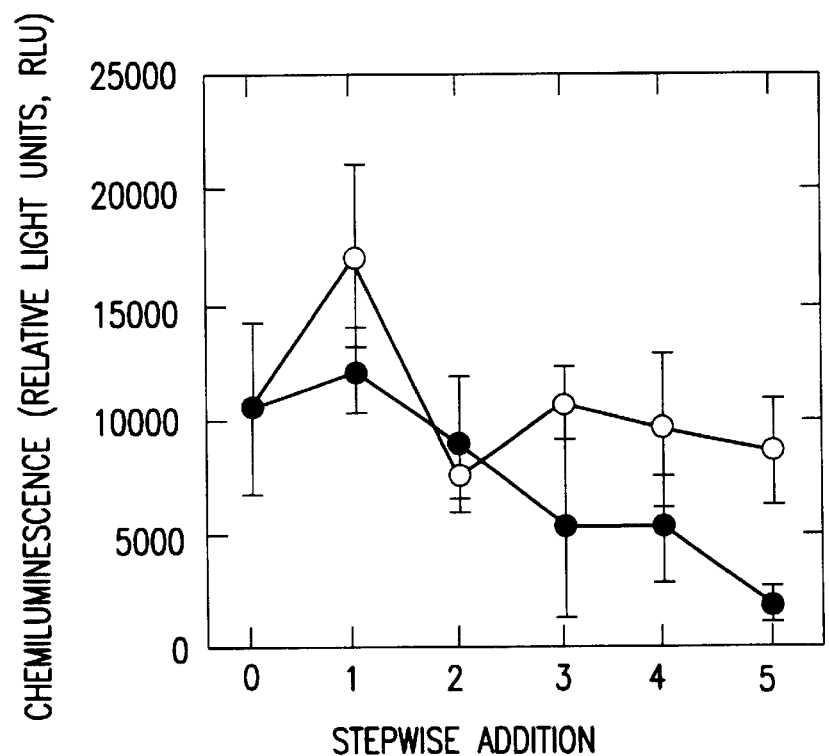
FIGS. 7A–C depicts infectivity (chemiluminescence, RLU) assay results for stepwise additions of 5% $PEG_{5000}$.
Figure 7B:
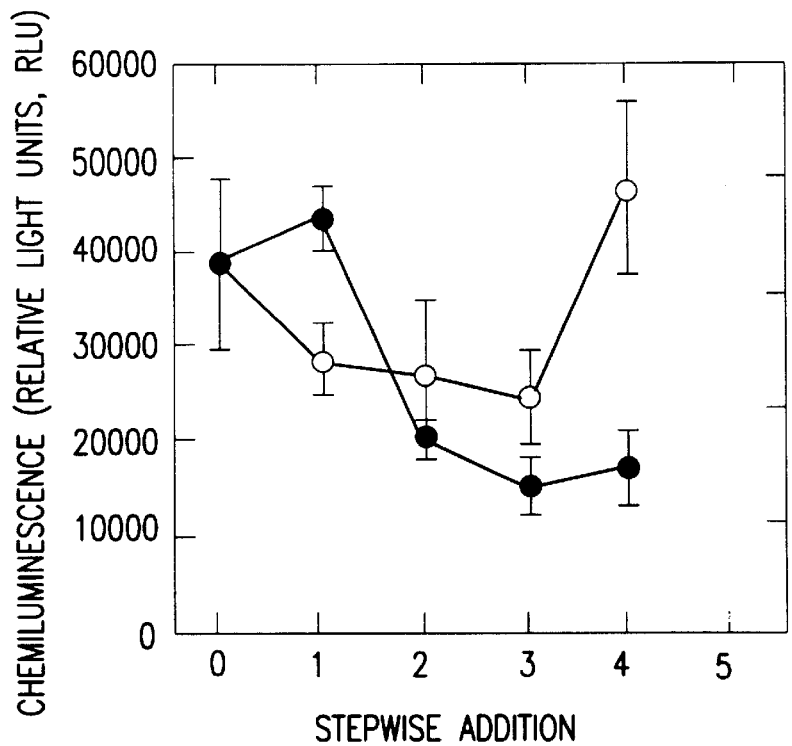
Figure 7C:
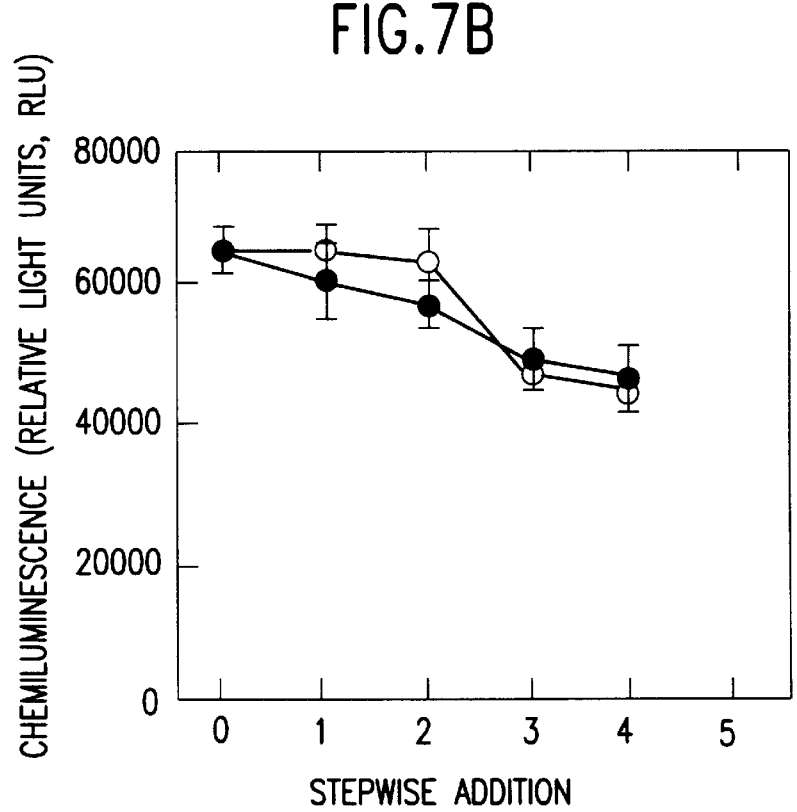

Apparent loss of infectivity due to the addition of PEG chains was seen twice with this assay in experiments using $PEG_{5000}$ in the 5% incremental addition scheme (FIGS. 7a and b, filled circles TMPEG-open circles MPEG). A subsequent assay of the same sample as shown in FIG. 7b showed no significant difference between the MPEG and TMPEG treatments, indicating that no significant loss of infectivity had in fact occurred (FIG. 7c, same symbols).

Figure 8A:
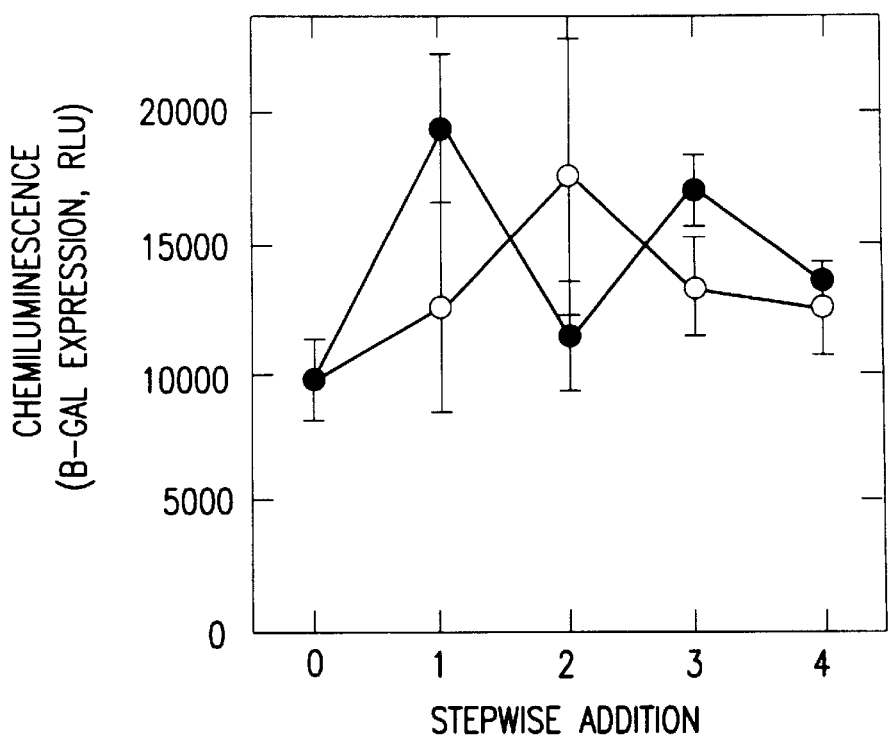
FIGS. 8A–C depicts infectivity (chemiluminescence, RLU) assay results for stepwise additions of 5% $PEG_{12000}$ and $PEG_{20000}$.
Figure 8B:
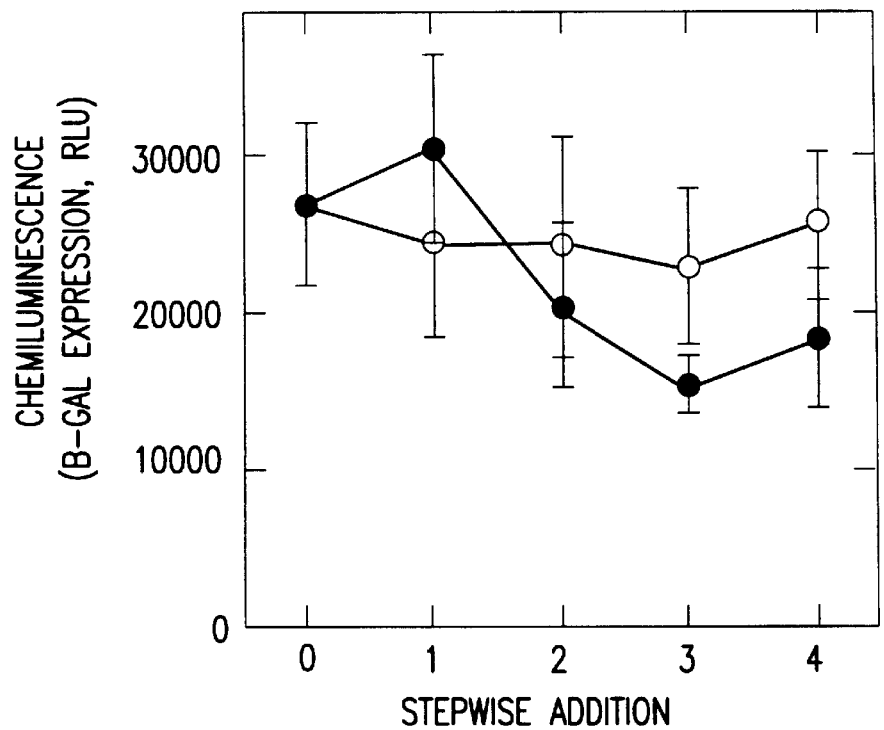
Figure 8C:
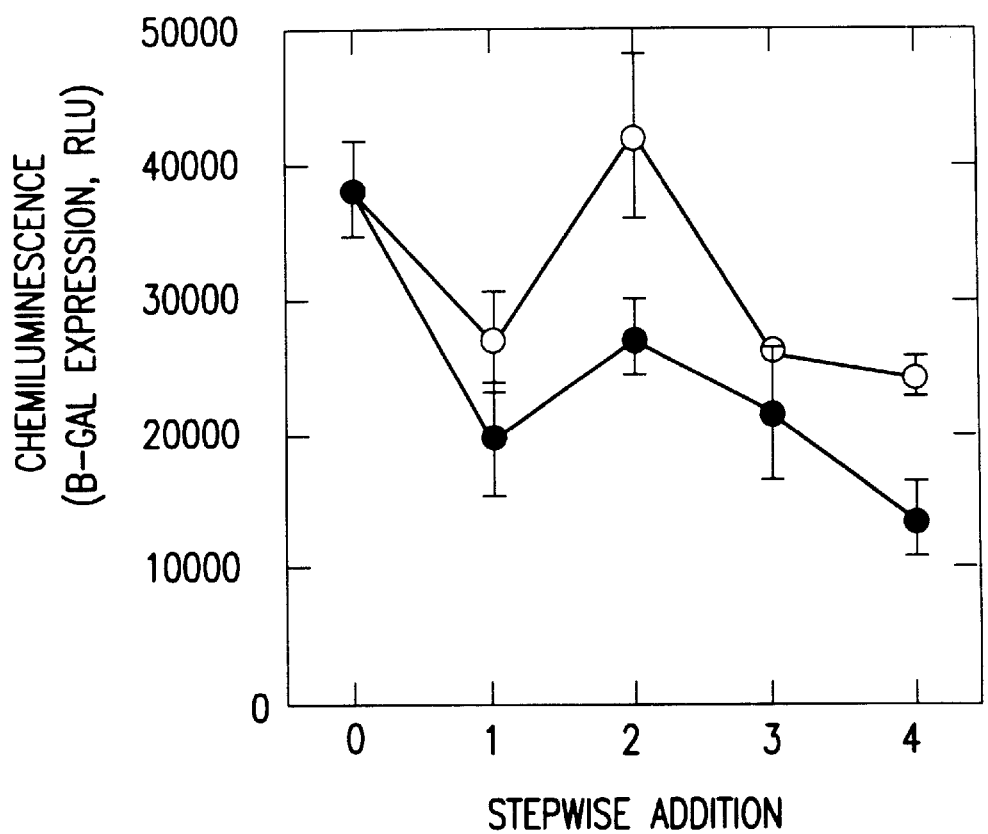

FIG. 8 shows comparable results for $PEG_{12000}$ (panels A and B, filled circles TMPEG; open circles MPEG) and $PEG_{20000}$ (panel C, same symbols). As above, condition 0 is an untreated virus control and conditions 1–4 are stepwise additions of 5% TMPEG or MPEG. With the $PEG_{12000}$ there was a modest additional loss of infectivity with TMPEG in one of the two experiments after the 3rd and 4th addition of TMPEG (panel B). In the other experiment (Panel A) using $PEG_{12000}$ no significant reduction in infectivity was observed with either TMPEG or MPEG. With $PEG_{20000}$, TMPEG treatment produced lower infectivity than MPEG for all additions including the first, but approximately one third the initial infectivity value remained even after the 4th addition of TMPEG.

Figure 9:
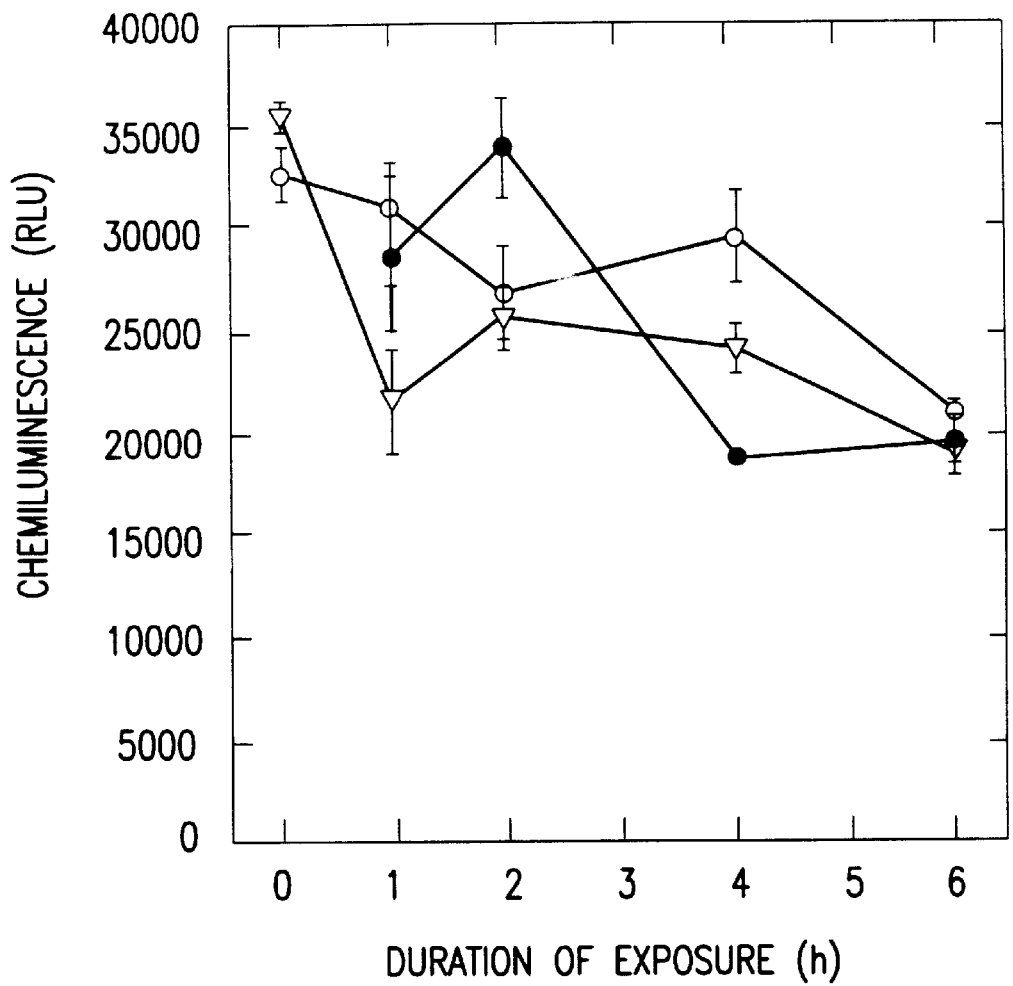
FIG. 9 depicts infectivity (chemiluminescence, RLU) assay results for a single addition of 3% $PEG_{5000}$.

With a single addition of 3% $PEG_{5000}$, i.e. prepared as in Example 3, with the chemiluminescence assay there was a modest decline in infectivity (FIG. 9). It should be noted that the decline in infectivity observed over time was seen both in the case of the TMPEG (filled circles) and MPEG treated virus (open circles) as well as the untreated "handling" control (triangles).

Example 5
The Impact of PEGylation on the Reduction of Infectivity by Neutralizing Antibodies Using the infectivity assay given in Example 4, exposure of the TMPEG and MPEG treated virus to neutralizing antibodies was used to seek evidence of the protection from neutralization afford by the polymer treatment.

Transgene expression was monitored in the presence and absence of a polyclonal neutralizing antibody purified from rabbit anti-hexon serum using a hexon affinity resin. The polyclonal antibody was titered with untreated virus and the ratio was established where 30 to 50% infectivity was retained in the presence of the neutralizing antibody. Two antibody titers were used 10,000:1 (~30%) or 5,000:1 (~40–50%) (antibody molecules to virus particles) where indicated.

Figure 10A:
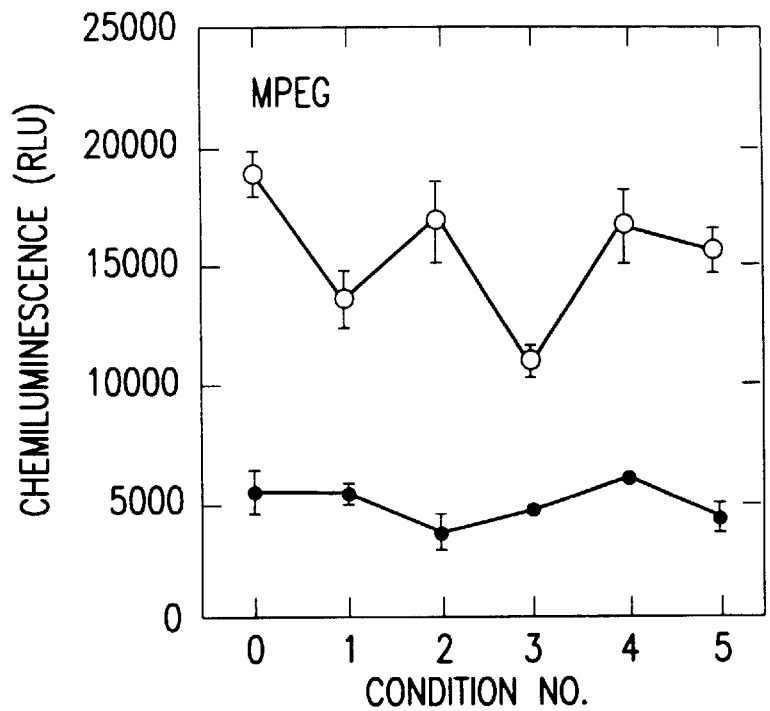
FIGS. 10A and B shows graphs of an antibody neutralization assay for the impact of stepwise additions of 5% $PEG_{5000}$ on neutralization of infectivity (chemiluminescence, RLU assay), 10,000:1 antibody molecules to virus particles.
Figure 10B:
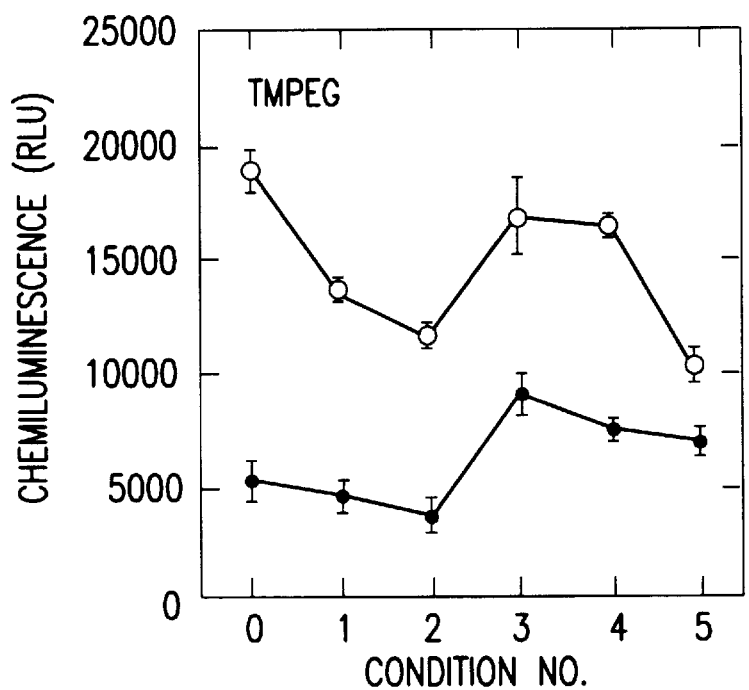
FIG. 10C is a bar graph showing the impact of stepwise additions of 5% $PEG_{5000}$ on transgene expression. The open bars show MPEG treatment and the hatched bars show TMPEG treatment.
Figure 10C:
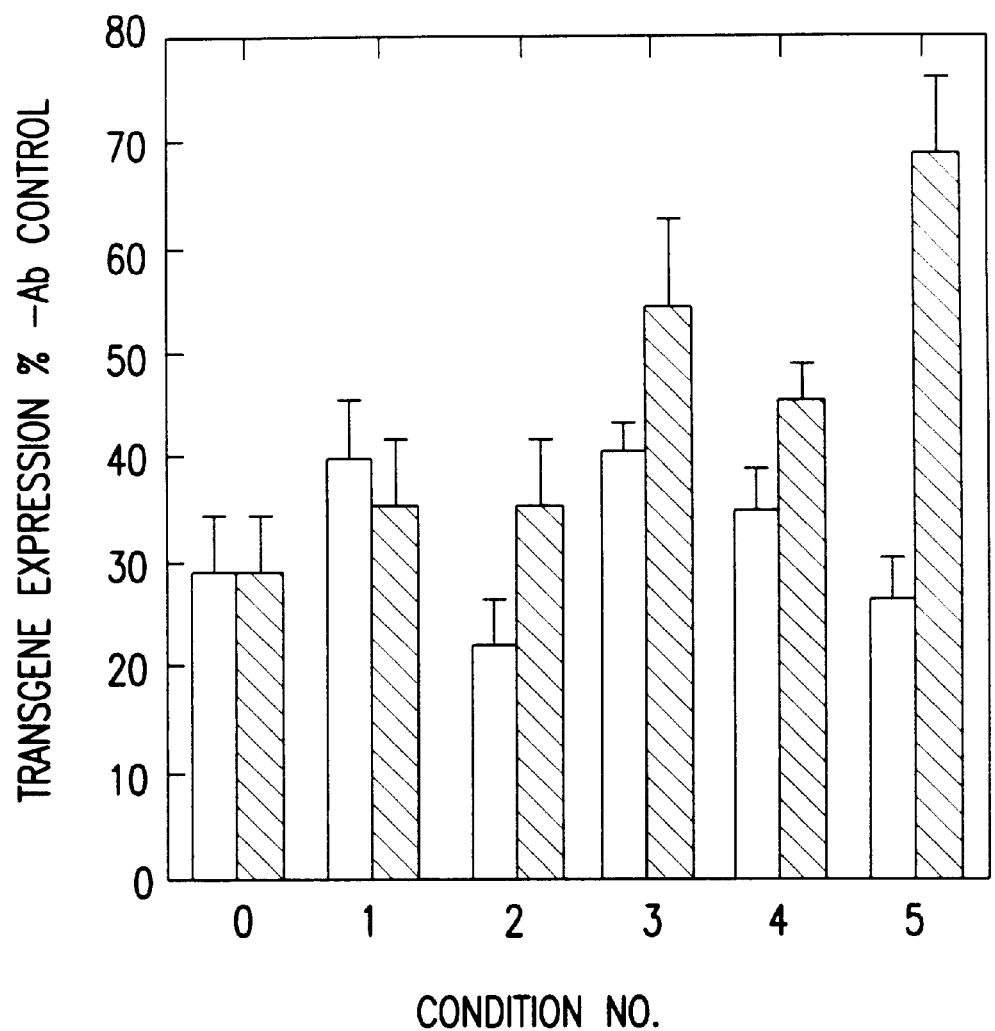
Figure 11A:
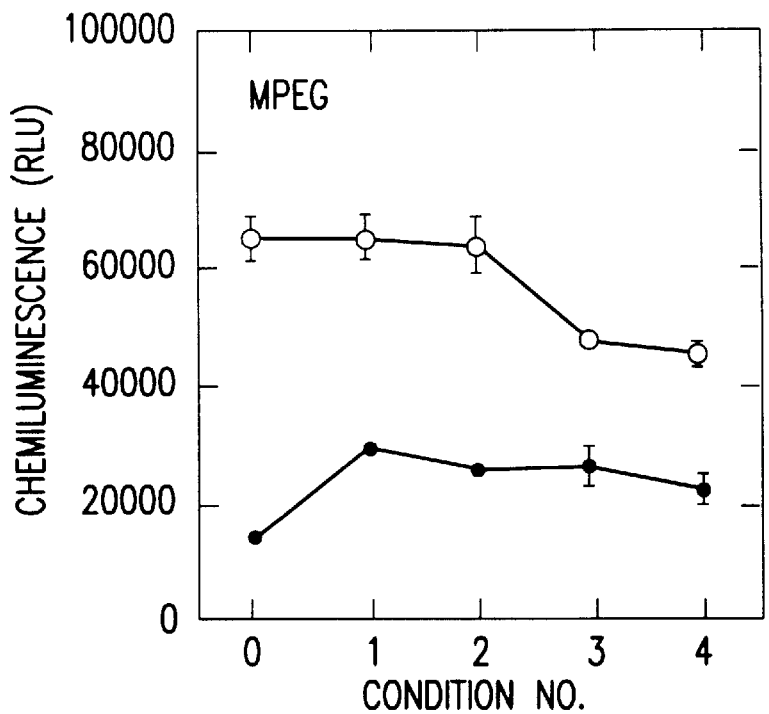
FIGS. 11A and B shows graphs of antibody neutralization assays for the impact of stepwise additions of 5% $PEG_{5000}$ on neutralization of infectivity (chemiluminescence RLU assay); 5,000:1 antibody molecules to virus particles.
Figure 11B:
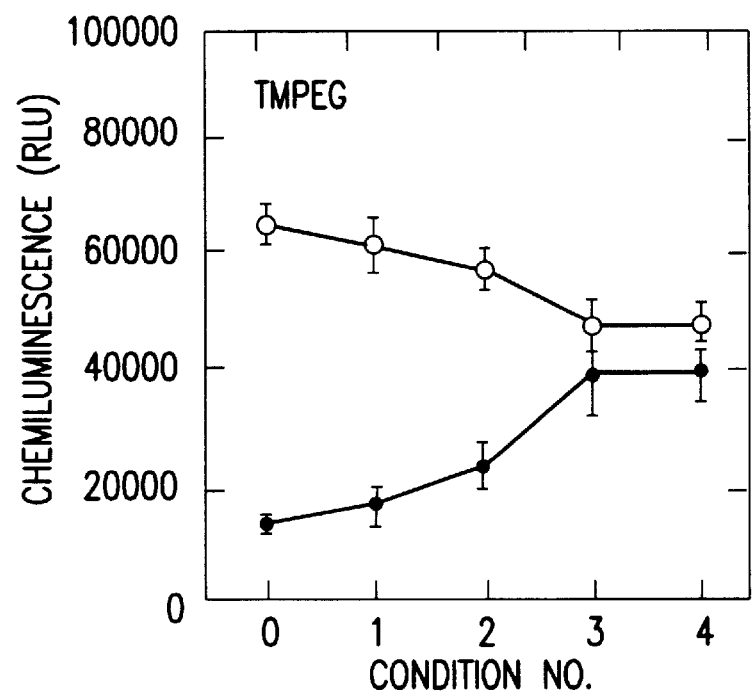
FIG. 11C is a bar graph showing the impact of stepwise additions of 5% $PEG_{5000}$ on transgene expression. The open bars show MPEG treatment and the hatched bars show TMPEG treatment.
Figure 11C:
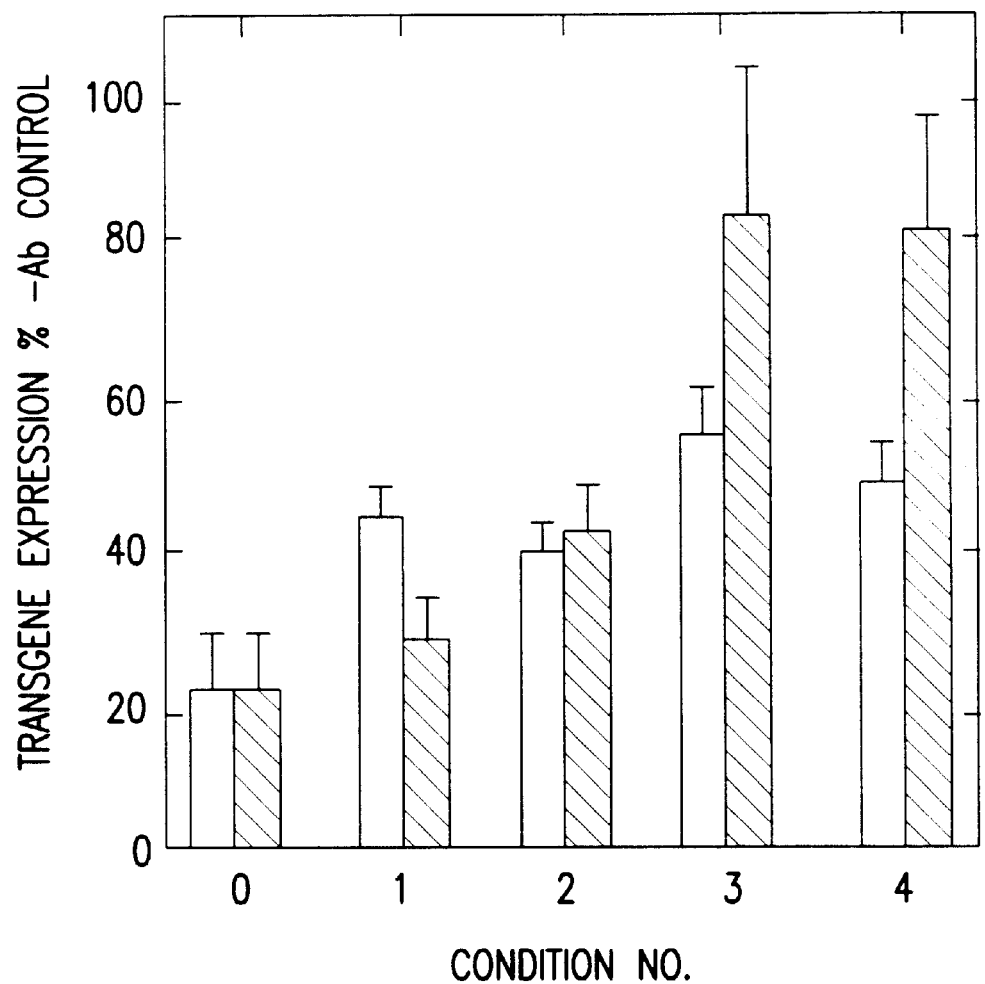
Figure 12A:
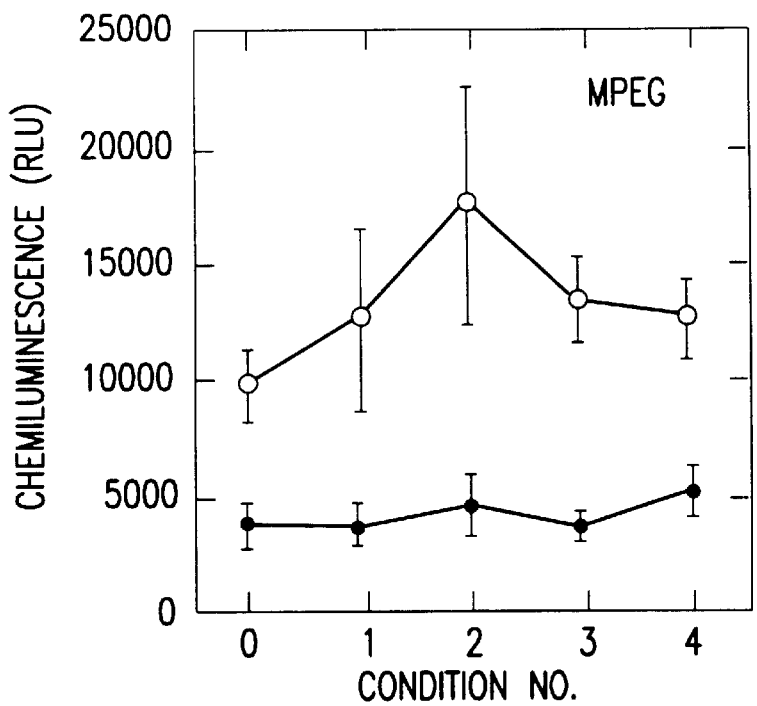
FIGS. 12A and B shows graphs of an antibody neutralization assay for the impact of stepwise additions of 5% $PEG_{12000}$ on neutralization of infectivity (chemiluminescence RLU assay); 10,000:1 antibody molecules to virus particles.
Figure 12B:
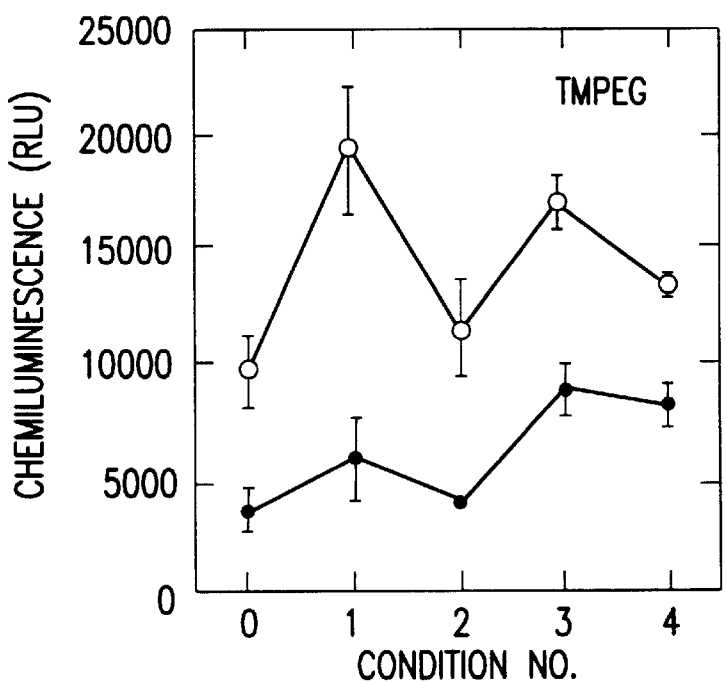
FIG. 12C is a bar graph showing the impact of stepwise additions of 5% $PEG_{12000}$ on transgene expression. The open bars show MPEG treatment and the hatched bars show TMPEG treatment.
Figure 12C:
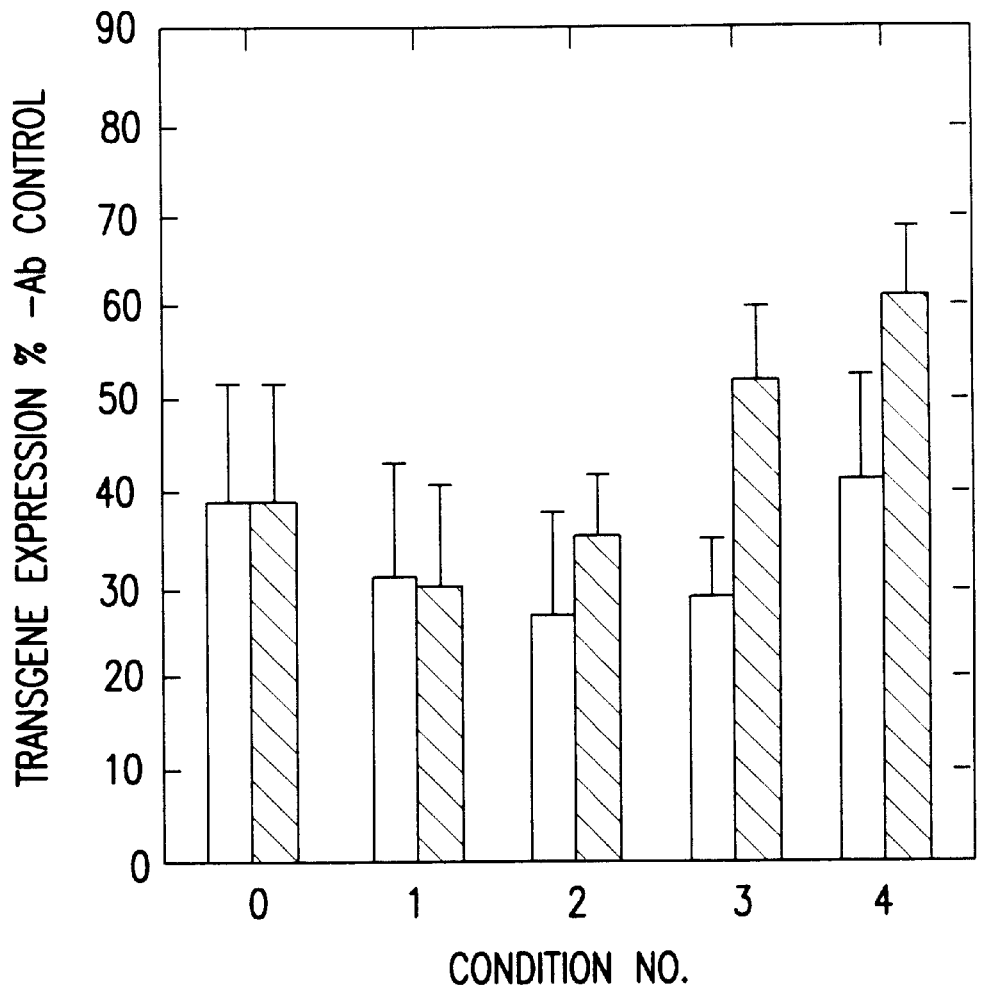

FIGS. 10–12 show the impact of incremental additions of 5% $TMPEG_{5000}$ (FIGS. 10 and 11) and $TMPEG_{12000}$ (FIG. 12) on antibody neutralisation. Antibody treatment is shown by the filled symbols and MPEG treatment by circles and TMPEG treatment by squares. In the lower panels, hatched bars indicate TMPEG treatment.

In all three cases there is evidence of significant protection from neutralization and a trend of improving protection with the highest/longest TMPEG exposure giving maximum protection. The upper panels in each figure show the raw data and the lower panels the transgene expression as a percent of the equivalent non-antibody treated control. In FIG. 10 the amount of virus added to the assay was adjusted to compensate for differences in the number of infectious units of the non-antibody treated controls. In FIGS. 11 and 12 the same number of viral particles was assayed for each condition. The antibody titers were 10,000:1, 5,000:1 and 10,000:1 respectively.

These data show protection from immune recognition. For the purposes of clarification, protection is defined as there being a statistically significant difference in transgene expression in the presence of the immune agent under test (e.g. antibody or cell suspension) as compared with the expression observed in untreated control.

The single addition of 3% $TMPEG_{5000}$ showed some protection after 4 h and 6 h incubation in two independent assays. Taken in conjunction the above examples indicate the presence of a PEGylation "window" where treatment with PEG does not abrogate all infectivity but conveys statistically significant protection from neutralisation by antibody.

Example 6
Indirect PEGylation of Adenovirus Using a Non-neutralizing Anti-hexon Antibody The present invention relates to polymer-modified viruses, processes for obtaining them and their use. The invention also provides means of attaching polymer molecules to viral particles whilst retaining infectivity of the modified virus.

Initial experiments on the PEGylation of an anti-hexon antibody were performed using commercially available anti-hexon antibodies from Chemicon (Mab 8052). Two types of activated PEGs were tested for their ability to PEGylate the antibody namely cyanuric chloride activated PEG and PEG-tresylate (TMPEG). TMPEG$_{5000}$ was obtained from Shearwater Polymers, Huntsville, Ala.

Figure 13:
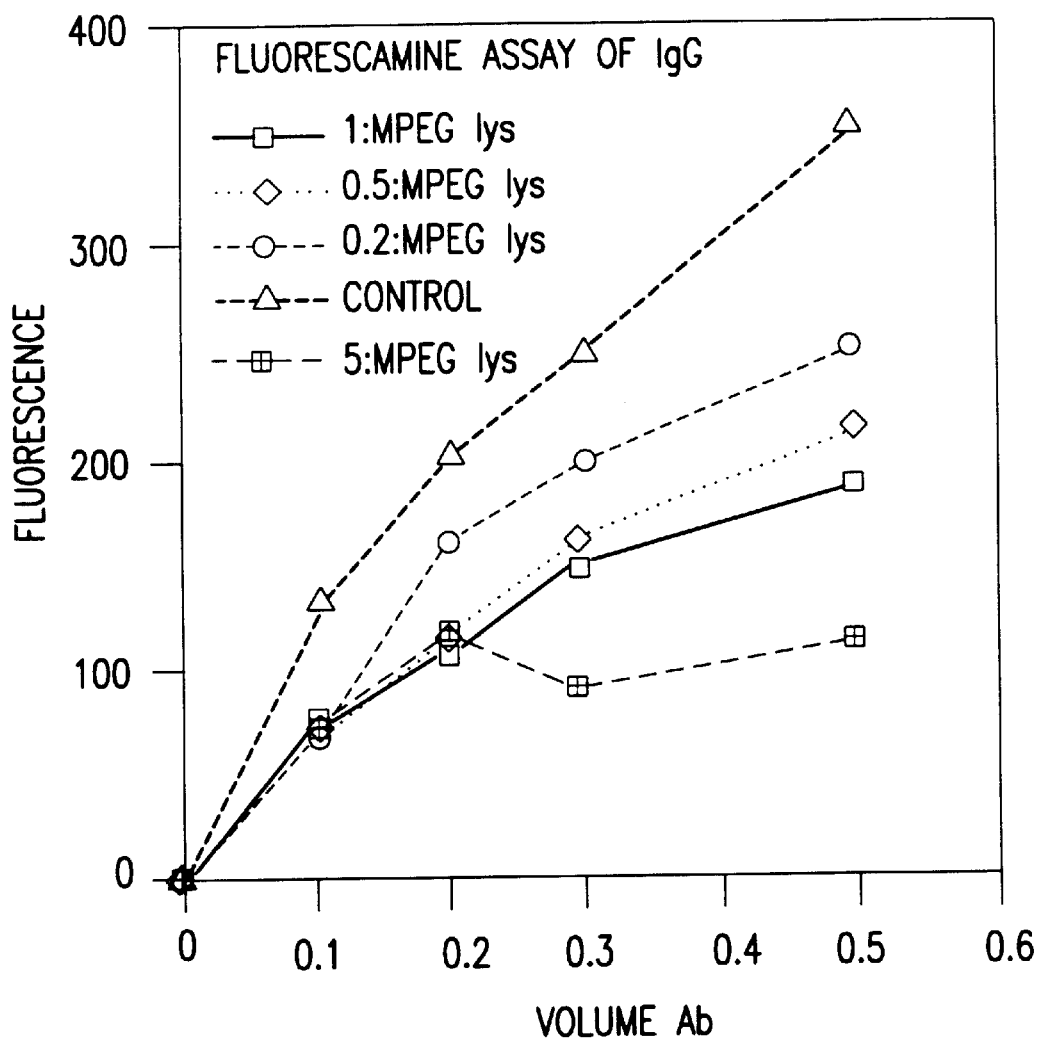
FIG. 13 shows a graph of a fluorescamine assay of anti-hexon antibody modified using TMPEG.

PEGylation of an anti-hexon antibody using TMPEG was accomplished as follows. MAb 8052 50 µg was incubated with TMPEG at the following PEG:lysine molar ratios, 0.2:1, 0.5:1, 1:1, 2:1, 5:1. The TMPEG and antibody were incubated for one hour at room temperature with gentle rocking on a "Vari-Mix" after which time the reaction mixture was stored at 4° C. or −80° C. until further use. (In some experiments the treatment with PEG was stopped using excess lysine. However, for samples analyzed by the fluorescamine assay, the reaction was stopped by lowering the temperature.) Calculation of molar ratios assumed 90 lysine residues per IgG. A fluorescamine assay of the IgG treated with TMPEG was performed according to the method of Laurel et al. (1994) *Methods in Enzymology*, 228 incorporated herein by reference, to assess the amount of lysine substitution of the anti-hexon antibody treated with TMPEG. In this assay lysine residues modified with PEG are not available for reaction with the fluorescamine leading to a corresponding decrease in antibody associated fluorescence. Results of the fluorescamine assay are provided in FIG. 13. The percent modification of IgG lysines was calculated as 1−(slope modified IgG/slope unmodified IgG) using the method of Laurel et al. Results are presented in Table 1.

TABLE 1

| PEG:Lysine | % Modification lysines |
|---|---|
| Control | 0 |
| 0.2:1 | 25 |
| 0.5:1 | 37 |
| 1:1 | 46 |
| 5:1 | 70 |

It is concluded that increasing the ratio of PEG:lysine leads to a corresponding increase in the number of lysine residues that are substituted with PEG or alternatively that treatment with PEG decreases the number of available free lysine residues on the IgG.

Figure 14:
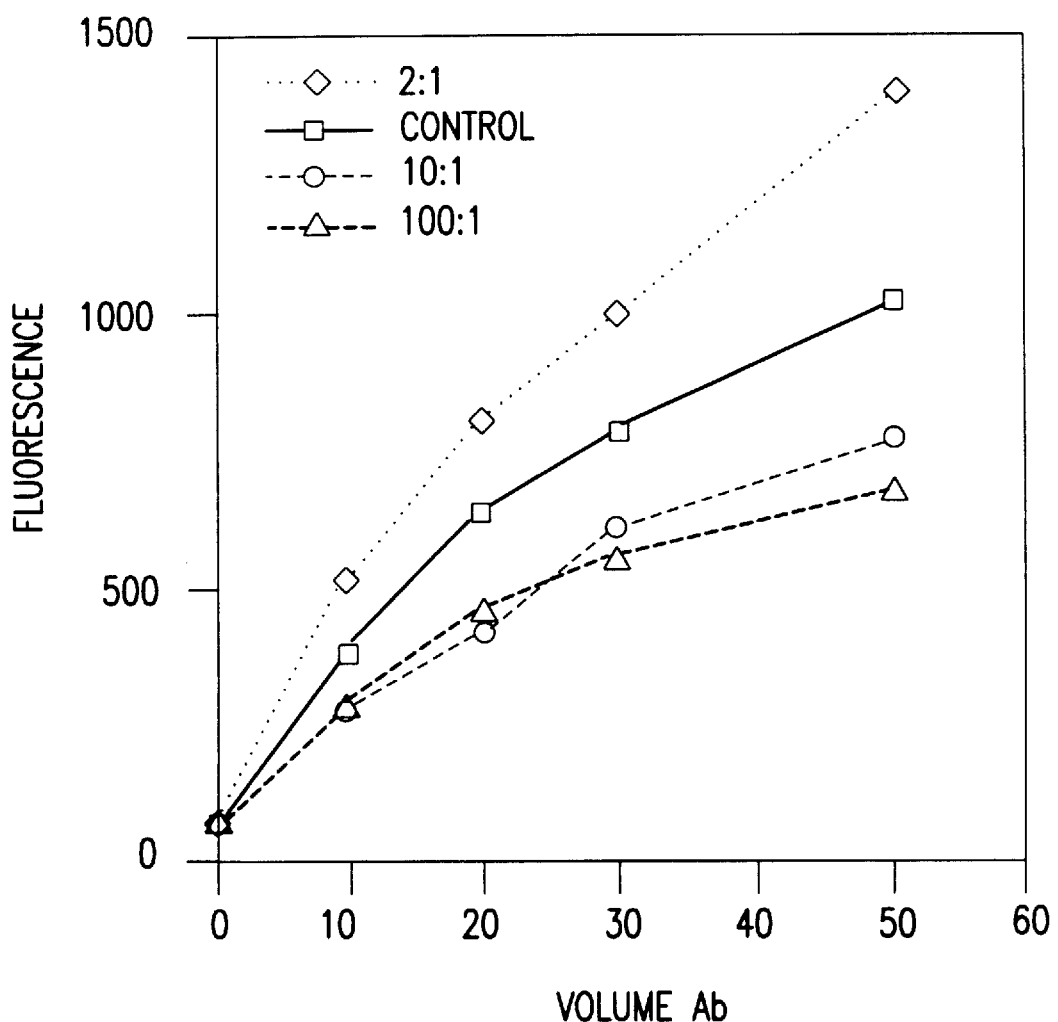
FIG. 14 shows a graph of a fluorescamine assay of MAb 8052 modified using cyanuric chloride-MPEG.

PEGylation of an anti-hexon antibody using cyanuric chloride activated PEG was accomplished as follows. Anti-hexon antibody MAb 8052 was dialyzed into 0.1 M sodium bicarbonate pH 9. Following dialysis 25 µg of the MAb 8052 was incubated with the cyanuric chloride activated MPEG at increasing PEG:lysine residues of 2:1, 10:1, 100:1. The PEG and antibody were incubated for one hour at room temperature with gentle rocking on a "Vari-Mix" after which time the reaction mixture was stored at 40C or −80° C. until further use. Calculation of molar ratios assumed 90 lysine residues per IgG. To assess the amount of lysine substitution of the PEGylated anti-hexon antibody, a fluorescamine assay of the PEG-treated IgG was performed according to the method of Laurel et al. (1994), *Methods in Enzymology* 228. Results of the fluorescamine assay are provided in FIG. 14.

The percent modification of IgG lysines was calculated as 1−(slope modified IgG/slope unmodified IgG) using the method of Laurel et al. Results are presented in Table 2.

TABLE 2

| PEG:IgG Lysine | % modification of lysines |
|---|---|
| Control | 0 |
| 2:1 | 30 |
| 10:1 | 47 |
| 100:1 | 60 |

It is concluded that the anti-hexon antibody Mab 8502 was successfully PEGylated using cyanuric chloride activated mPEG. Using the fluorescamine assay it was shown that increasing the ratio of PEG:lysine during the PEGylation reaction resulted in a corresponding increase in the modification of lysine residues on the antibody.

Example 7

Demonstration that a PEGylated Anti-hexon Antibody Still Recognizes Viral Hexon

Figure 15:
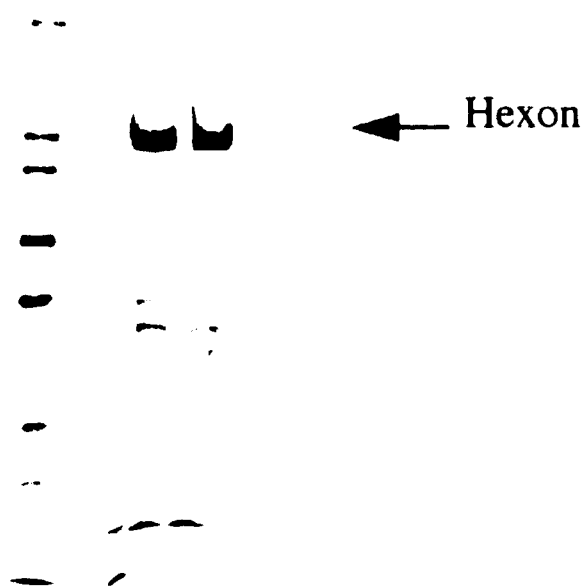
FIG. 15 shows an SDS-PAGE gel showing immunoprecipitation of adenoviral hexon by PEGylated anti-hexon antibody.
Figure 16A:
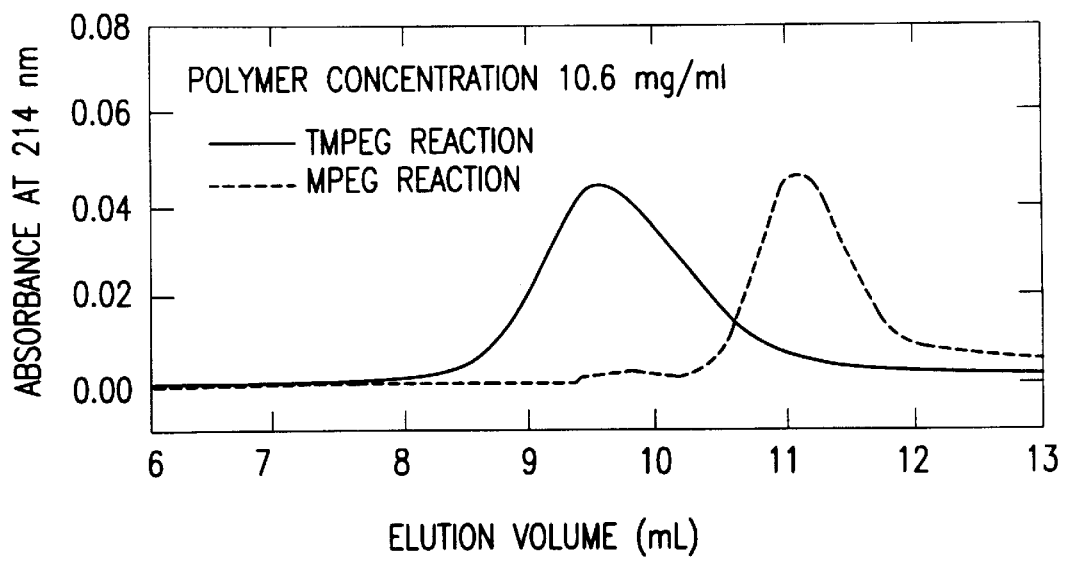
FIGS. 16A–E depicts gel permeation chromatography of antibody and PEGylated antibody on a Superose 12 column.
Figure 16B:
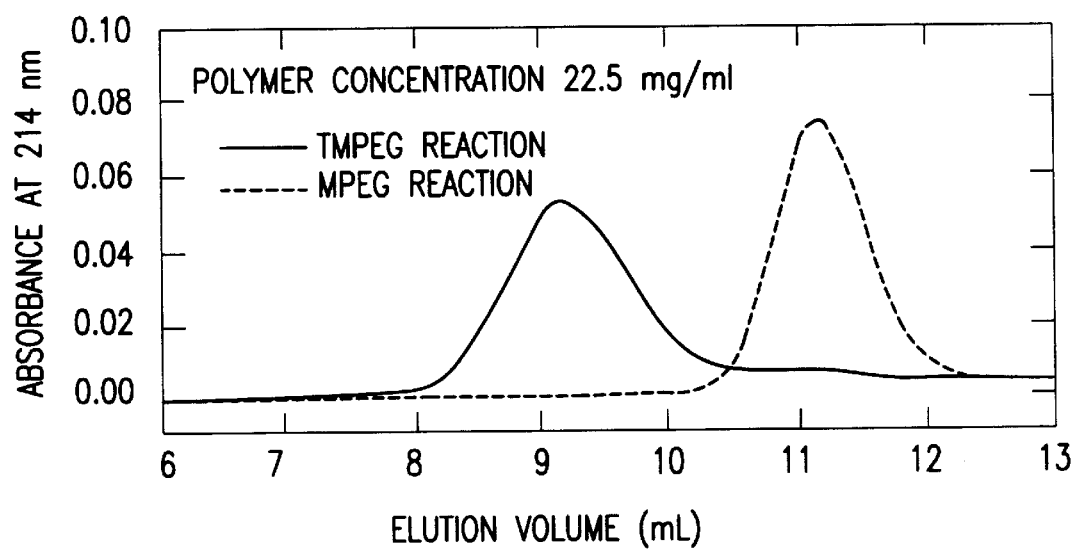
Figure 16C:
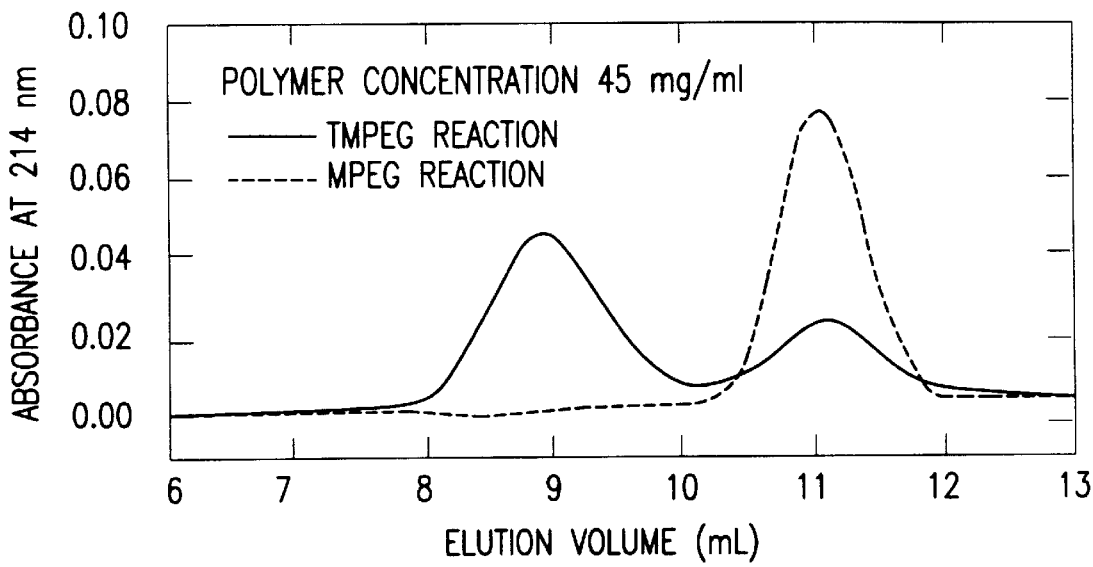
Figure 16D:
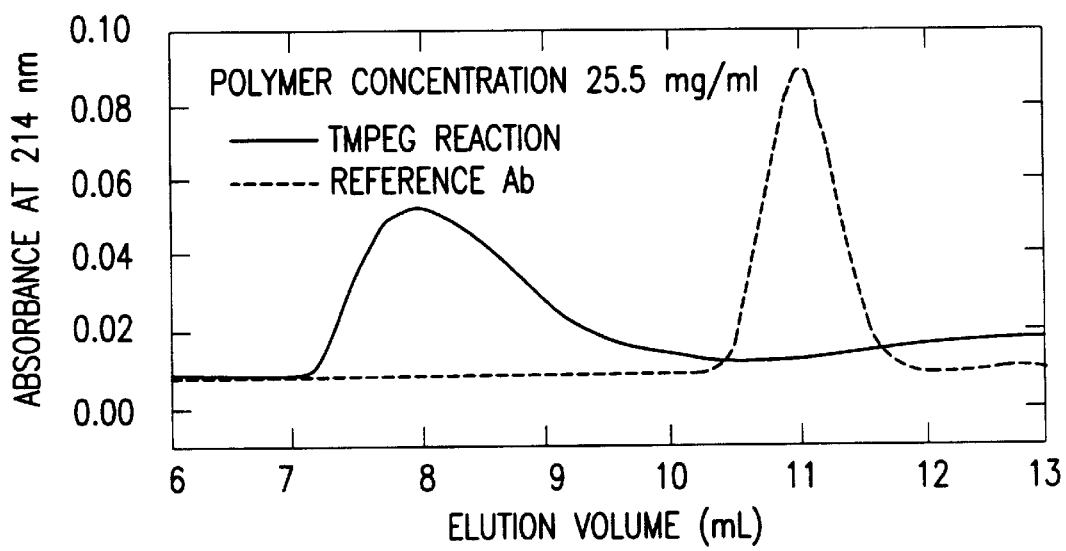
Figure 16E:
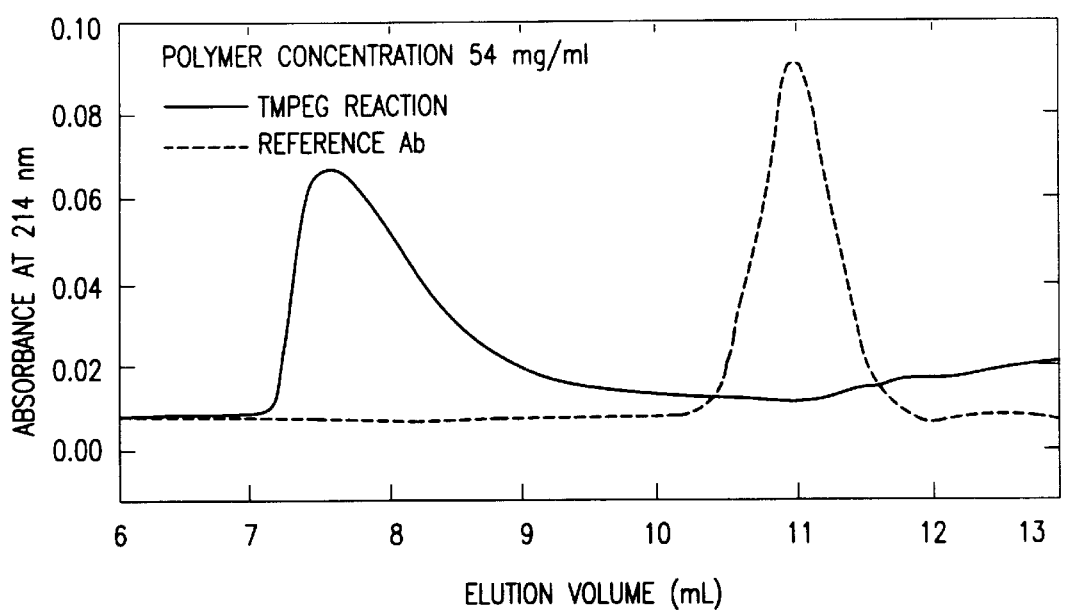
Figure 17A:
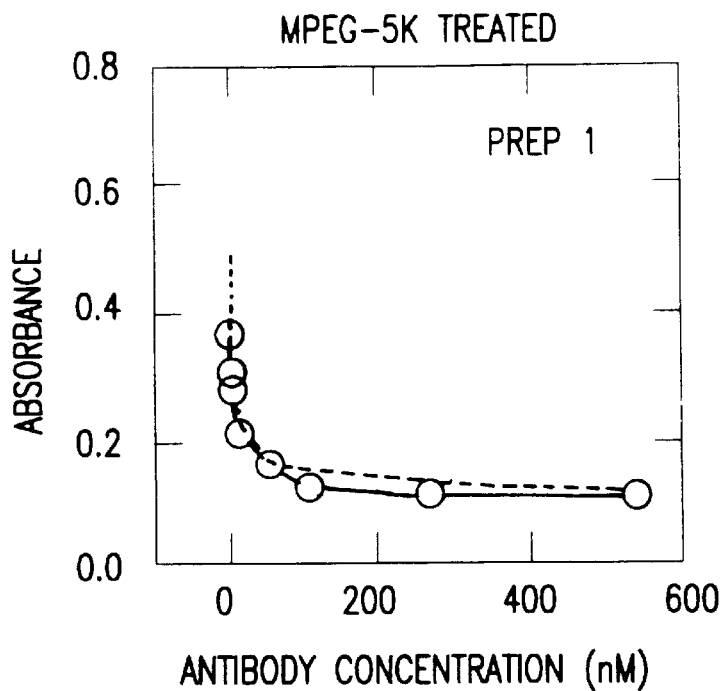
FIGS. 17A–J depicts antibody competition ELISA, showing competition of biotinylated anti-hexon antibody by binding to virus in the presence of increasing concentrations of PEG antibody.
Figure 17B:
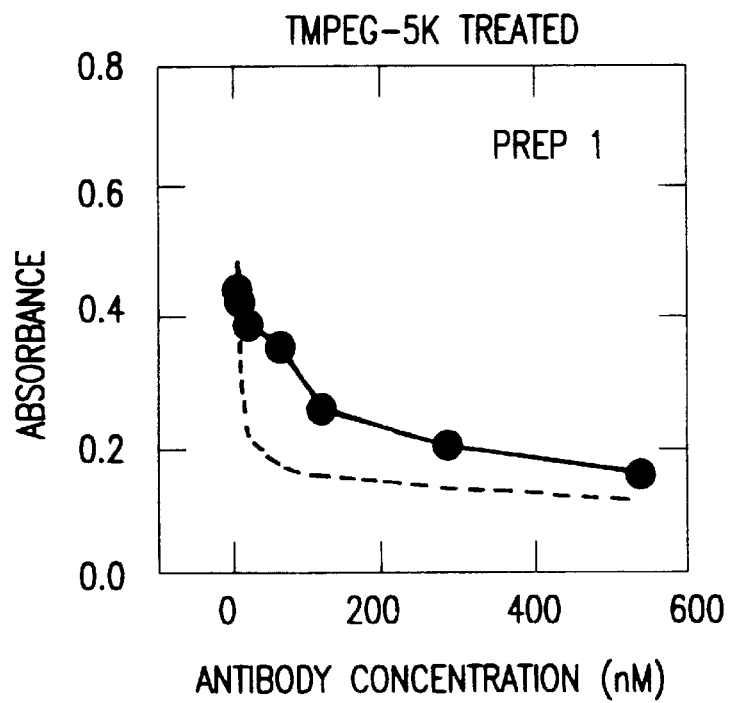
Figure 17C:
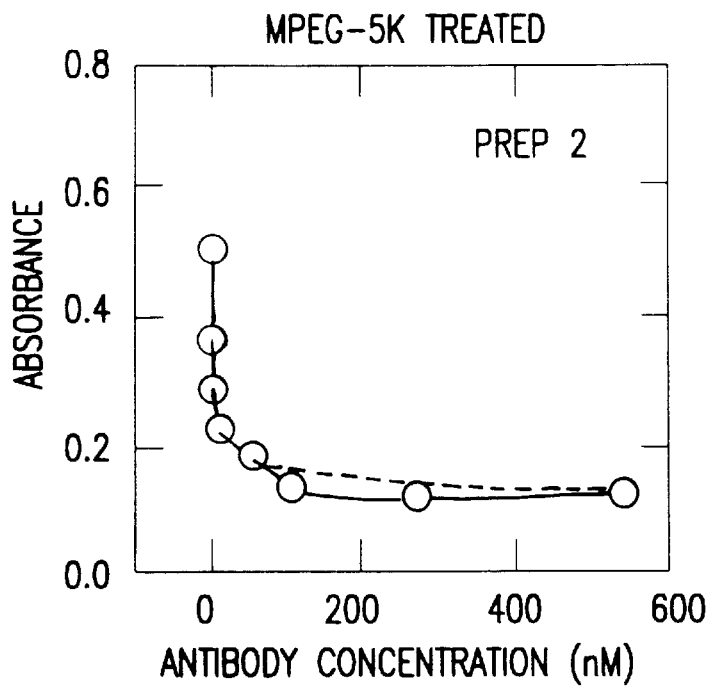
Figure 17D:
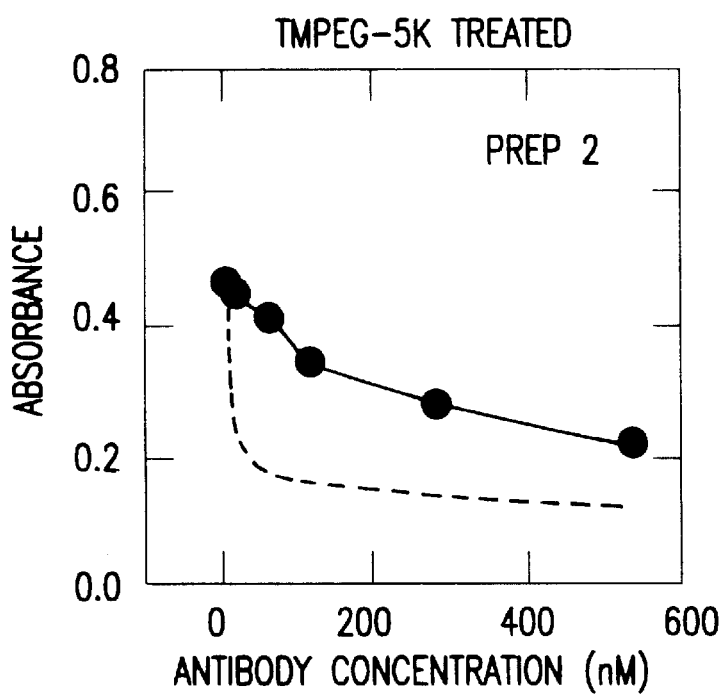
Figure 17E:
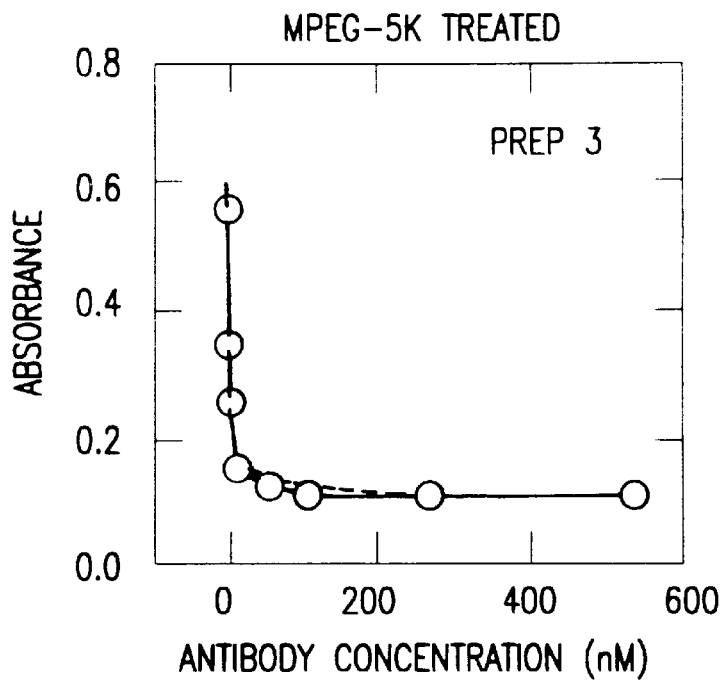
Figure 17F:
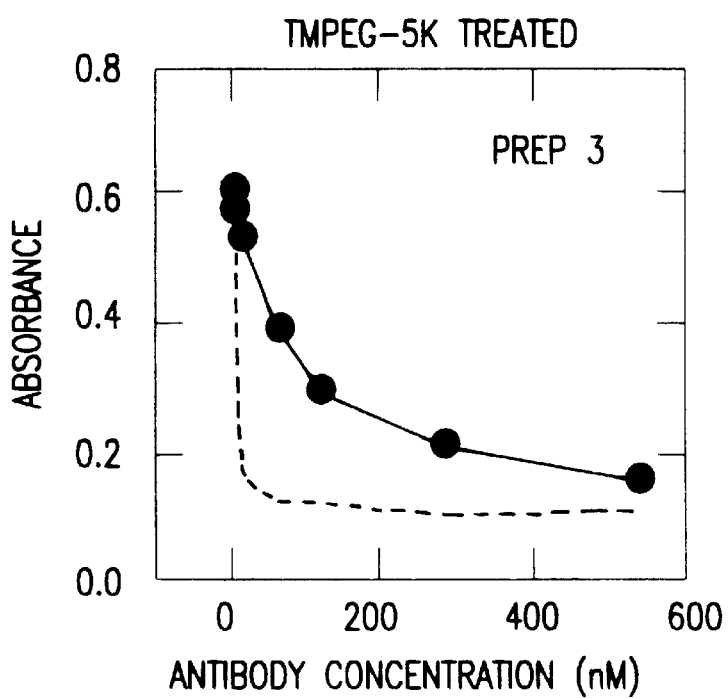
Figure 17G:
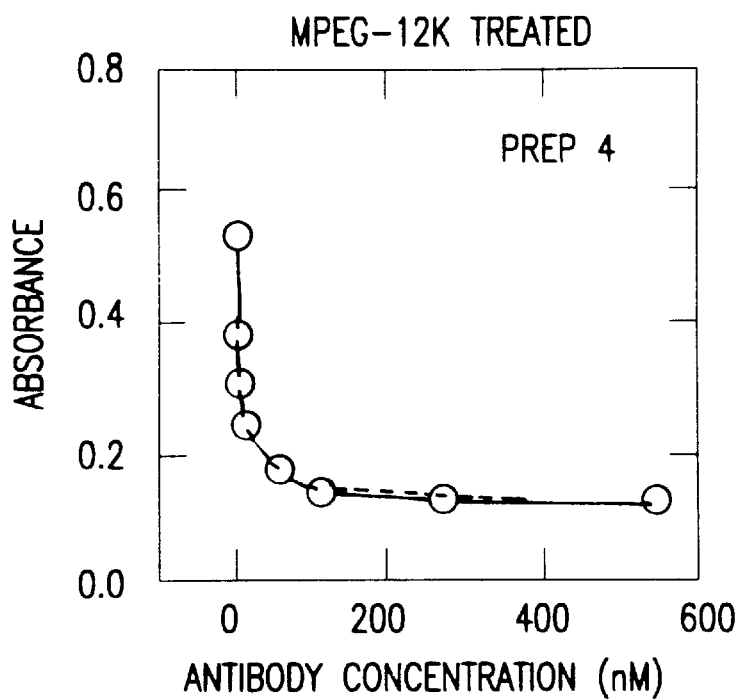
Figure 17H:
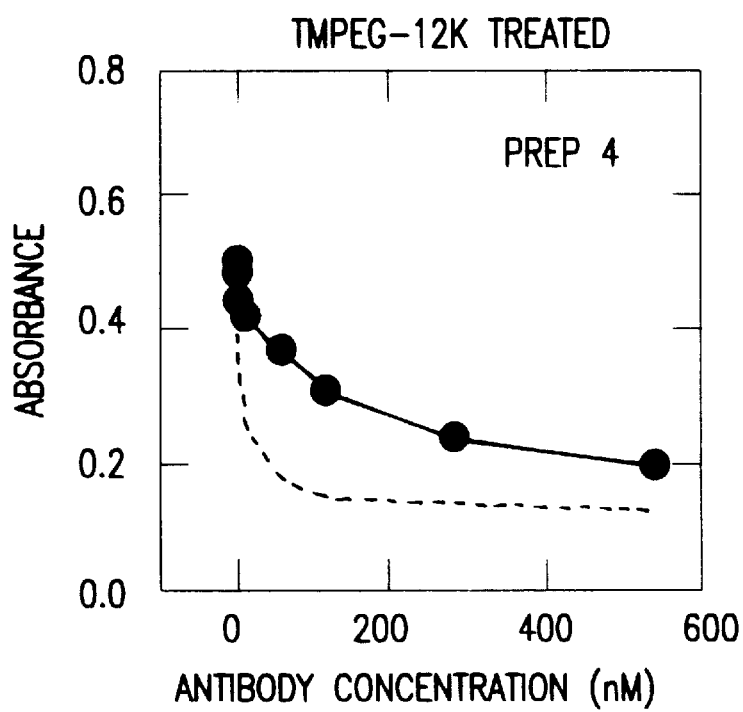
Figure 17I:
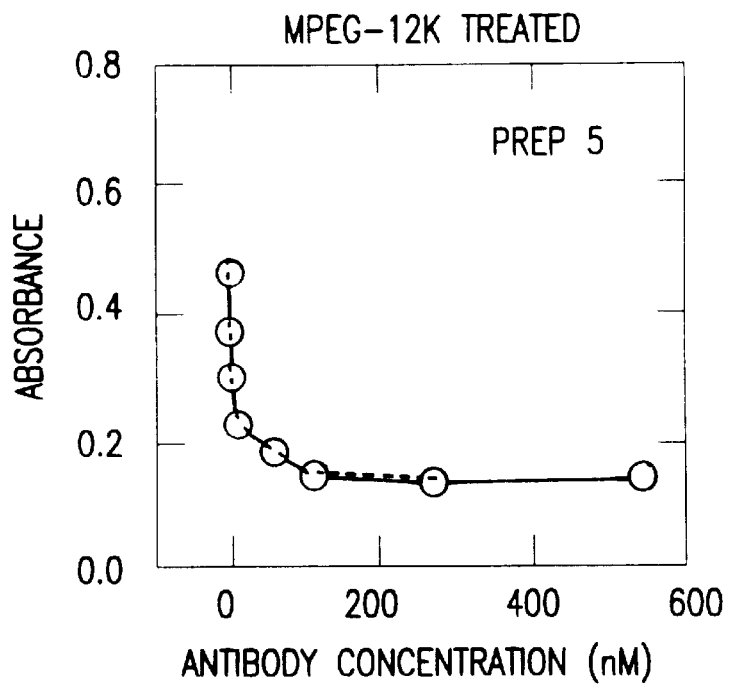
Figure 17J:
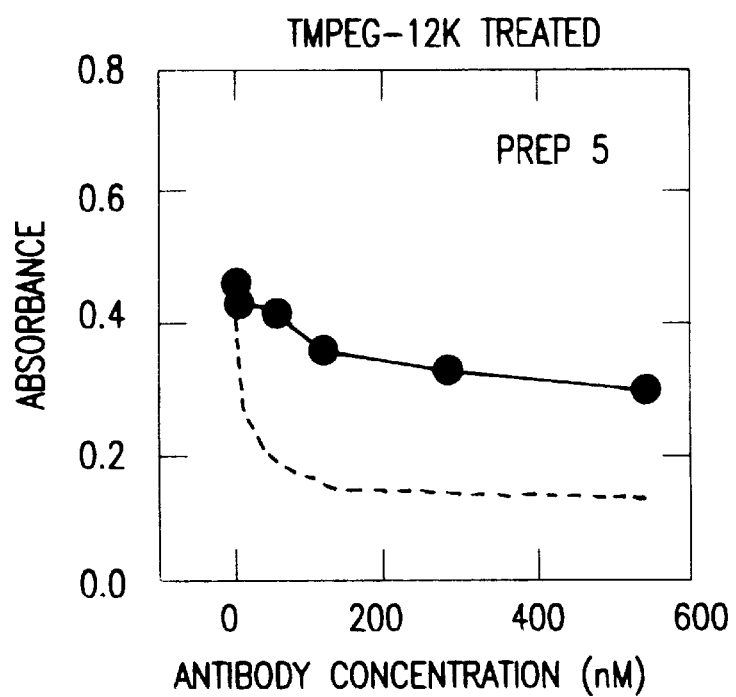

TMPEG modified Mab 8052 (modified at a ratio of 100:1 PEG:lysine as prepared in Example 6) and unmodified antibody were incubated with a detergent solubilized fraction of adenovirus for 2 hrs at 4° C. Antibody antigen complexes were captured with Staph A membranes and analyzed on a SDS-PAGE gel. FIG. 15 demonstrates that the PEGylated antibody was equally effective as the non-PEGylated antibody at immunoprecipitating viral hexon. Thus PEGylation did not grossly affect the antigen recognition site of the antibody.

Example 8

Indirect Adenovirus ELISA Using PEGylated Anti-hexon Antibodies

An indirect adenovirus ELISA was also performed to demonstrate that the PEGylated anti-hexon antibody still recognized adenovirus. The ELISA procedure is as follows: the 96 wells of a microtiter plate received 0.1 µg of inactivated adenovirus in coating buffer (100 mM carbonate pH 9.2 (Pierce)) and was incubated overnight at 4° C. After overnight incubation the plates received 150 µl of blocking buffer per well and were incubated for 1 h at 37° C. The plates were washed 3 times with wash buffer (PBS containing 0.05% Tween 20, 0.5% BSA (Pierce)). The wells then received 100 µl of a solution containing a 1:250 dilution of antibody (2 mg/ml) (control, TMPEG-Ab as prepared in Example 6 and antibody PEGylated with cyanuric chloride PEG as prepared in Example 6). A series of twofold dilutions of the antibody were performed across the plate. The plates were incubated overnight with antibody and the wells were subsequently washed 3 times with wash buffer. The antibody bound to the virus was quantified using a standard streptavidin-HRP assay kit (Pierce Chemical, Rockford, Ill.). Results are shown in Table 3.

TABLE 3

| Antibody | Titre |
|---|---|
| Control | 8000 |
| tmPEG-Antibody (10:1) | 8000 |
| tmPEG-Antibody (100:1) | 4000 |
| tmPEG-Antibody (200:1) | 4000 |
| CC-PEG Antibody (25:1) | 1000 |

TABLE 3-continued

| Antibody | Titre |
|---|---|
| CC-PEG Antibody (50:1) | >500 |
| CC-PEG Antibody (75:1) | >500 |

The results in Table 2 demonstrate that the anti-hexon antibody PEGylated with cyanuric chloride PEG had a lower titre for adenovirus compared to control or antibody PEGylated with TMPEG. This suggests that PEGylation of the antibody using TMPEG preserves the antigen recognition site of the antibody to a greater extent than PEGylation using cyanuric chloride activated PEG.

A competition ELISA was designed to determine if PEGylation of the antibody resulted in large changes in the affinity of the antibody for viral antigen. Anti-hexon antibody was PEGylated with either TMPEG or cyanuric chloride activated PEG. Antibody PEGylated with TMPEG was more capable of binding to the virus than antibody PEGylated with cyanuric chloride activated PEG as shown by competition of biotinylated anti-hexon antibody in a competition ELISA. The ELISA plate was coated with adenovirus as described in Example 9. After coating the wells received biotinylated antibody alone or biotinylated antibody and test antibody which included TMPEG antibody or cyanuric chloride-PEG antibody. The biotinylated antibody bound to the virus was then quantified using a standard strepavidin-HRP assay. If PEGylated antibody can compete effectively with the biotinylated parental antibody for sites on the virus there will be less biotinylated antibody bound the surface of the virus resulting in a lower titre value. Results are shown in Table 4.

TABLE 4

| Antibody | Titre |
|---|---|
| Biotinylated Parental | 4000 |
| Biotinylated parental + tmPEG-antibody (10:1) | 1000 |
| Biotinylated parental + tmPEG-antibody (100:1) | 1000 |
| Biotinylated parental + tmPEG-antibody (200:1) | 4000 |
| Biotinylated parental + CC PEG-antibody (25:1) | 4000 |
| Biotinylated parental + CC PEG-antibody (50:1) | 2000 |
| Biotinylated parental + CC PEG-antibody (75:1) | 2000 |

Table 4 shows that antibody PEGylated with TMPEG at the ratios of PEG:lysine of 10:1 and 100:1 could still effectively compete with the biotinylated parental antibody for virus. This resulted in less biotinylated antibody bound to the virus and hence a lower titre value. Antibody PEGylated with TMPEG at a ratio of 200:1 PEG:lysine was ineffective at competing with the biotinylated parental antibody suggesting that at this high ratio of PEG the antigen binding site of the antibody is compromised.

Antibody PEGylated with cyanuric chloride activated PEG was not effective at competing with the biotinylated parental antibody for binding to virus suggesting that PEGylation with cyanuric chloride PEG had compromised the antigen binding site of the antibody.

Example 9
Indirect PEGylation Via PEGylated Antibody

Further experiments were performed in which non-neutralizing anti-hexon antibody purified from hybridoma cell line HB8117, American Type Culture Collection, Rockville, Md. was used as a ligand with which to attach PEG to the virus. The antibody was incubated with TMPEG (as described in Example 1) in PBS at room temperature for 2 h using a rotary mixer. The final concentration of antibody was 100 $\mu$g/ml and the TMPEG was 10.6 mg/ml added to provide an excess of TNIPEG:$NH_2$. The excess TMPEG was neutralized by addition of glycine and a further 2 h incubation.

PEGylation of the antibody was confirmed by the increase in size shown by gel permeation chromatography (FIG. 16). The antibody preparation did not contain any significant proportion of residual unmodified antibody (note the lack of a subsidiary peak in the unmodified position). Incubation of the antibody with increasing concentrations of TMPEG-5K lead to a progressive displacement of the protein elution peak from circa 11.1 ml to circa 9.5 ml, 9.1 ml and 8.95 ml, indicative of increasing degree of modification (FIG. 16, left panels). Reactions prepared with 10.6 mg/ml and 22.5 mg/ml did not contain any significant proportion of residual unmodified antibody (note the lack of a subsidiary peak in the unmodified position). (FIG. 16, two top left panels). However, when the TMPEG concentration was increased to 45 mg/ml (FIG. 16, bottom left panel), the reaction mixture contained a small proportion of unmodified antibody. This might be due to partial precipitation of the protein induced by the high concentration of polymer, thus making the protein unavailable for PEGylation. Incubation of the antibody with TMPEG 12K lead to a displacement of the protein peak to circa 7.98 ml and 7.52 ml (FIG. 16, right panels). None of the reactions contained any significant proportion of unmodified antibody. The displacement of the protein elution peak by PEGylation was more marked for the conjugates obtained with TMPEG-12K than that observed for conjugates prepared with TMPEG-5K. Thus the conjugates obtained with TMPEG-12K have an overall hydrodynamic radius grater than that of the conjugates obtained with TMPEG-5K. A greater hydrodynamic radius could indicate: either a) greater impact per PEG chain for the TMPEG-12K than for the TMPEG-5K, or b) greater number of PEG chains attached with TMPEG-12K than with TMPEG-5K. However, the chromatograms do not allow to discriminate between these two possibilities.

Five preparations of PEGylated antibody covering a range of degrees of modification, three MPEG-5K-antibody conjugates (Preps 1 to 3 with elution volumes on the Superose 12 column at 9.31 ml, 9.08 ml and 8.96 ml, respectively) and two MPEG-12K antibody conjugates (Preps 4 and 5 with elution volumes on the Superose 12 column at 7.98 ml and 7.72 ml, respectively) were tested for binding to the viral surface.

PEGylated antibody was capable of binding to the virus using a biotinylated anti-hexon antibody in a competition ELISA (FIG. 17). The wells of a microtiter plate (96 wells) received 100 $\mu$l of a 1 $\mu$g/ml stock inactivated adenovirus in coating buffer and were incubated overnight at 4° C. After the overnight incubation, the plates received 150 $\mu$l of blocking buffer per well and were incubated for 1 h at 37° C. The plates were then washed 3 times with 400 $\mu$l of wash buffer per well. The wells then received 100 $\mu$l of a solution containing biotinylated antibody at 21.6 nM and test antibody (control, MPEG treated or TMPEG treated) at increasing concentrations ranging from 1.1 nM to 540 nM. The plates were incubated for 1 h at 37° C. and then the wells were washed 3 times with 400 µl of wash buffer. The biotinylated antibody bound to the virus was then quantified using a standard streptavidin-HRP assay. The stock inactivated adenovirus type 2 was obtained in lyophilized form, 200 µg/vial, from Lee Biomolecular Research, San Diego Calif., Cat No.405001. To produce the 1 µg/ml stock, the lyophilized powder was dissolved in 1 ml of distilled water and 50 µl were then diluted up to 10 ml with coating buffer. The coating buffer was 100 mM carbonate pH 9.2 (Pierce). Blocking buffer was PBS containing 0.05% Tween 20, 0.5% BSA (Pierce 10X). Wash buffer was PBS containing 0.05% Tween 20. The biotinylated antibody was at a concentration of 10.8 µM.

FIG. 17 shows the binding of biotinylated anti-hexon antibody to the viral surface in the presence of increasing concentrations of untreated monoclonal anti-hexon antibody (dotted lines), monoclonal anti-hexon antibody incubated with MPEG (open circles) and PEG-antibody (filled circles). The latter was obtained by incubation of the monoclonal anti-hexon antibody with TMPEG (see chromatogram in FIG. 16). Thus PEGylated antibody serves as an alternate approach for binding PEG to the viral surface.

Example 10
Quantitative Analysis OFPEGylated Adenoviral Vector

An Ad2/β-gal 2 vector (U.S. Pat. No. 5,670,488 and described by Zabner et al. (1996) *J. Virol.* 70: 6994) was covalently modified by PEG with 0.01%, 0.1%, 1.0% or 5.0% biotinylated NHS-PEG$_{5000}$ (Shearwater Polymers). PEGylated vector proteins were analyzed by SDS-PAGE. SDS-PAGE demonstrated that the hexon, penton base and fiber were the primary targets for covalent modification by PEG, and increasing concentration of PEG led to modification of additional proteins.

PEGylation of adenovirus was also assessed quantitatively. Ad 2-β-gal 2 vector was treated with increasing amounts of TMPEG-biotin 5%, 10%, or NHS-PEG-biotin 0.01%, 0.1%, 1%, 5%. Both PEG$_{5000}$'s were obtained from Shearwater Polymers. Stepwise additions of PEG were made every 30 minutes up to a period of 1 hour for TMPEG-biotin and 2 hours for NHS-PEG-biotin. Following PEG treatment the unreacted PEG was separated from the PEG-virus by CsCl gradient purification and the amount of PEG-biotin attached to the virus was quantitated using an ELISA assay with an avidin HRP conjugate as reporter. A standard curve of PEG-biotin (0–250 ng/ml) was generated to determine the number of molecules of PEG-biotin attached per virus particle. Results are shown in Table 5.

TABLE 5

| Sample | Molecules PEG-biotin:virus particle |
|---|---|
| 0.1% NHS-PEG-Biotin | 600:1 |
| 1% NHS-PEG-Biotin | 3077:1 |
| 5% NHS-PEG-Biotin | 3191:1 |
| 5% TMPEG-Biotin | 1500:1 |
| 10% TMPEG-Biotin | 1000:1 |

Treatment of adenovirus with either TMPEG-biotin or NHS-mPEG-biotin led to the covalent attachment of PEG-biotin to the surface of the virus. The data indicates that at comparable concentrations of tresyl and NHS PEG-biotin, more PEG-biotin was attached to the virus particle after treatment with the NHS-PEG biotin, which is consistent with reports that the reaction of NHS-PEG with lysine residues occurs more quickly (30–45 minutes) compared to the reaction of tresyl mPEG with lysine residues which occurs over an extended period of time (2–3 hours).

This data provides quantitative results regarding the extent of covalently bound PEG.

Example 11
Covalent Attachment of Polyethylene Glycol to Adenovirus

Type 2 adenovirus (genetically modified to carry the β-gal reporter gene) was prepared by banding with isopycnic CsCl density centrifugation then extensively dialysed against phosphate buffered saline (PBS pH 7.2). Three different types of mPEGs were tested for their ability to PEGylate adenovirus namely a) cyanuric chloride activated mPEG$_{5000}$ b) TMPEG$_{5000}$ and c) amino-PEG$_{5000}$. The mPEGs were obtained from Shearwater Polymers. Activation of mPEG with cyanuric chloride couples one triazine ring per mPEG molecule. This activated mPEG can react with amino groups on proteins. Alternatively mPEG can be activated with tresyl chloride (2,2,2,-trifluoroethanesulphonyl chloride) to form tresylated mPEG which can react with epsilon amino groups on proteins to form a highly stable amine linkage. SPDP-amino mPEG couples to proteins via cysteine residues. The activated NHS ester end of SPDP reacts with the amine groups on the amino PEG to form an amide linkage. The 2-pyridyldithiol group at the other end is free to react with sulfhydryl groups to form a disulfide linkage. SPDP-aminoPEG was synthesized by the addition of SPDP (N-succinimidyl 3-(2-pyridylditthio) peropionate) to amino PEG in the presence of methanol. Following an overnight incubation at room temperature the SPDP-aminoPEG was collected by precipitation with ether.

Ad2-β-gal 2 virus was incubated with either a) cyanuric chloride activated mPEG b) TMPEG or c) amino PEG at increasing ratios of PEG:lysine. Ad2-β-gal 2 virus was dialysed into 0.1M sodium carbonate buffer pH 8.5 containing 0.15M NaCl before treatment with cyanuric chloride activated mPEG or 0.2 M sodium phosphate buffer pH 7.5 containing 0.15 M NaCl before treatment with TMPEG. All PEGylation reactions were performed at room temperature. Samples were mixed on a rotary platform, the PEGylation reaction was terminated by the addition of excess lysine or alternatively by lowering the temperature. Infectivity of the PEGylated viruses was initially assessed qualitatively by infecting 293 cells with PEGylated virus followed by measurement of transgene expression (β-galactosidase) using X-gal staining. Using this assay the TMPEG treated virus had greater infectivity than the virus that had been treated with cyanuric chloride activated PEG or SPDP-PEG. The TMPEG treated virus was further measured for infectivity using the more quantitative assay of end-point dilution in 293 cells using fluorescence isothiocyanate (FITC)-conjugated anti-hexon antibody as described by Rich, D P, Couture L A, Cardoza L M, Guiggio, V M, Armentano, D., Espino, P C, Hehir, K., Welsh, M J, Smith, A E and Gregory, R J, 1993, Hum. Gen. Ther. 4:461–476.

The results are shown in Table 6 and demonstrate that infectivity of the virus is retained following PEGylation with TMPEG. (Error in the assay is ±0.5 log.)

TABLE 6

| PEG:Lysine | Infectivity |
|---|---|
| 5:1 | 3.8e8 iu/ml |
| 2.5:1 | 1.5e8 iu/ml |
| 1:1 | 2.2e8 iu/ml |
| Control | 5e8 iu/ml |

Example 12
Reduced Binding of Neutralizing Antibodies to PEGylated Vector

Ad2-β-gal 2 virus was PEGylated with TMPEG as described in Example 11. Virus was incubated with serial two-fold dilutions of neutralizing human serum for 1 h/37° C. and 293 cells were added. The assay was read when 293 cells incubated alone reached confluency. The neutralizing titer was defined as the reciprocal of the highest dilution of serum that showed detectable protection of 293 cells from cytoplathic effect when compared to cells incubated with virus not exposed to serum. Prior to the assay, the different virus preparations to be tested were titrated to ascertain the lowest dilution that caused 100% cytopathic effect. Results are shown in Table 7.

TABLE 7

| Virus PEG:lysine ratios | Neutralizing titre |
|---|---|
| 5:1 | 800 |
| 2.5:1 | 3200 |
| Control | 6400 |

According to the results, more serum is required to neutralize the PEGylated virus compared to the untreated virus suggesting that PEGylation covers sites recognized by neutralizing antibodies.

Example 13
Ion-exchange Chromatography of PEGylated Virus Particles

Ad 2-β-gal virus was PEGylated as described in Example 11 with TMPEG at ratios of 50 moles and 10 moles PEG:lysine. The virus was applied to a DEUCE ion-exchange resin (Millipore, Bedford, Mass.) in phosphate buffer containing NaCl. Bound virus was eluted from the resin using an increasing salt gradient and the flow through peaks and eluted protein peaks were analyzed for control virus, virus treated with TMPEG at a ratio of 50:1 PEG:lysine and virus treated with PEG at a ratio of 10:1 PEG:lysine. All samples had equivalent protein values before chromatography.

Figure 18A:
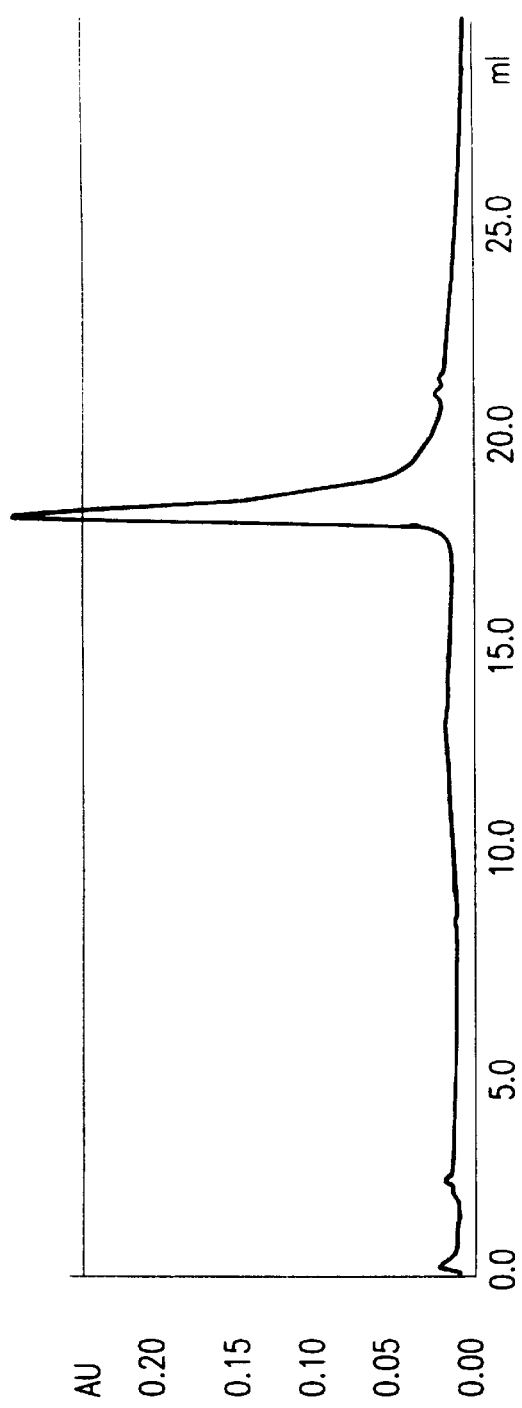
FIGS. 18A–C shows the elution profile of control and TMPEG-treated virus from DEAE ion exchange resin following chromatography.
Figure 18B:
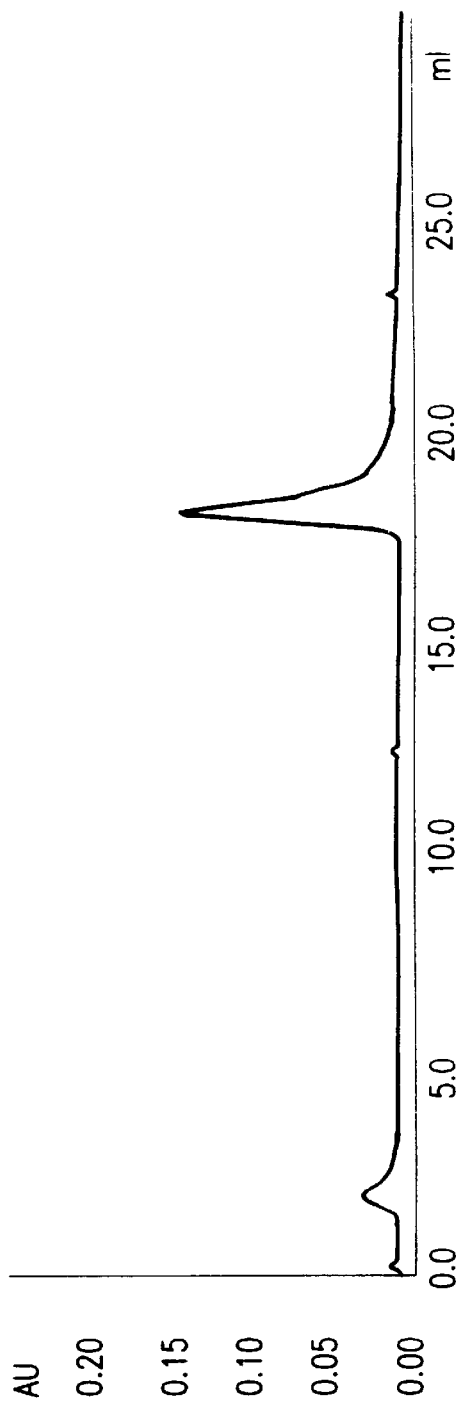
Figure 18C:
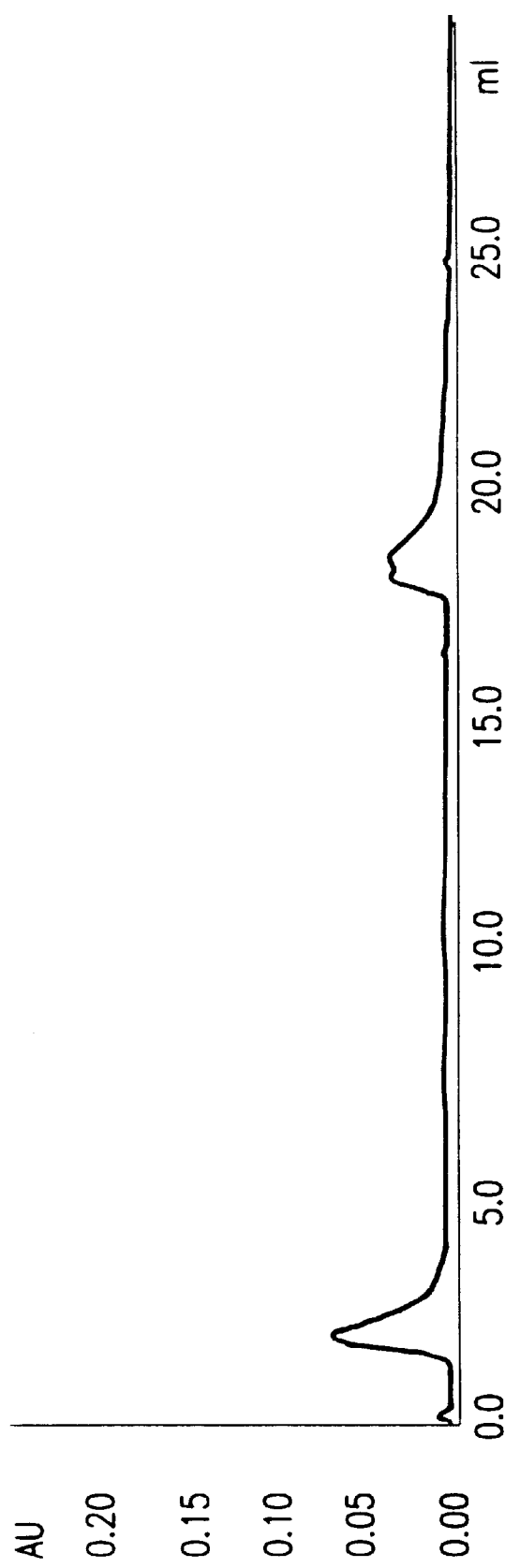

FIG. 18, panel A shows the elution profile from the DEAE-ion exchange resin (Millipore, Bedford, Mass.) following chromatography of control virus. One main protein peak was eluted from the resin and this was shown to contain infectious virus particles (data not shown). FIG. 18, panel B shows the elution profile from the DEAE-ion exchange resin following chromatography of virus that had been treated with TMPEG (10:1 ratio). In contrast to the profile for the control virus there is the appearance of a flow through peak in addition to the eluted protein peak, which has diminished in size. The appearance of the flow through peak suggests that PEGylation has generated viral particles which no longer can bind to the DEAE-resin under these conditions and as a result are now present in the flow through peak along with unreacted PEG. Since ion-exchange chromatography is based on charge interactions between the protein and the ion-exchange resin, apparently PEGylation has produced a heterogenous population of virus particles which have altered surface charges. Those with significant surface charge differences can no longer bind to the resin and are recovered in the flow through peak. The elution profile from the DEAE-ion exchange resin following chromatography of virus PEGylated with TMPEG at a ratio of 50:1 showed a similar profile. The flow through peak in this sample was significantly larger while the eluted protein peak was in contrast reduced. At the increased ratio of PEG:lysine of 50:1 which resulted in a greater fraction of particles eluting in the flow through peak, the virus particles had increased levels of PEGylation. Table 8 expresses the size of the two peaks (expressed as area under peak) in relation to the PEG:lysine ratios used during PEGylation. In conclusion, ion exchange chromatography may be used to resolve heterogeneous populations of PEGylated virus particles and may be used to separate highly PEGylated virus particles from lightly PEGylated particles on the basis of charge differences.

TABLE 8

| | Flow Through Peak Area | Eluted Peak Area |
|---|---|---|
| Control | NA | 0.272 |
| PEG-Virus 10:1 | 0.022 | 0.132 |
| PEG-Virus 50:1 | 0.063 | 0.031 |

Example 14
Transgene Expression by PEGylated Ad2/β-Gal2 in Immune Mice

Two batches of Type 2 adenovirus stock solution prepared as in Example 1 were mixed (2 ml of a batch at $5.38 \times 10^{10}$ infectious units per ml, $2.055 \times 10^{12}$ particles per ml and 4 ml of a batch at $1.35 \times 10^{10}$ infectious units per ml, $9.3 \times 10^{11}$ particles per ml) and subjected to treatment with PEG using a stepwise addition regime of 5% TMPEG as in Example 3. Samples obtained following two and three additions of TMPEG (i.e., total 10% and 15% TMPEG, respectively) were purified from unreacted TMPEG by a standard CsCl (Sigma Chemical, St. Louis, Mo.) centrifugation procedure involving a step gradient and two sequential equilibrium gradients. The purified PEG treated vectors were then dialyzed against phosphate buffered saline containing 5% sucrose and frozen at −80° C. in small aliquots. The titers were determined by end point dilution on 293 cells using fluorescence isothiocyanate (FITC)-conjugated anti-hexon antibody as described by Rich, D P, Couture L A, Cardoza L M, Giuggio V M, Armentano D, Espino P C, Hehir K, Welsh M J, Amith A E and Gregory R J, 1993, *Hum. Gen Ther.* 4:461–476. The purified PEG treated viral suspension prepared with total 10% TMPEG contained $2.7 \times 10^{11}$ particles/ml ($3 \times 10^9$ infectious units/ml) and the purified PEG treated viral suspension prepared with total 15% TMPEG contained $2.4 \times 10^{11}$ particles/ml ($6.4 \times 10^8$ infectious units/ml).

The two PEGylated viral suspensions were compared to untreated Type 2 adenovirus ($3.19 \times 10^{10}$ infectious units per ml) for ability to effect gene transfer in vivo in naive and pre-immunized BALB/c mice. Mice were pre-immunized by the intra-nasal administration of $10^9$ infectious units of a replication defective Type 2 adenovirus encoding human CFTR (Ad2/CFTR). The animals chosen for the study had serum anti-adenovirus antibody titers of circa 1/25,000 to 1/50,000. Naive BALB/c mice were simply mice that had not been exposed to adenovirus vector. On day 0, the viral preparations were administered as follows: a) untreated virus, $2 \times 10^8$ infectious units were instilled in a volume of 100 μl to each of four mice in the naive group and four mice in the pre-immunized group, b) "PEGylated virus 10%", $3 \times 10^8$ infectious units ($2.7 \times 10^{10}$ particles) were instilled in a volume of 100 μl to each of four mice in the naive group and four mice in the pre-immunized group, c) "PEGylated virus 15%", $6.4 \times 10^7$ infectious units ($2.4 \times 10^{10}$ particles) were instilled in a volume of 100 μl to each of four mice in the naive group and four mice in the pre-immunized group. All animals in the pre-immunized group were subjected to eyebleed on the day of instillation and the blood was analyzed for antibody titers. All mice were sacrificed three days after instillation and lung tissue, right caudal lobe and left lobe, was excised. The right caudal lobe from all four naive and four immunized animals per condition (untreated, "PEGylated virus 10%" and "PEGylated virus 15%") was used for quantification of á-gal in an AMPGD assay (Galacto-Light™ Kit, Tropix, Bedford, Mass.). The protein concentration of lung homogenates was determined using the BioRad DC reagent (BioRad, Hercules, Calif.). The left lobe from two naive and two immunized animals per condition was used for x-gal staining.

Table 9 shows the beta-galactosidase expression per microgram of protein (relative light units, RLU per microgram of protein) for untreated virus, "PEGylated virus 10%" and "PEGylated virus 15%" in both naive and pre-immunized mice. Beta-galactosidase expression in the naive mice was observed for all three viral preparations in all four mice per condition. In the pre-immunized mice, the untreated vector gives only background levels of beta-galactosidase expression in all four mice. In contrast, the two PEGylated viral preparations gave levels of beta-galactosidase above those for the control animals in 4/4 and 3/4 animals for the "PEGylated virus 10%" and "PEGylated virus 15%" preparations, respectively (see Table 5). Thus PEGylation of the virus conveys protection from neutralization in vivo resulting in substantial expression of the vector in the target tissue in vivo.

TABLE 9

Beta-Galactosidase expression in lung tissue expressed as relative light units per microgram of protein (RLU/μg protein).

| Preparation (infectious units) | Mouse Number | RLU/μg protein Native | RLU/μg protein Immunized |
|---|---|---|---|
| Control virus | 1 | 955 | 25 |
| ($2 \times 10^8$ iu) | 2 | 1457 | 90 |
| | 3 | 649 | 28 |
| | 4 | 1388 | 38 |
| PEGylated 10% | 1 | 2341 | 218 |
| ($3 \times 10^8$ iu) | 2 | 2108 | 1296 |
| | 3 | 3694 | 164 |
| | 4 | 1730 | 1964 |
| PEGylated 15% | 1 | 705 | 34 |
| ($6.4 \times 10^7$ iu) | 2 | 172 | 305 |
| | 3 | 715 | 198 |
| | 4 | 1128 | 108 |

Example 15
Pegylation of Adenovirus ONYX-015

Genetic modification of viruses to produce replication competent viruses with restricted permissiveness has been demonstrated in a number of cases (e.g. for tumour cells, hypoxic tissues and tissues having specific promoters). Adenovirus ONYX-015 (ONYX Pharmaceuticals) is an example of such viruses, which has been designed to propagate selectively in tumours. The virus is a chimera of adenovirus types 2 and 5, which replicates more efficiently in cells lacking the regulatory protein p53. Such cells include a number of tumour cell lines. The covalent attachment of polymer to the virus would be expected to enhance the tumour targeting ability of the virus, adding further advantages to those achieved with PEGylation, ideally whilst maintaining infectivity and protecting the virus from the effects of neutralising antibodies.

TMPEG was prepared as disclosed in Example 1. Adenovirus ONYX-015 was prepared following infection of human 293 cells, by ion exchange chromatography (IEC) using Resource Q media on a PerSeptive BioSystems chromatograpy workstation. The running buffers used were as follows; Buffer A: 150 mM HEPES; 20 mg/ml sucrose; 2 mM MgCl2, pH 7.5 (adjusted with NaOH), Buffer B: 1.5M NaCl in buffer A.

Virus purification was effectuated using a gradient of 0–5 minutes, 20% B; 5–15 minutes 20–50% B; 15–20 minutes, 100% B; 25–30 minutes, 20% B. Concentrated stocks of virus ($9 \times 10^{11}$ pfu/ml) were diluted in virus storage buffer (VSB10 mM Tris base,pH 7.4, 1 mM MgCl2, 150 mM NaCl, 10% glycerol) to give a working concentration of $1 \times 10^{11}$ pfu/ml. Aliquots of virus were stored at −70° C. It should noted that TRIS is undesirable in PEGylation reactions since it is a nucleophile and must either be diluted sufficiently or the buffer must be exchanged.

Adenovirus ONYX-015 ($1 \times 10^{11}$ pfu/ml and circa $1 \times 10^{12}$ particles/ml) was reacted with $PEG_{5000}$ using an addition of PEG in 5%(w/v) steps (as described in Example 3). Each activated polymer addition was incubated for 30 min at 25° C., on a rotary wheel. Final concentrations of TMPEG or MPEG at 5, 10, 15 and 20% (w/v), were obtained. The polymer modified virus was assessed by IEC. The IEC method was run with a 1 ml Resource Q column (Pharmacia), using a HP1100 HPLC system. The running buffers used were as follows; Buffer A: 150 mM HEPES; 20 mg/ml sucrose; 2 mM MgCl2, pH 7.5 (adjusted with NaOH), Buffer B: 1.5M NaCl in buffer A. They were run in a gradient of, 0–5 minutes, 20% B; 5–15 minutes 20–50% B; 15–20 minutes, 100% B; 25–30 minutes, 20% B.

Figure 19C:
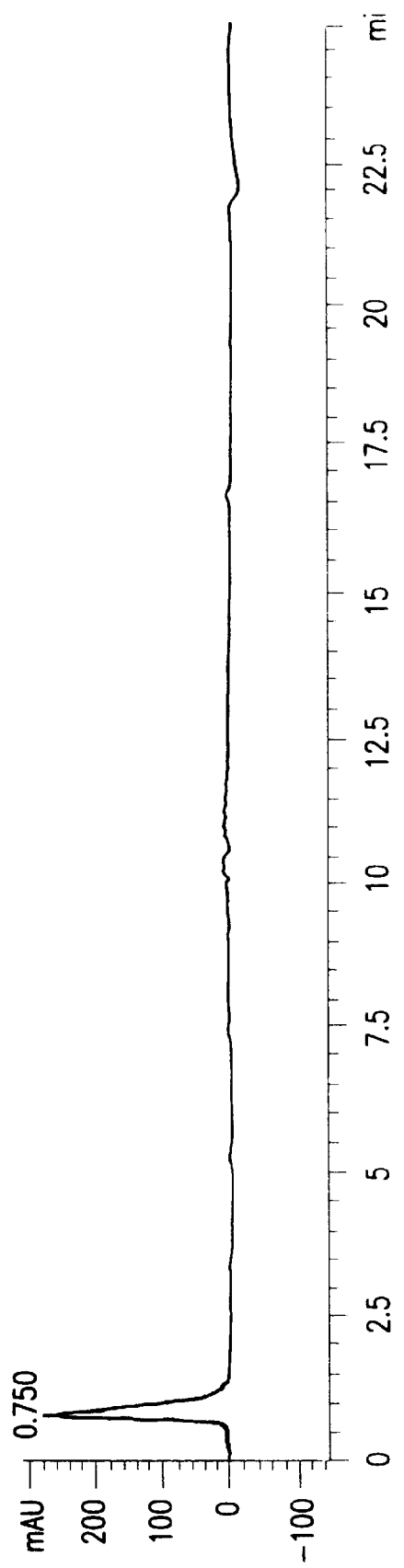
Figure 20A:
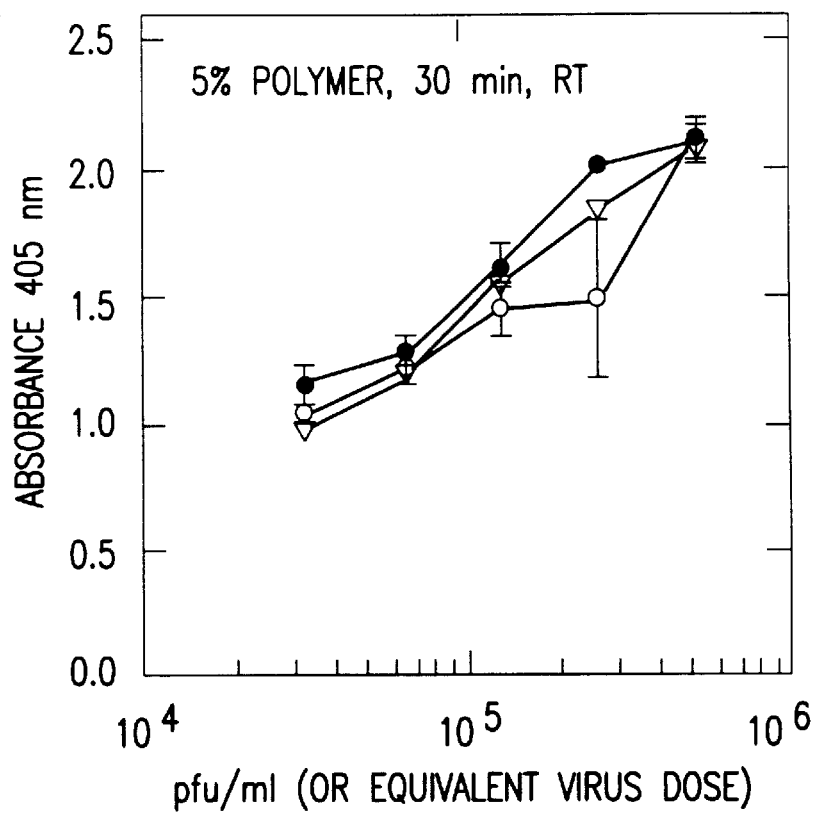
FIG. 20 depicts infectivity assay results (ELISA for hexon protein) following stepwise additions of 5% $TMPEG_{5000}$ or $MPEG_{5000}$ to Adenovirus ONYX-015.
Figure 20B:
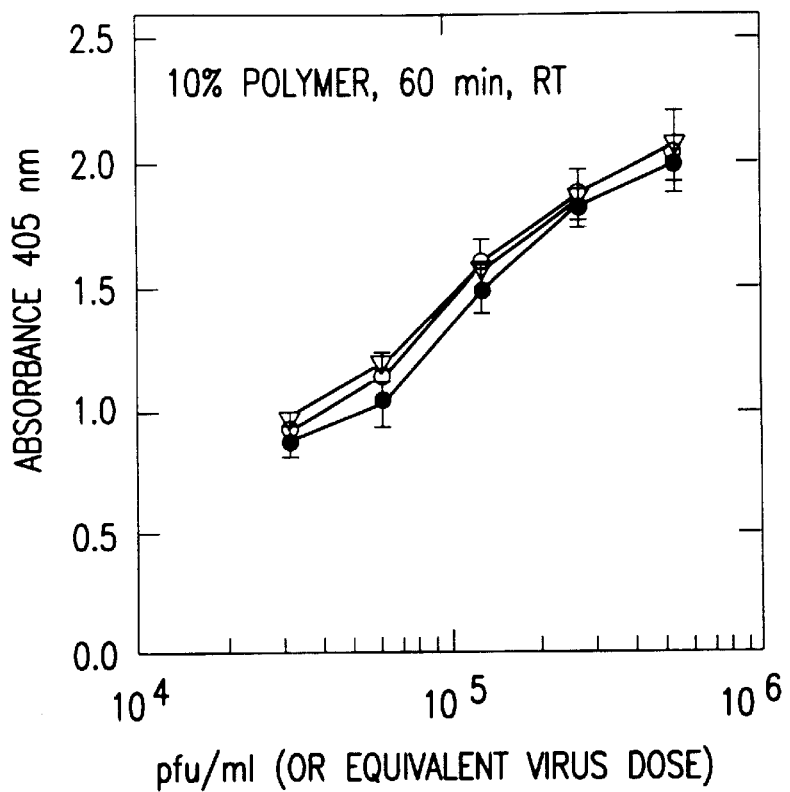
Figure 20C:
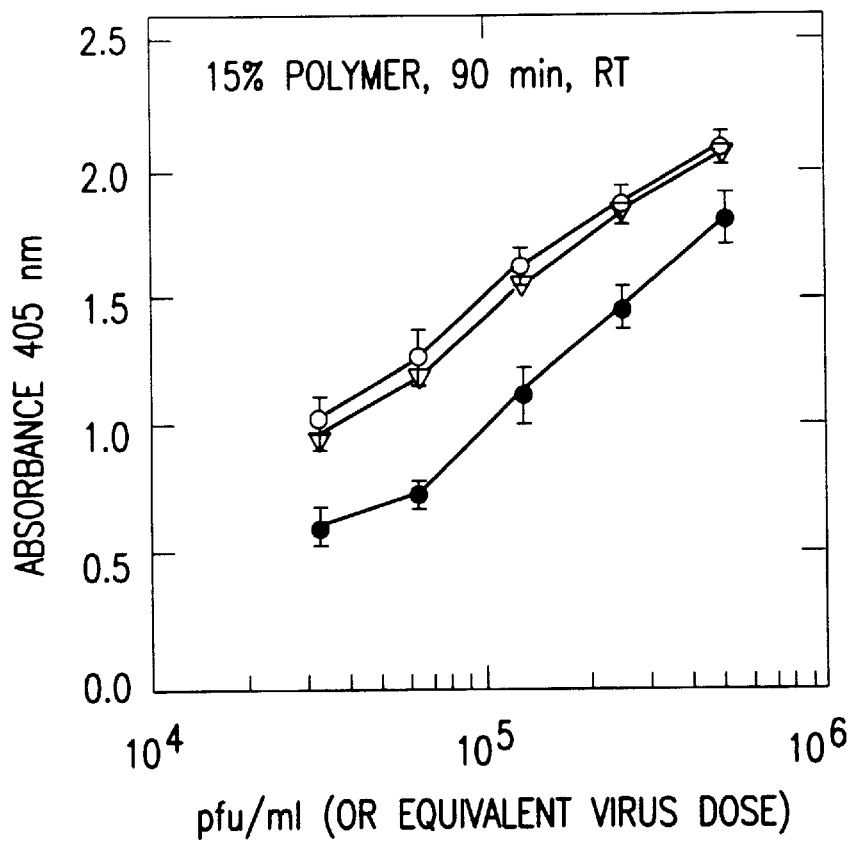
Figure 20D:
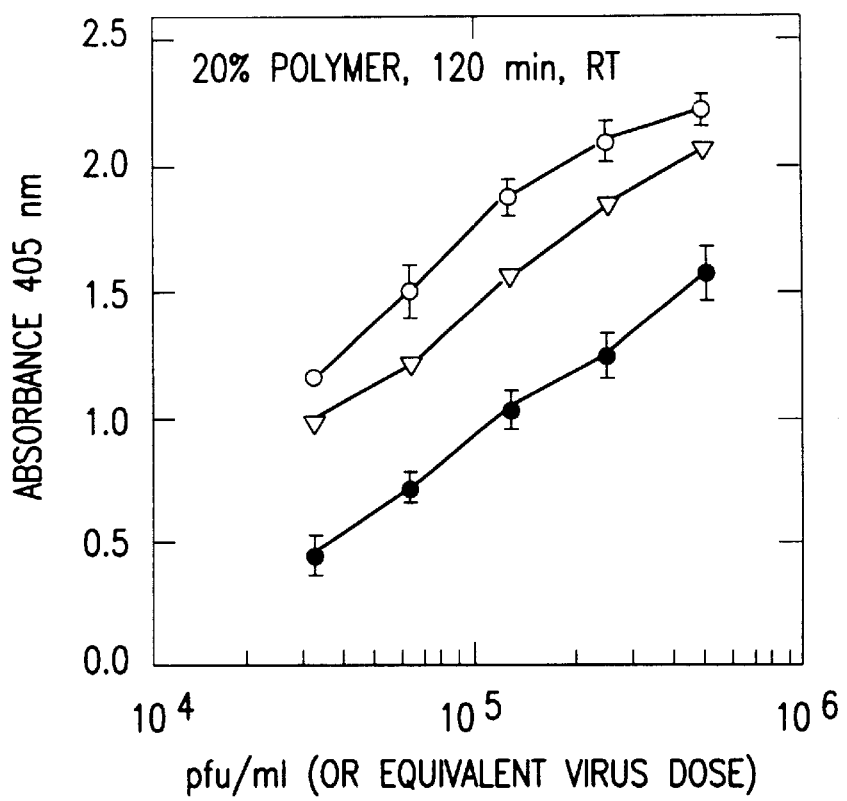
Figure 21A:
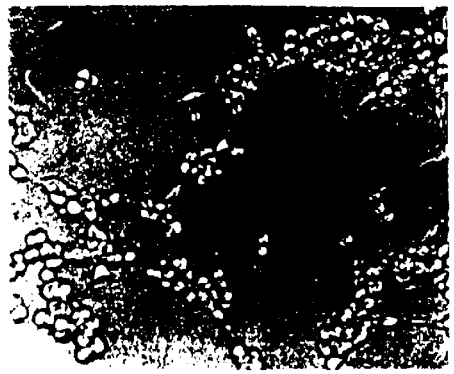
FIGS. 21A–F shows a laser copy of photographs demonstrating cytophatic effect (CPE) for untreated Adenovirus ONYX-015 (panels A–B) and ONYX-015 incubated with 5% $MPEG_{5000}$ (panels C–D) or $TMPEG_{5000}$ (panels E–F).
Figure 21B:
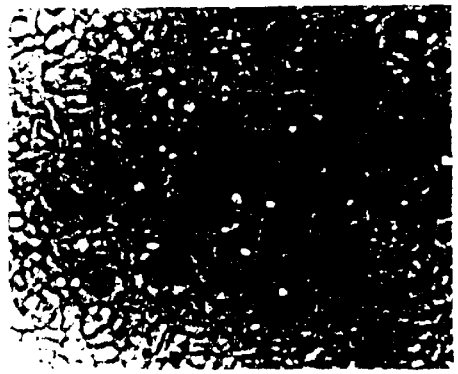
Figure 21C:
Figure 21D:
Figure 21E:
Figure 21F:
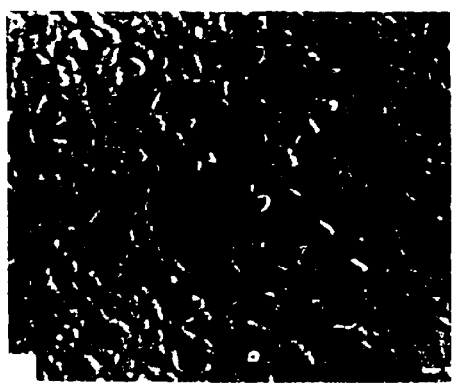

The IEC method used demonstrates, that in virus samples treated with TMPEG, the shrouding effect of the PEG chains have resulted in sufficient neutralisation of surface charge of the virus particles to inhibit interaction with the column. The chromatogram in FIG. 19, demonstrates this effect. Untreated virus particles (FIG. 19a) were effectively eluted at 10.90 minutes (570 mM NaCl), whereas MPEG treated virus (FIG. 19b), samples were eluted at 10.91 minutes (570 mM NaCl). In the TMPEG treated virus samples, no peak was present at this location, with a peak at the column void volume being observed (FIG. 19c).

A peak also appeared at 0.75 min in the TMPEG treated sample and examination of the spectrum at that location (not shown) was consistent with the new peak being due to PEGylated virus. In some examples, an increase in peak height was observed rather than a new peak at this location indicating that not only PEGylated virus but also other material can elute at this location.

Example 16 and Comparative Example 16
Infectivity Assays for PEG-treated (TMPEG) and Sham-treated (MPEG) Adenovirus ONYX-015

PEGylated adenovirus ONYX-015 was prepared as in Example 15 and assessed in infectivity assays. Infectivity was assessed in an ELISA assay, using antibody detection of the major structural hexon protein.

Human 293 cells were seeded at $5 \times 10^5$ cells/ml, in 96-well plates (100 ml/well), and allowed to adhere preferably overnight, or for at least 2 hrs at 37° C. The PEG-reacted virus samples were diluted in Dulbecco's Minimal Essential Media (DMEM), containing 2% fetal calf serum, to give virus concentrations of $1\times10^6$, $5\times10^5$ and then four half log dilutions. Semi-confluent cell monolayers were infected with 100 μl/well of diluted virus (6 replicates for each), for 48 hrs at 37° C. and 5% $CO_2$.

After 48 hrs, the cells were examined for cytopathic effect (CPE) using phase contrast microscopy, and results were recorded by photography.

The cells were then pelleted at 1000 rpm for 2 min, washed twice in phosphate buffered saline (PBS), fixed in iced ethanol containing 5% acetic acid for 10 min at −20° C., washed in PBS and blocked in Superblock (Pierce Chemical Co.,: Cat. No.37535), for 1 hr at room temperature or overnight at 4° C. Cells were incubated with primary anti-hexon antibody, Access Biomedic Inc. (diluted 1:1000 in PBS comprising 3% Bovine serum albumin-BSA-PBSB) for 1 hr at room temperature. This was followed by incubation in a secondary antibody (rabbit alkaline phosphatase, diluted 1:1000 in PBSB with 0.1% Triton X 100, Pierce Cat No:I21) for 1 hr at room temperature. The cells were washed in Tris Buffered saline (TBS), and incubated in PNPP (p-Nitrophenyl phosphate, disodium salt) substrate, prepared according to manufacturers instructions, (Pierce Cat No:37620), for 20 min. The reaction was stopped with 100 μl/well 2 N NaOH, and the results read at 405 nm (Molecular Devices Emax Microplate Reader).

Single and stepwise additions of $TMPEG_{5000}$ and $MPEG_{5000}$ were prepared as in Example 15 and the preparations were monitored by IEC for PEGylation.

FIGS. 20a–d shows the effect of 5% additions of $TMPEG_{5000}$ and $MPEG_{5000}$ on adenovirus ONYX-015 infectivity. The infectivity of virus treated with 5 or 10% PEG is similar for each treated virus sample (open circles MPEG; closed circles TMPEG) and the untreated sample (triangles), whereas at 15 and 20% PEG the infectivity of the TMPEG treated virus is reduced with respect to the other two samples, but is still maintained at a significant level. FIGS. 21a–f, shows that the CPE exhibited by cells infected with untreated virus (a & b), TMPEG-treated virus (c & d) and MPEG-treated virus (e & f) are similar, suggesting that treatment with TMPEG does not result in substantial loss of infectivity or replication ability of this virus.

The effect of PEG treatment on virus infectivity was also assessed using plaque assays. Virus samples were prepared as in Example 1 and 15. The PEG treated and untreated virus samples were serially diluted in DMEM (with 2% FCS) to give dilutions of $10^{-4}$ to $10^{-9}$ of the original innoculum ($1\times10^{11}$ pfu/ml).

Semi-confluent monolayers of HEK 293 cells were set up in 6-well plates, and allowed to establish overnight at 37° C. The medium was removed and the cells infected with 200 μl/well of diluted virus inoculum. Cells were infected for 1 hr at 37° C., the innoculum removed and the cells overlayed with 2× DMEM (with 10% FCS) and 3% Seaplaque agarose (Flow laboratories) (1:1 v/v). The overlay was allowed to solidify and then overlayed with liquid DMEM (with 10% FCS). The assays were set up in duplicate, and incubated at 37° C. Assays were examined for plaque formation at 5–6 days post infection (dpi). Once plaques were observed, the assays were stained with neutral red stain (0.1% in PBS) and the numbers of plaques recorded.

Virus samples treated with 3% $TMPEG_{5000}$ and $MPEG_{5000}$ produced plaque titration of $3.0\times10^9$ pfu/ml and $4.5\times10^9$ pfu/ml respectively, whereas the untreated control virus produced a titre of $6\times10^9$ pfu/ml. This suggested that both sample handling and attachment of PEG chains have a modest and independent impact on infectivity.

In samples treated with 5% additions of $TMPEG_{5000}$ and $MPEG_{5000}$, resulting in 20% PEG treatment, titres of $6.8\times10^9$ pfu/ml and $7\times10^9$ pfu/ml respectively were attained. In comparison, untreated virus produced titres of $5\times10^9$ pfu/ml. Thus, in this experiment neither handling nor PEG chain attachment appear to have reduced infectivity or replication ability.

Further observations on cells infected using $TMPEG_{5000}$-treated virus, were made using antibody staining and immunofluorescence microscopy.

Virus samples were treated with $TMPEG_{5000}$ and $MPEG_{5000}$ as described in Example 15.

Semi-confluent monolayers of HEK 293 cells were set up in 8 well slide chambers (Nunc), and allowed to adhere overnight at 37° C. The medium was removed and the cells were infected with TMPEG-treated, MPEG-treated or untreated virus innoculum diluted in DMEM (with 2% FCS) to $1\times10^6$ pfu/ml (50 μl/well) for 1 hr at 37° C., after which the inoculum was replaced with DMEM, containing 5% FCS. Cells were incubated at 37° C. and prepared for microscopy at 48 and 72 hours post infection (hpi), as follows.

Cells were washed in PBS (5 min), blocked in PBSB for 1 hr at room temperature, washed in PBS and then incubated in primary anti-hexon antibody (diluted 1:1000 in PBSB, Access Biomedic Inc.) for 1 hr at 37° C. The cells were washed in PBS, and incubated in secondary goat anti-rabbit FITC conjugate (diluted 1:80 in PBS, Sigma Chem. Co.) for 1 hr at 37° C. The cells were washed extensively in PBS, three times in sterile distilled water, and mounted in Citifluor anti-fade mountant (Agar Accessories Ltd.). Slides were viewed using a Olympus Epifluoresence Microscope.

Figure 22:
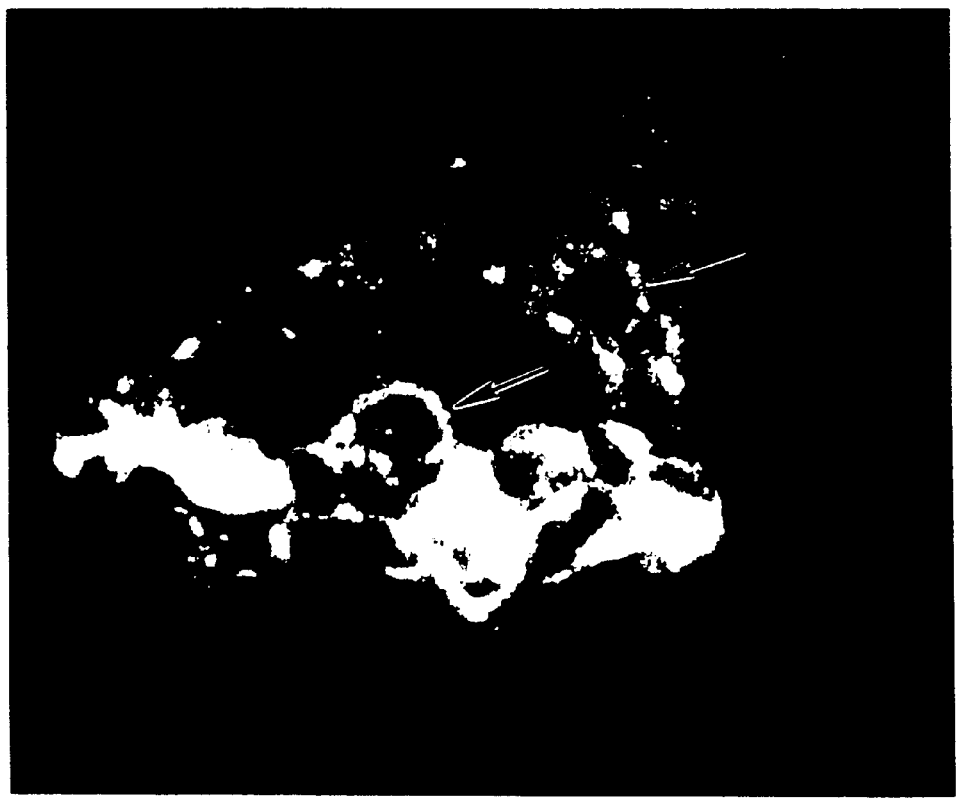
FIG. 22 shows a laser copy of immunofluorescence photographs (staining with anti-hexon antibody) demonstrating infectivity and replication of adenovirus ONYX-015 incubated with $TMPEG_{5000}$.

Immunofluoresence micrographs in FIG. 22 show staining with anti-hexon antibody in cells infected with $TMPEG_{5000}$ treated ONYX-015 virus, at 48 h post incubation, suggesting that treatment with TMPEG produces no inhibitory effect on virus replication.

Example 17

Covalent Attachment of Polyethylene Glycol to Poxvirus

As a representitive virus vector from the Poxvirus family Vaccinia virus strain MJ was selected. Strain MJ of Vaccinia virus containing a lacZ gene which encodes β-galactosidase (VVMJ.lacZ), was used to demonstrate the covalent attachment of TMPEG to a Poxvirus vector. Vaccinia virus strain MJ.lacZ was prepared from infected BS-C-1 cells, grown in minimal essential medium (MEM), supplemented with 10% FCS. Vaccinia virus MJ.lacZ and BS-C-1 cells were obtained from Dr. A. Alcami, Division of Virology, Department of Pathology, University of Cambridge, Tennis Court Road, Cambridge, U.K. Purified virus stocks were prepared by sedimentation through a sucrose cushion, dialysed against PBS overnight at 4° C., and titrated by plaque assay in TK⁻ 143B cells (provided by Dr. Alcami). Titres of $6\times10^9$ pfu/ml were obtained.

Aliquots of virus were reacted with $TMPEG_{5000}$ and $MPEG_{5000}$ in 5% (w/v)steps as described in Example 15. Samples from the 5% and 20% reactions were diluted in minimal essential medium (MEM) supplemented with 2% FCS, to give serial dilutions of $10^{-5}$ to $10^{-9}$.

Figure 23A:
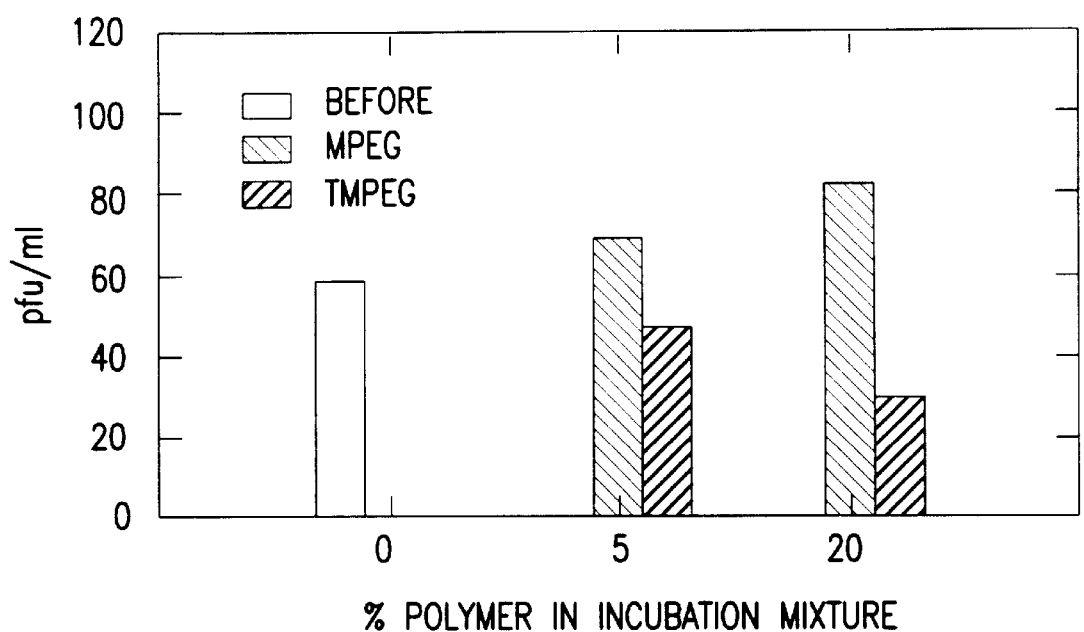
FIG. 23 shows the infectivity measured by plaque assay of vaccinia virus following stepwise addition of MPEG500 or $TMPEG_{5000}$.
Figure 23B:
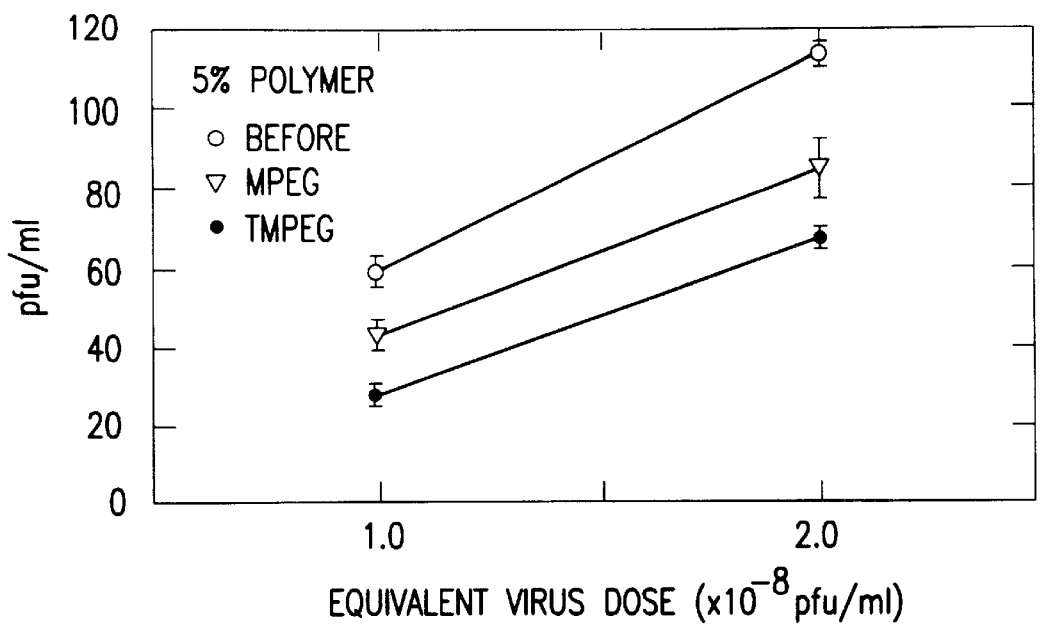
Figure 23C:
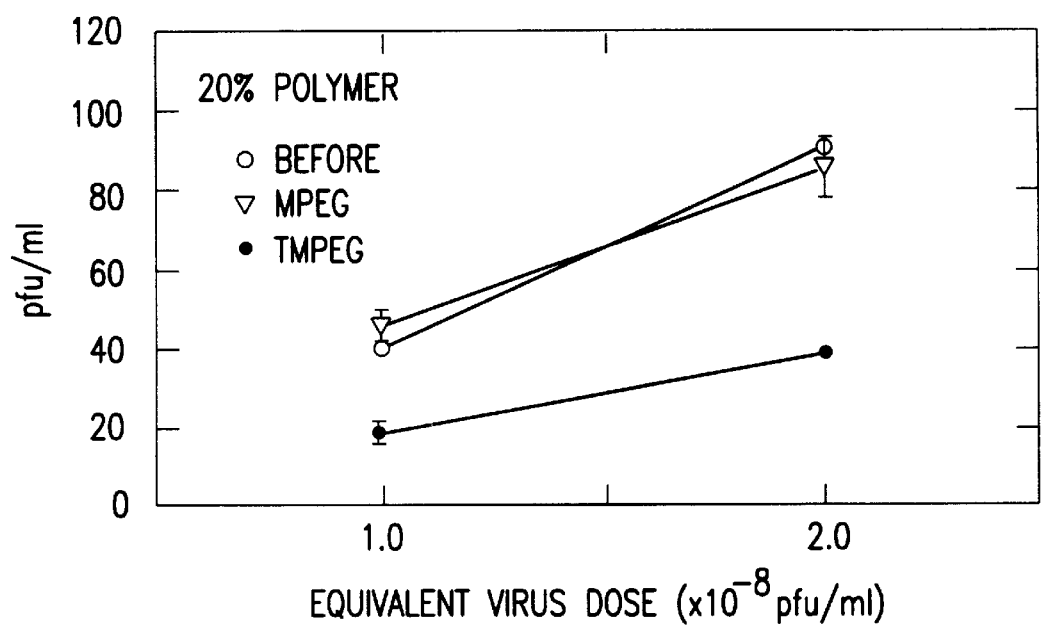

Plaque assays were carried out to assess the effect of 5% and 20% (w/v) treatment with TMPEG on virus infectivity. TK⁻143B cells, grown in MEM, supplemented with 10% FCS, were seeded in 6-well plates and allowed to adhere overnight at 37° C. Cell monolayers were infected with dilutions, $10^{-1}$ to $10^{-8}$ of TMPEG treated and MPEG treated virus (500 μl/well), for 1 hr at 37° C. After washing with PBS containing 2% FCS, the cells were overlayed with MEM containing 2.5% FCS and 1.5% carboxymethyl cellulose (CMC). After 2 days, the cell monolayers were stained with 0.1% crystal violet in 15% ethanol and the number of plaques recorded. The reduction in the numbers of plaques is shown in FIG. 23 (results of two independent experiments in upper and lower panels). Note that the number of pfu/ml does not have a linear relationship to the virus dose, thus % retention of infectivity cannot be precisely ascertained, but that TMPEG treatment does not abrogate all infectivity.

Infectivity assays were carried out by plaque assay in TK−134B cells which were stained after two days, by the addition of 300 ug/ml X-gal of β-galactosidase in the cells was ascertained following overnight incubation. The results, which are in broad agreement with the findings above, are shown in FIG. 24.

Figure 25:
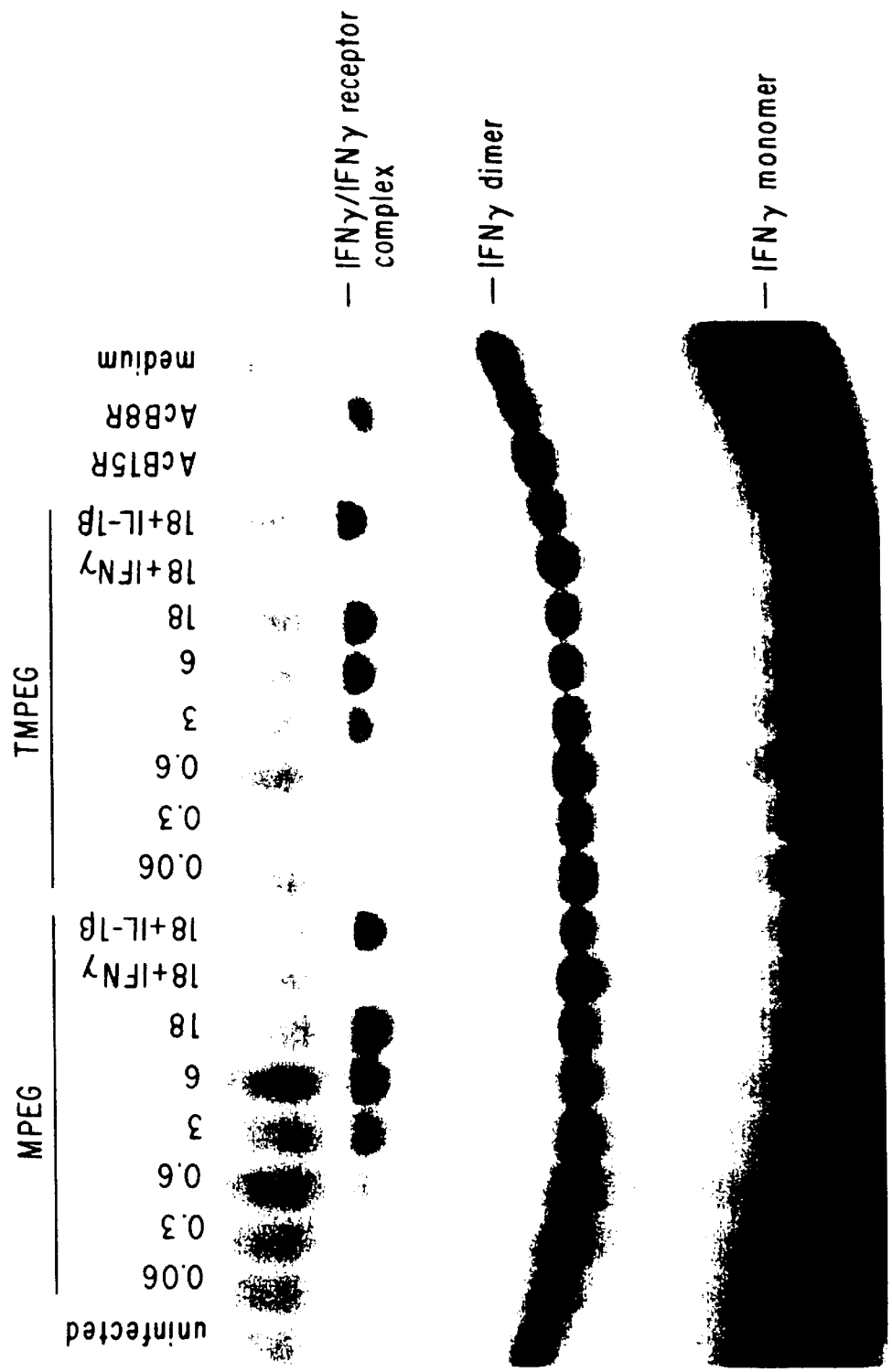
FIG. 25 shows an autoradiograph of an SDS-PAGE demonstrating the early gene expression (production of γ-IFNg receptor) following infection with vaccinia virus which had been incubated with $MPEG_{5000}$ or $TMPEG_{5000}$ using step-wise addition.

The effect of TMPEG treatment on vaccinia virus replication was assessed using assays for expression of early and late virus proteins with immunomodulatory activity. The soluble interferon-g receptor expressed from an early promoter was assayed as follows: Tk-143B cell monolayers were infected with vaccinia virus at a multiplicity of infection (moi) of 1 pfu/cell. Culture supernatants were harvested at 24 hours post infection hpi and tested for expression of INF-γ receptors using a cross-linking assay. Media from uninfected or infected cultures (24 hpi) were incubated with 1.7 nM $^{125}$I-INF-γ, in the absence or presence of 100-fold excess IL-1β or IFN-γ. IFN-g receptor complexes were cross-linked by the addition of EDC and samples were analysed by SDS-PAGE in 12% polyacrylamide gels and autoradiography (FIG. 25). The effect of TMPEG and MPEG treatment on expression of the INF-γ receptor is shown in FIG. 25, using the doses of medium (μl) indicated, from uninfected or infected cultures at 24 hpi. No variation in expression was detected. No IFN-γ binding activity was detected in medium harvested after the absorption period (data not shown). Recombinant baculovirus-infected cells expressing the vaccinia IL-1 preceptor or the vaccinia INF-γ receptor were used as negative and positive controls, respectively. The specificity of the $^{125}$I-IFN-γ binding was confirmed by competition with unlabelled IFN-γ, but not unlabelled IL-1β.

Figure 26:
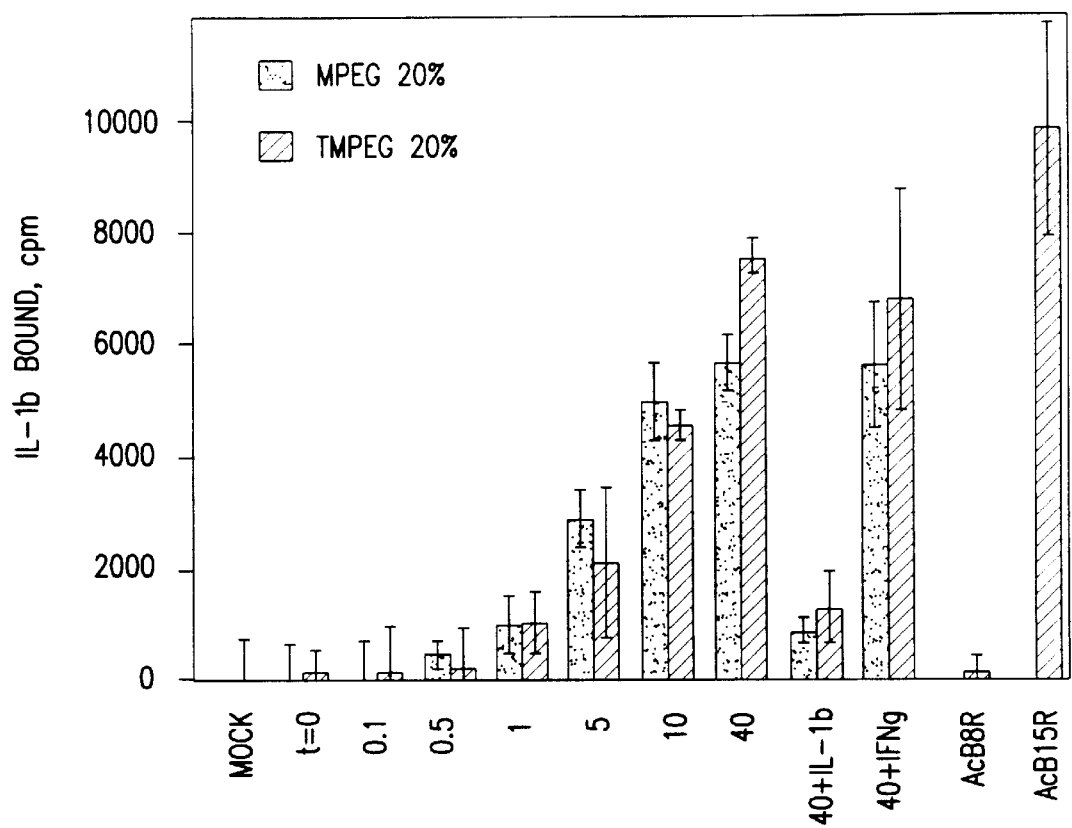
FIG. 26 demonstrates the expression of late genes (IL-1β receptor) following infection with vaccinia virus which had been incubated with $MPEG_{5000}$ or $TMPEG_{5000}$ (step-wise addition).
Figure 28A:
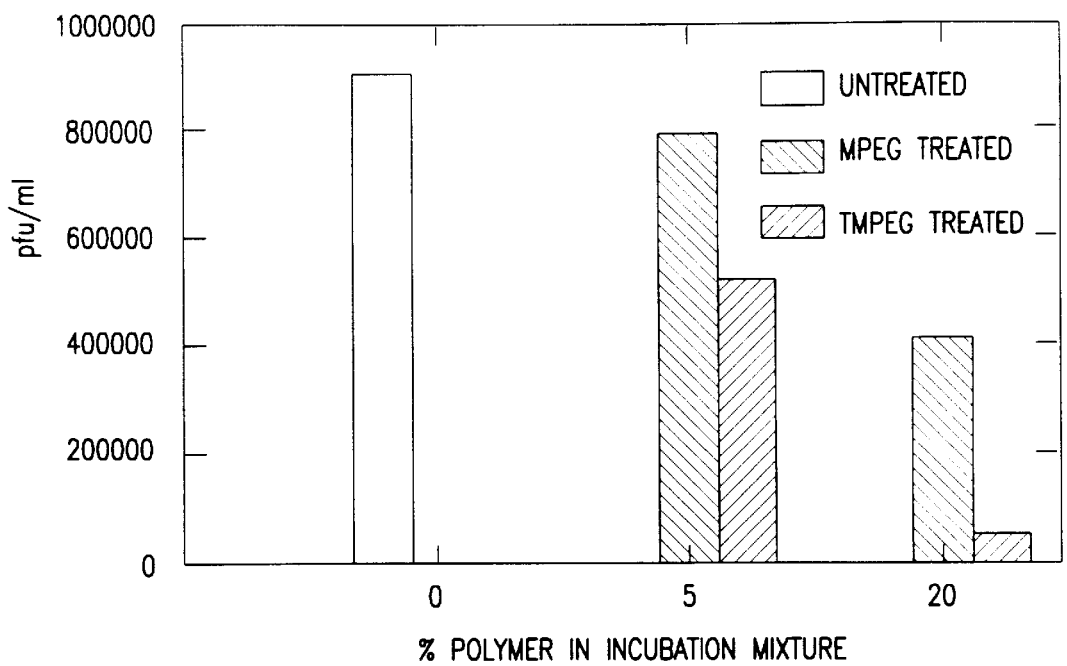
FIGS. 28A–B shows the infectivity measured by plaque assay of Retrovirus following step-wise addition of $MPEG_{5000}$ or $TMPEG_{5000}$.
Figure 28B:
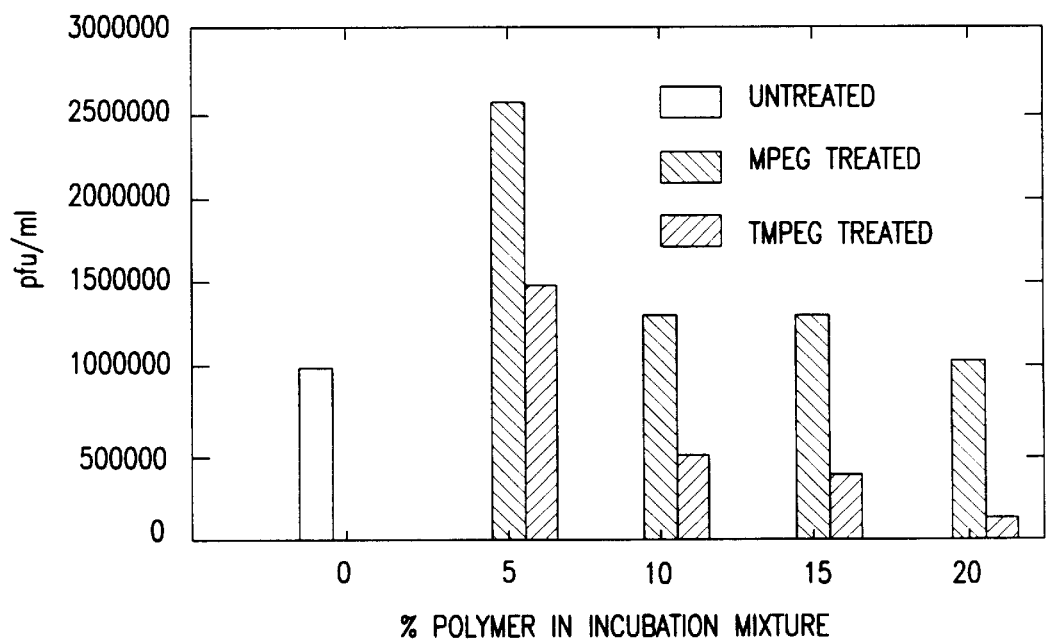
Figure 29A:
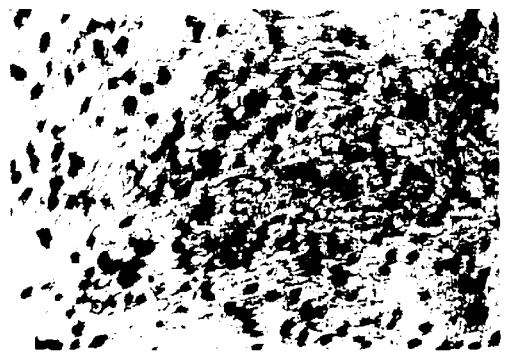
FIGS. 29A–F shows lacZ expression following infection with Retrovirus which had been incubated with $MPEG_{5000}$ or $TMPEG_{5000}$ (step-wise addition).
Figure 29B:
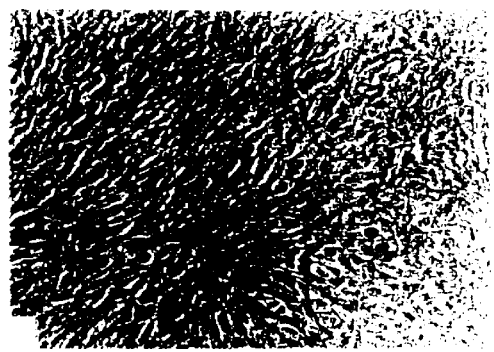
Figure 29C:
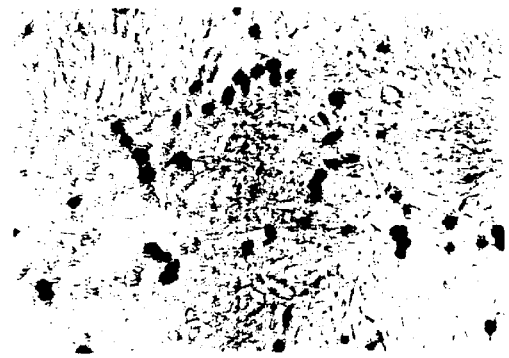
Figure 29D:
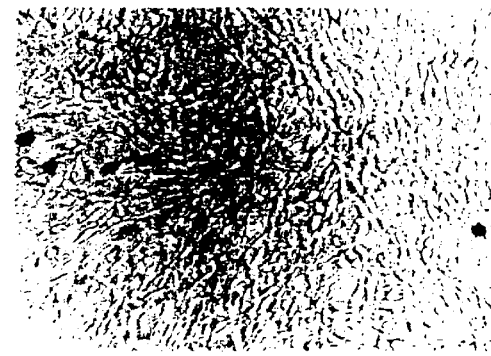
Figure 29E:
Figure 29F:

Expression of the soluble interleukin-1β receptor, expressed from a late promoter, was assayed as follows. TK−143B cell monolayers were infected with vaccinia virus at an moi of 1 pfu/cell. Culture supernatants were harvested at 24 hpi and tested for expression of IL-1β receptors in a soluble binding assay. Media from uninfected and infected cultures (24 hpi) were incubated with 140 pM $^{125}$I-IL-1β, in the presence or absence of 100 fold excess IL-1β or IFN-γ. Bound IL-β was determined by precipitation with polyethylene glycol and the precipitate collected on Whatman GF/C filters. Background radioactivity precipitated in the presence of binding medium was subtracted. One μl of medium was equivalent to 1500 cells. Specific bound radioactivity (±standard deviation) is shown in FIG. 26. At the indicated doses (μl), media assayed from cells infected with 20% MPEG and 20% TMPEG treated virus, showed little or no difference in activity. Binding activity of medium harvested after the absorption period is given as t=0. Supernatants from recombinant baculovirus infected cells, expressing vaccinia IL-1b or vaccinia IFN-g were used as positive and negative controls respectively.

FIG. 27 shows the impact of incubation with TMPEG$_{5000}$ or MPEG$_{5000}$ on neutralisation of the virus by anti vaccinia serum. Wtih the MPEG treated virus, all dilutions of serum produced a similar reduction in pfu/ml, indicative of neutralisation. A protective effect was evident in the TMPEG treated samples at 1/1000, 1/500 and possibly 1/250 dilutions of serum.

Example 18

Covalent Attachment of Polyethylene Glycol to Retrovirus

As a representitive example of retrovirus vectors, the mammalian C-type retrovirus, Molony murine leukaemia virus (MMLV) was used to demonstrate retention of infectivity in TMPEG treated virus samples.

MMLV containing a lacZ gene, encoding β-galactosidase sequence (AM-12.lacZ), obtained from Dr. Massimo Pizzato, Cancer Research Institute, Inlham Road, London, U.K., was produced in 3T3 fibroblasts grown in serum free DMEM. Monolayers of cells were infected at low multiplicity of infection (moi) for 24 hours at 37° C. Virus stocks were harvested from culture supernatant, and filtered through 0.45 um filters prior to use. Virus stocks titrated by infectivity assays in 3T3 cells, were found to be at $1\times10^6$ pfu/ml. The filtered culture supernatants, containing $1\times10^6$ pfu/ml were treated with $TMPEG_{5000}$ or $MPEG_{5000}$ in 5% steps as described in Example 16. The reactions were carried out at 25° C., allowing 30 min for each addition. The pH of the reactions was monitored, and a drop from pH 7.0 to pH 6.8 was recorded in the TMPEG 15% and 20% reactions.

Monolayers of 3T3 and CE cells were set up in 24 well plates and allowed to adhere overnight at 37° C. TMPEG and MPEG treated MMLV was diluted in serum free DMEM media ($10^{-1}$ to $10^{-5}$ dilutions), and cells were infected with each dilution (0.5 ml/well) for 4 hrs at 37° C. Following infection, the virus inoculum was removed, and replaced with 1 ml of DMEM containing 10% FCS. At 48 hours post infection (hpi), the cells were stained overnight at 37° C. with X-gal (300 mg/ml). Cells expressing β-galactocidase activity were counted, and representative dilutions recorded by photograph.

The infectivity of TMPEG and MPEG treated MMLV is shown in FIG. 28 (two independent experiments are shown in 28*a* and *b*). In both experiments TMPEG treated samples showed somewhat lower infectivity than the equivalent MPEG treated controls. The impact of sham treatment with MPEG differed between the two experiments, showing modest reduction in infectivity in FIG. 28*a* and an apparent increase versus untreated control at 5% MPEG and no reduction versus untreated control at 10, 15 and 20% MPEG respectively in FIG. 28*b*.

Cells showing β-galactocidase activity are represented in FIG. 29. Panels A and B show untreated virus at dilutions $10^{-1}$ and $10^{-4}$ respectively. In the remaining panels the dilutions giving the most comparable levels of infectivity in the treated samples are shown. Panels C and D show 5% and 20% TMPEG treated virus both at $10^{-4}$ dilution and panels E and F show 5% and 20% MPEG treated virus at $10^{-2}$ and $10^{-3}$ dilutions respectively.

Example 19

Covalent Attachment of Polyethylene Glycol to Herpesvirus

As an example of Herpesvirus based vectors, Herpes simplex I strain 17 (HSV-I strain 17), obtained from Dr. S. Efstathiou, Division of Virology, Department of Pathology, University of Cambridge, Tennis Court Road, Cambridge, U.K., was used to demonstrate the covalent attachment of TMPEG to a Herpesvirus vector, and to assess the effect of the polymer on virus infectivity.

Virus stocks of HSV-I strain 17, was prepared by infecting roller bottles of BHK cells, at an moi of 0.01 (0.01 pfu/cell).

The infected cells were incubated in Glasgow MEM (GMEM Life Technologies, Inc.) containing 10% FCS (plus penecillin/streptomycin 1000 u/ml), at 37° C. until complete cytopathic effect (CPE) was observed. The virus from both the infected cells, and the culture supernatant was harvested, and purified on a 15% Ficoll gradient in endotoxin-free PBS. The virus was then separated by ultracentrifugation, and resuspended in PBS. Aliquots of the purified virus stock were stored at −70° C. The stock innoculum was titrated by plaque assay and was determined to be at $1.1 \times 10^9$ pfu/ml.

Aliquots of the purified virus were reacted with either TMPEG or MPEG, in 5% (w/v) steps as described in Example 16. The reactions were carried out on a rotary wheel, at 25° C., allowing 30 min for each addition of PEG. The pH of the reactions were monitored at each step, and was found to remain stable at pH 7.0. Following treatment with PEG, the reacted virus samples were stored at −70° C.

The retention of HSV-1 Infectivity was assessed following treatment with TMPEG as follows. Vero cells and BHK cells were trypsinised using standard procedures, and maintained on ice. Serial 10 fold dilutions of the untreated, MPEG treated and TMPEG treated virus samples were prepared in GMEM, containing 2% FCS. $2 \times 10^6$ Vero cells and $3 \times 10^7$ BHK cells were added to each virus dilution ($10^{-3}$ to $10^{-8}$), and the cells were infected by shaking gently at 37° C. The infected cells were seeded in 6 cm dishes, with the addition of GMEM, containing 10% FCS (plus penecillin/streptomycin 1000 units/ml) and 1% carboxymethyl cellulose (CMC). The cells were incubated at 37° C. for 48 hrs. At 48 hpi, the assays were fixed in 10% formalin, and stained with toluidine blue. The number of plaques was recorded.

Figure 30A:
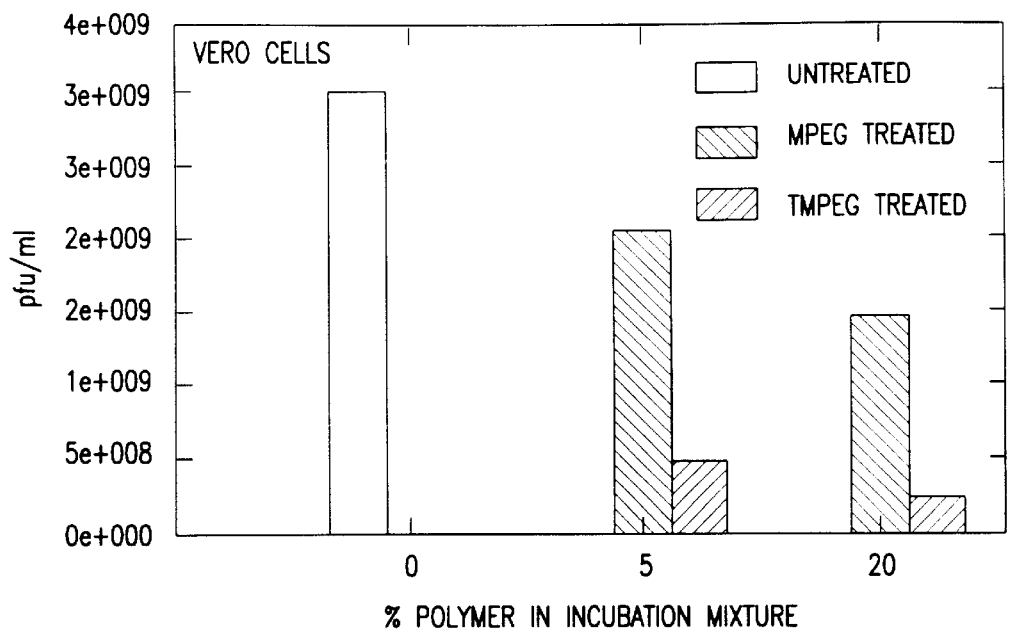
FIGS. 30A–B shows the infectivity measured by plaque assay of Herpesvirus following step-wise addition of $MPEG_{5000}$ or $TMPEG_{5000}$.
Figure 30B:
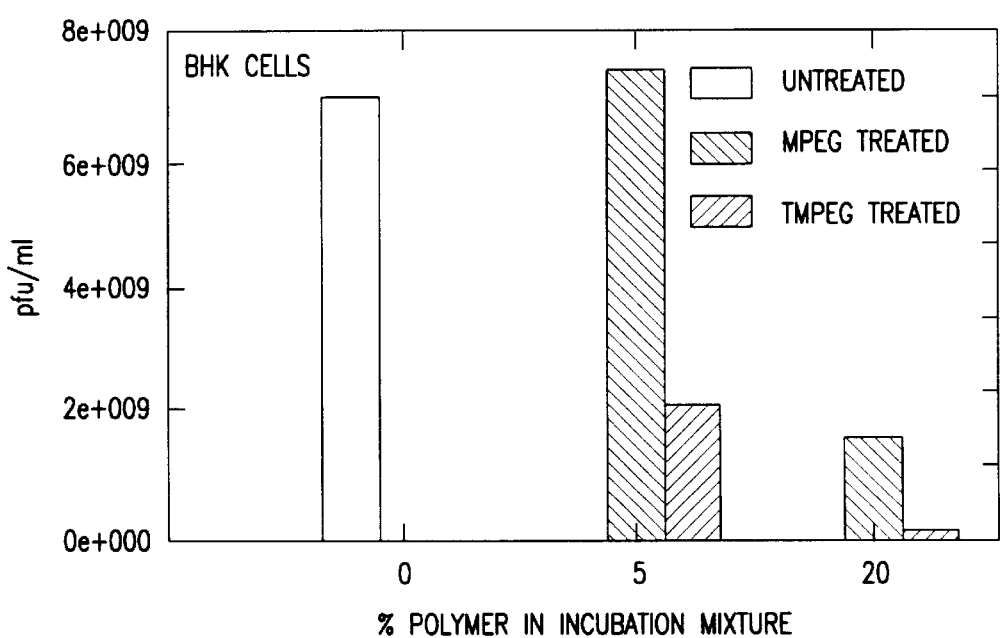

FIG. 30 shows the HSV-1 infectivity assays carried out in Vero cells (Panel A) and BHK cells (Panel B), respectively. Reaction with 5% MPEG produced a reduction of infectivity in Vero cells, but infectivity was not affected by this level of exposure to MPEG in BHK cells. Although treatment with TMPEG resulted in some loss of HSV-I infectivity, in both cell lines some retention of infectivity was observed in both cell lines.

Example 20
Covalent Attachment of Polyvinyl Pyrrolidone (PVP) to Adenovirus ONYX-015

PVP is a linear water soluble polymer which can be activated in a similar fashion to polyethylene glycol. In this example PVP carboxylic acid was activated by the succinimidyl active ester method (Delgado et al., *Crit. Rev. Therap. Drug Carrier Syst.* 9:249–304, 1992) to provide activated PVP which can form PVP-modified virus (kindly supplied by Prof F. Veronese, University of Padua, Padua, Italy). PVP carboxylic acid was used as a control polymer with which to sham treat the virus, since this is unable to attach covalently to the virus. Activated and unactivated polyvinyl pyrrolidine (PVP) were added at a concentration of 5% (w/v) to adenovirus ONYX-015 ($1 \times 10^{11}$ pfu/ml) and incubated for 30 min at 25° C. The samples were then assessed for polymer attachment using IEC essentially as described in Example 15, using the buffers A and B detailed above, but with the following gradient conditions: 0–5 minutes 0% buffer-B; 5–22 minutes 0–50% buffer-B; 22–27 minutes 100% buffer-B.

Figure 31A:
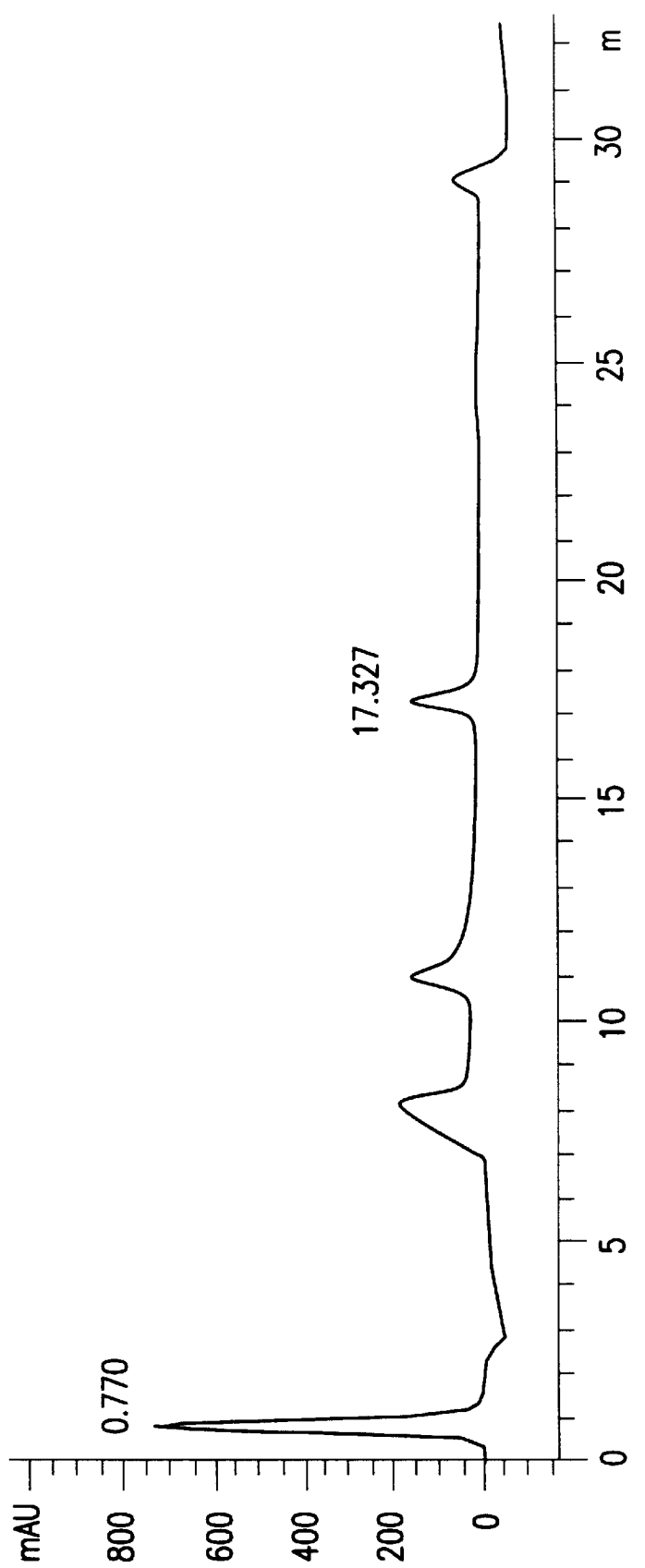
FIGS. 31A–B shows the elution profile of ONYX-015 incubated with PVP (panel 32a) and activated PVP (panel 32b) from 1 ml Resource Q column (Pharmacia).
Figure 31B:
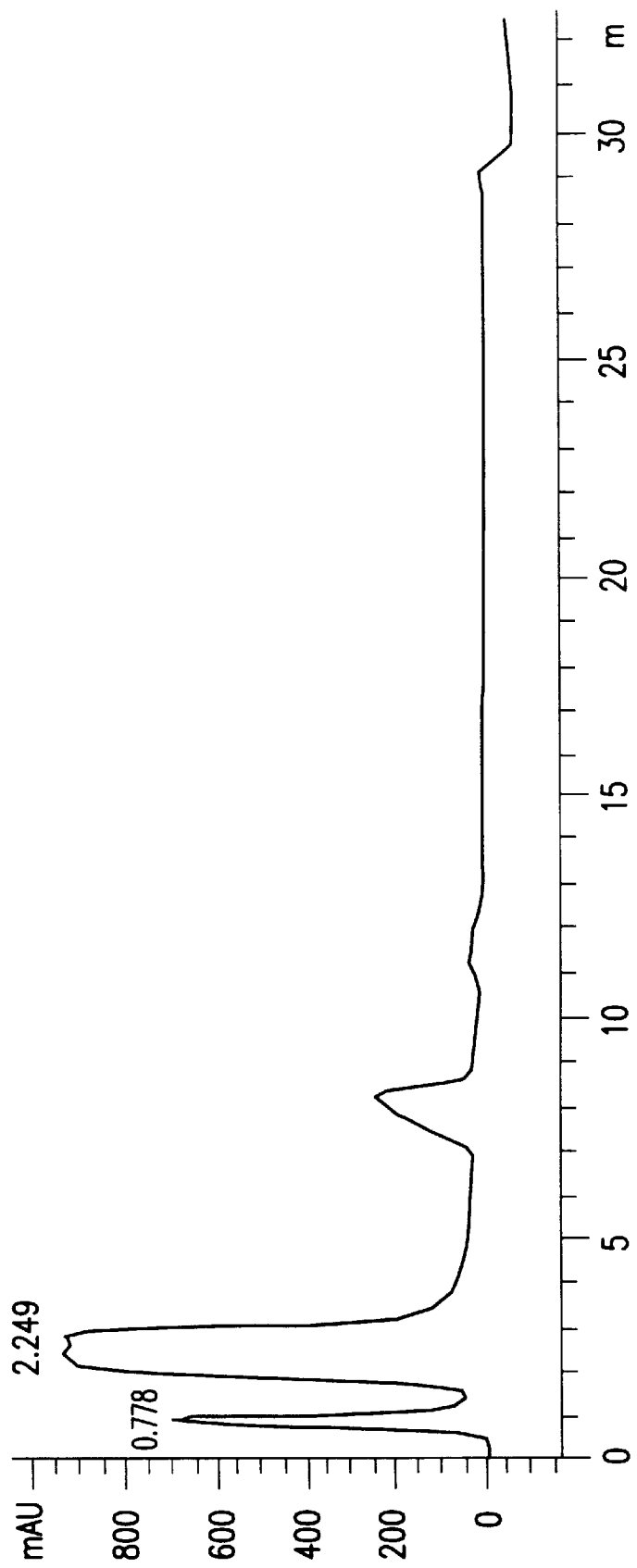

The IEC data are shown in FIGS. 31a and b. In the virus sample treated with unactivated PVP, a peak for unmodified virus is detected at 17.3 min, whereas in the sample treated with 5% activated PVP, no peak is detected at this position, suggesting that complete modification of the virus had occurred with 5% activated PVP. The peak at circa 11 min in FIG. 31a, which is much smaller in FIG. 31b, is a variable artefact. In the sample treated with activated PVP a large peak is evident at 2.2 min (truncated in the figure). This relates to the PVP in the sample, but may also obscure the PVP-virus. Shrouding of surface charge of the virus particle by PVP is anticipated thus the PVP modified virus would be expected to eluted much earlier than the virus itself.

Example 21
Tumor Localization of PEGylated Virus

PEGylated Adenovirus ONYX-015 was prepared by incubation with TMPEG5000 as described in Example 16, to give final concentrations of 20% polymer. Control Adenovirus ONYX-015 was prepared by incubation with MPEG5000. The PEGylated and control virus samples were analyzed by IEC as described in Example 15, and the 20% TMPEG sample was found to contain no unmodified virus.

A human LS174T colon carcinoma (obtained from the Clinical Oncology Department, Royal Free Hospital School of Medicine, London, NW3, U.K.) was implanted on the flank of nude mice (MF1) (obtained from the Comparative Biology Unit, Royal Free Hospital School of Medicine, London, NW3, U.K.) by placing a small piece of tumor under the skin. Once the tumor was established (typically 3 weeks after implantation), the animals were injected into the tail vein, with a dose of equivalent $1 \times 10^8$ pfu/animal (100 μl/animal), of PEGylated or control virus. At 24 hours post injection, the animals were sacrificed and tumor and liver were taken. The tissues were prepared for microscopy as follows: the tissues were cut into small pieces and washed once in PBS, fixed in 3% paraformaldehyde/0.3% glutaraldehyde for 1 hr. at 4° C. and then infiltrated with 2.3 M sucrose for 24–48 hours at 4° C. The samples were frozen at −20° C., and cryosectioned onto slides. Semi-thin section were stained for 1 hour at room temperature in primary anti-hexon antibody (Access Biomedic, Inc., diluted 1:1000 in PBSB), washed in PBS, and then incubated for 1 hour in secondary goat anti rabbit FITC conjugate (Sigma, diluted 1:40 in PBS). The sections were washed in PBS and distilled water, and mounted in Citifluor anti-fade mountant. Sections were examined by confocal microscopy.

Figure 32A:
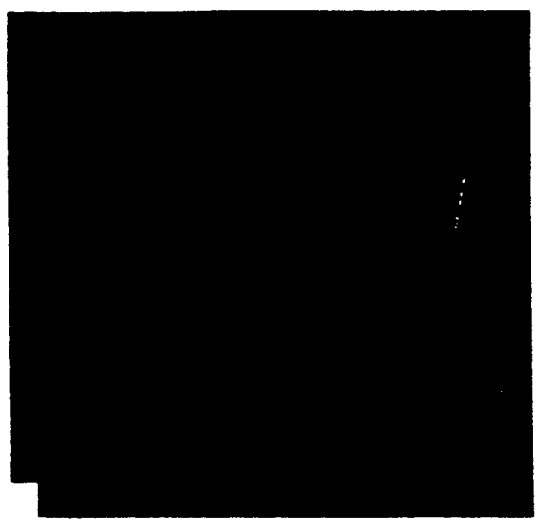
FIG. 32 shows immunofluorescent staining of liver (A) and tumor sections (B and C) taken from nude mice bearing LS174T human colon carcinoma injected with PEGylated virus (A and B) or control virus (C).
Figure 32B:
Figure 32C:

Sections taken from tumor tissues showed distribution of PEGylated and control virus within the tissue (FIGS. 32B and C). Sections taken from the liver tissue showed no localization of virus in either PEGylated virus (FIG. 32A) or control virus (data not shown). The localization of the PEGylated virus in the tumor is shown in FIG. 32B. Some tumor localization was also seen for the sham PEGylated virus (FIG. 32C). (FIGS. 32B and C are at the same magnification).

Example 22
Transgene Expression of PEGylated Ad2/β-gal 4 Virus in Immune Mice

Ad2/β-gal 4 virus (U.S. Pat. No. 5,670,488) was PEGylated with 10% tresyl mPEG (TMPEG—Sigma Chemicals, St. Louis, Mo.) as already described. PEGylated virus was purified from unreacted TMPEG by banding on cesium chloride gradients (Rich et al., *Human Gene Therapy* 4:461–476, 1993). The purified PEGylated virus was dialysed into phosphate buffered saline (PBS), 5% sucrose and the titre was determined by end point dilution on HEK293 cells using fluorescent isothiocyanate (FITC)-conjugated anti-hexon antibody (Rich et al., 1993). Control or sham treated vector was treated with non-reactive MPEG and was purified and titred as described for TMPEG virus. PEGylated and sham treated virus were instilled into immune and naive mice. The dose for each vector was $2 \times 10^8$ iu/mouse (equivalent to ~2×10$^{10}$ particles), the dose volume per mouse was 100 μl. Immune mice had previously been instilled with Ad2-CFTR-8 vector (U.S. Pat. No. 5,707,618) and had titres to adenovirus in the range 25,000–51,200.

Three days after instillation the animals were sacrificed and lung tissue from individual animals were homogenised and β-galactosidase activity in the homogenate was assessed using a commercially available assay kit according to manufacturer's instructions (Galactolight Kit, Tropix, Bedfor, Mass.). The protein concentration of lung homogenates was determined using the BioRad DC reagent (BioRad, Hercules, Calif.) and the results expressed as relative light units (RLU)/ug protein.

Figure 33:
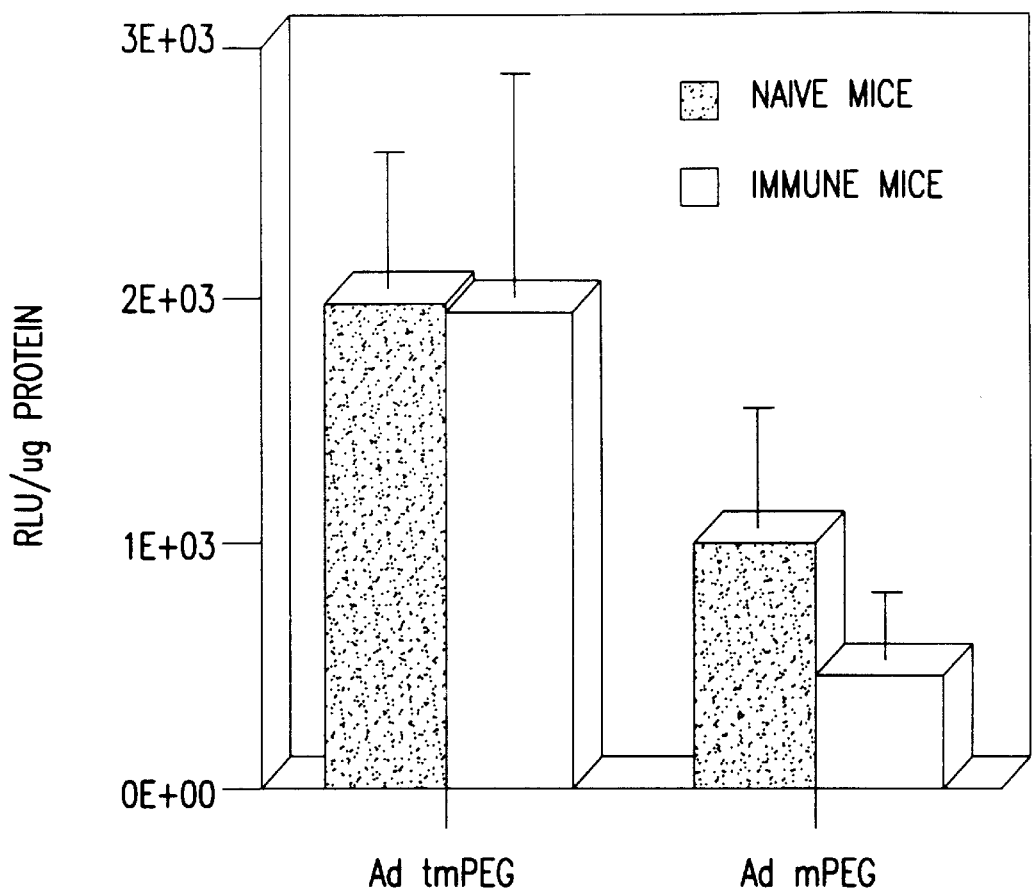
FIG. 33 shows transgene expression in mice infected with PEGylated or sham treated adenoviral vectors.

FIG. 33 shows the β-galactosidase expression for PEGylated virus (Ad tmPEG) and sham treated virus (Ad mPEG). Results shown are the mean ±standard deviation of the values obtained with individual animals. β-Galactosidase expression was measured in the lungs of naive mice for both the MPEG and the TMPEG (N=2) viral preparations. In the pre-immunised mice (N=4) the sham treated virus (Ad MPEG) had reduced levels of β-galactosidase expression (~47% of the β-galactosidase expression measured in naive animals), presumably due to neutralisation by adenovirus specific antibodies. In contrast in the pre-immunised mice (N=3) the PEGylated virus gave levels of β-galactosidase expression equivalent to those measured in naive animals (~89% of the expression measured in naive animals). Thus PEGylation of the adenovirus protects the virus from neutralisation, allowing full expression of the vector in the target tissue in the presence of an immune response.

We claim:

1. A polymer-modified virus comprising a virus particle having at least one polyethylene glycol (PEG) polymer molecule bound thereto, said virus retaining viral infectivity wherein said PEG polymer molecule is bound to said virus particle by activating a PEG polymer molecule to provide an activated moiety and coupling said activated PEG polymer molecule to said virus, wherein said activated PEG polymer molecule is tresylmonomethoxypolyethylene glycol (TMPEG) having an average molecular weight of about 5000 daltons.

2. The polymer-modified virus of claim 1 wherein said virus is retrovirus, adenovirus, adenoassociated virus, herpesvirus or poxvirus.

3. The polymer-modified virus of claim 1 wherein said virus is adenovirus.

4. The polymer-modified virus of claim 3 wherein said adenovirus is a recombinant adenoviral vector.

5. The polymer-modified virus of claim 4 wherein said virus is a recombinant viral vector comprising a transgene.

6. The polymer-modified virus of claim 1 wherein said activated PEG polymer molecule is directly covalently bound to said virus particle.

7. A composition comprising the polymer-modified virus of claim 1 or 4 and a carrier.

8. A method for introducing a transgene into a target cell comprising introducing the polymer-modified virus of claim 5 into said target cell.

9. The method of claim 8 wherein said polymer-modified virus is introduced into said target cell by infection.

10. A method for delivering a virus to a tumor comprising administering the polymer-modified virus of claim 1 to a subject having a tumor under conditions whereby the polymer-modified virus localizes to said tumor.

11. The method of claim 10 wherein said polymer-modified virus is present in a composition with a physiologically acceptable carrier.

12. A method of making a polyethylene glycol-modified virus comprising a virus particle having at least one activated polyethylene glycol (PEG) polymer molecule bound thereto, said method comprising coupling tresyl-monomethoxypolyethylene glycol (TMPEG) to said virus particle, wherein said TMPEG has an average molecular weight of about 5000 daltons.

13. The method of claim 12 wherein said virus is a recombinant adenoviral vector.

14. The method of claim 13 wherein said recombinant adenoviral vector contains a transgene.

15. A method of making a polymer-modified virus comprising a virus particle having at least one activated polyethylene glycol (PEG) polymer molecule bound thereto, said method comprising activating a PEG polymer molecule to provide an activated moiety, and coupling said activated PEG polymer molecule to said virus particle, wherein said activated PEG polymer molecule is tresyl-monomethoxypolyethylene glycol (TMPEG) having an average molecular weight of about 5000 daltons.

* * * * *

UNITED STATES PATENT AND TRADEMARK OFFICE
CERTIFICATE OF CORRECTION

PATENT NO.    : 6,569,426 B2                                    Page 1 of 4
DATED         : May 27, 2003
INVENTOR(S)   : Smith et al.

It is certified that error appears in the above-identified patent and that said Letters Patent is hereby corrected as shown below:

<u>Title page,</u>
Item [75], Inventors, "Trusham" should read -- Boreham Wood --

<u>Column 2,</u>
Lines 46 and 65, "shows" should read -- show --
Lines 52, 54, 57 and 59, "depicts" should read -- depict --

<u>Column 3,</u>
Lines 6, 13, 34, 37 and 44, "shows" should read -- show --
Lines 28 and 30, "depicts" should read -- depict --

<u>Column 4,</u>
Lines 4, 7, 10 and 13, "shows" should read -- show --
Lines 43 and 44, "polyalkalene" should read -- polyalkylene --
Line 45, "alkalene" should read -- alkylene --

<u>Column 5,</u>
Line 33, "icroviridae" should read -- Icroviridae --
Line 48, "adenoassociated" should read -- adeno-associated --
Line 48, "pokvirus" should read -- poxvirus --

<u>Column 6,</u>
Line 65, "succimimide" should read -- succinimide --

<u>Column 9,</u>
Line 18, "herein above" should read -- hereinabove --
Line 34, "eg." should read -- e.g., --

<u>Column 12,</u>
Line 43, "are" should read -- is --; and "depend" should read -- depends --

<u>Column 13,</u>
Line 21, "Internal" should read -- internal --
Line 28, "Kv." should read -- kV. --

<u>Column 14,</u>
Line 2, "Instrument's" should read -- Instruments' --
Lines 21 and 29, "step wise" should read -- stepwise --

<u>Column 15,</u>
Line 29, "chemiluminesent" should read -- chemiluminescent --
Line 31, "compares" should read -- compare --

UNITED STATES PATENT AND TRADEMARK OFFICE
CERTIFICATE OF CORRECTION

PATENT NO. : 6,569,426 B2
DATED : May 27, 2003
INVENTOR(S) : Smith et al.

It is certified that error appears in the above-identified patent and that said Letters Patent is hereby corrected as shown below:

Column 17,
Lines 17 and 59, "lgG" should read -- IgG --
Line 27, "lgG" (both occurrences) should read -- IgG --

Column 19,
Line 31, "strepavidin-HRP" should read -- streptavidin-HRP --

Column 20,
Line 14, "TNlPEG:NH$_2$" should read -- TMPEG:NH$_2$ --
Line 23, "lead" should read -- led --

Column 21,
Line 28, "OFPEGylated" should read -- of PEGylated --
Line 39, "Ad 2-$\beta$-gal" should read -- Ad2-$\beta$-gal --

Column 22,
Line 18, "mPEG$_{5000}$b)" should read -- mPEG$_{5000}$ b) --
Line 34, "pyridylditthio" should read -- pyridyldithio --
Line 34, "peropionate" should read -- propionate --

Column 23,
Line 20, "cytoplathic" should read -- cytopathic --
Line 48, "PEG:1-" should read -- PEG:- --
Line 49, "ysine" should read -- lysine --; and "PEG:1-" should read -- PEG:- --
Line 50, "ysine" should read -- lysine --
Lines 60 and 62, "flow through" should read -- flow-through --

Column 24,
Table 8, "Flow through" should read -- Flow-through --

Column 26,
Lines 12-13, "chromatograpy" should read -- chromatography --
Lines 15 and 36, "MgCl2" should read -- MgCl$_2$ --
Line 21, "Tris base,pH" should read -- Tris base, pH --; and "MgCl2" should read -- MgCl$_2$ --
Line 37, "buffer A. They" should read -- buffer A. ¶They --
Line 38, "of," should read -- of --

Column 27,
Line 32, "shows" should read -- show --
Line 49, "innoculum" should read -- inoculum --
Line 55, "innoculum" should read -- inoculum --; and "overlayed" should read -- overlaid --

UNITED STATES PATENT AND TRADEMARK OFFICE
CERTIFICATE OF CORRECTION

PATENT NO. : 6,569,426 B2
DATED : May 27, 2003
INVENTOR(S) : Smith et al.

It is certified that error appears in the above-identified patent and that said Letters Patent is hereby corrected as shown below:

Column 27 (cont'd),
Line 58, "overlayed" should read -- overlaid --

Column 28,
Line 15, "8 well" should read -- 8-well --
Line 18, "innoculum" should read -- inoculum --
Line 34, "Immunofluoresence" should read -- Immumofluorescence --

Column 29,
Line 2, "overlayed" should read -- overlaid --
Line 14, "TK$^-$134B" should read -- TK$^-$143B --
Line 15, "ug/ml" should read -- $\mu$g/ml --
Line 23, "Tk-143B" should read -- TK$^-$143B --
Lines 27 and 34, "INF-$\gamma$" should read -- IFN-$\gamma$ --
Line 29, "$^{125}$INF-$\gamma$" should read -- $^{125}$IFN-$\gamma$ --
Line 30, "IFN-g" should read -- IFN-$\gamma$ --
Line 40, "IL-1" should read -- IL-1$\beta$ --; and "INF-$\gamma$" should read -- IFN-$\gamma$ --
Line 53, "IL-$\beta$" should read -- IL-1$\beta$ --
Line 64, "IL-1b" should read -- IL-1$\beta$ --

Column 30,
Line 1, "Wtih" should read -- With --
Line 8, "innoculum" should read -- inoculum --
Lines 35 and 48, "$\beta$-galactocidase" should read -- $\beta$-galactosidase --

Column 31,
Lines 3 and 27, "penecillin" should read -- penicillin --
Line 8, "innoculum" should read -- inoculum --
Line 17, "Infectivity" should read -- infectivity --
Line 20, "10 fold" should read -- 10-fold --
Line 44, "water soluble" should read -- water-soluble --

Column 32,
Line 2, "artefact" should read -- artifact --
Line 7, "to eluted" should read -- to be eluted --
Line 37, "anti rabbit" should read -- anti-rabbit --
Line 55, "tresyl mPEG" should read -- tresyl-mPEG --

UNITED STATES PATENT AND TRADEMARK OFFICE
CERTIFICATE OF CORRECTION

PATENT NO. : 6,569,426 B2
DATED : May 27, 2003
INVENTOR(S) : Smith et al.

It is certified that error appears in the above-identified patent and that said Letters Patent is hereby corrected as shown below:

Column 33,
Line 9, "Bedfor" should read -- Bedford --
Line 13, "(RLU)/ug" should read -- (RLU)/$\mu$g --
Line 39, "tresylmonomethoxypolyethylene" should read
-- tresyl-monomethoxypolyethylene --
Line 43, "adenoassociated" should read -- adeno-associated --

Signed and Sealed this

Twenty-eighth Day of October, 2003

JAMES E. ROGAN
*Director of the United States Patent and Trademark Office*